(12) United States Patent
Moriyama et al.

(10) Patent No.: US 12,077,531 B2
(45) Date of Patent: Sep. 3, 2024

(54) IMIDAZOPYRIDINONE COMPOUND

(71) Applicant: KISSEI PHARMACEUTICAL CO., LTD., Matsumoto (JP)

(72) Inventors: Akihiro Moriyama, Azumino (JP); Yasushi Takigawa, Azumino (JP)

(73) Assignee: KISSEI PHARMACEUTICAL CO., LTD., Matsumoto (JP)

( * ) Notice: Subject to any disclaimer, the term of this patent is extended or adjusted under 35 U.S.C. 154(b) by 877 days.

(21) Appl. No.: 17/268,011

(22) PCT Filed: Sep. 12, 2019

(86) PCT No.: PCT/JP2019/035792
§ 371 (c)(1),
(2) Date: Feb. 11, 2021

(87) PCT Pub. No.: WO2020/054788
PCT Pub. Date: Mar. 19, 2020

(65) Prior Publication Data
US 2021/0206765 A1 Jul. 8, 2021

(30) Foreign Application Priority Data
Sep. 13, 2018 (JP) ................................. 2018-171839

(51) Int. Cl.
C07D 471/04 (2006.01)
A61K 9/00 (2006.01)
A61P 1/00 (2006.01)

(52) U.S. Cl.
CPC .......... *C07D 471/04* (2013.01); *A61K 9/0053* (2013.01); *A61P 1/00* (2018.01)

(58) Field of Classification Search
CPC .................................................... C07D 471/04
See application file for complete search history.

(56) References Cited

U.S. PATENT DOCUMENTS

| | | | |
|---|---|---|---|
| 6,713,474 B2 | 3/2004 | Hirst et al. | |
| 2005/0107399 A1 | 5/2005 | Boman et al. | |
| 2007/0142369 A1 | 6/2007 | van Heek et al. | |
| 2009/0181957 A1 | 7/2009 | Ando et al. | |
| 2009/0298811 A1 | 12/2009 | Ando et al. | |
| 2010/0137297 A1 | 6/2010 | Fletcher et al. | |
| 2011/0046132 A1 | 2/2011 | Hocutt et al. | |
| 2011/0077267 A1 | 3/2011 | Mitani et al. | |
| 2011/0152304 A1 | 6/2011 | Pierce et al. | |
| 2012/0322772 A1 | 12/2012 | Flamme et al. | |
| 2019/0177318 A1 | 6/2019 | Luo et al. | |

FOREIGN PATENT DOCUMENTS

| | | |
|---|---|---|
| JP | 2002-526500 A | 8/2002 |
| JP | 2007-505127 A | 3/2007 |
| JP | 2008-533121 A | 8/2008 |
| JP | 2010-503654 A | 2/2010 |
| JP | 2011-37841 A | 2/2011 |
| JP | 2011-519857 A | 7/2011 |
| WO | 00/17203 A1 | 3/2000 |
| WO | 01/72751 A1 | 10/2001 |
| WO | 03/037890 A2 | 5/2003 |
| WO | 2007/015877 A2 | 2/2007 |
| WO | 2009/029609 A1 | 3/2009 |
| WO | 2010/030500 A1 | 3/2010 |
| WO | 2011/096490 A1 | 8/2011 |
| WO | 2014/181813 A1 | 11/2014 |
| WO | 2015/052675 A1 | 4/2015 |
| WO | 2015/139619 A1 | 9/2015 |
| WO | 2016/148306 A1 | 9/2016 |
| WO | 2017/066014 A1 | 4/2017 |
| WO | 2018/036469 A1 | 3/2018 |

OTHER PUBLICATIONS

Marks et al., "Oral Delivery of Prolyl Hydroxylase Inhibitor: AKB-4924 Promotes Localized Mucosal Healing in a Mouse Model of Colitis", Inflamm Bowel Dis, vol. 21, No. 2, Feb. 2015, pp. 267-275.

(Continued)

*Primary Examiner* — Golam M Shameem
(74) *Attorney, Agent, or Firm* — WHDA, LLP

(57) ABSTRACT

The present invention aims to provide a novel compound which has prolyl hydroxylase (PHDs) inhibitory effect and which is useful for the treatment of inflammatory bowel diseases such as ulcerative colitis and the like. The present invention relates to a imidazopyridinone compound represented by the following formula (I) or a pharmaceutically acceptable salt thereof. The compounds of the present invention or pharmaceutically acceptable salts thereof which have prolyl hydroxylase inhibitory effect and, are useful as agents for the treatment of inflammatory bowel diseases such as ulcerative colitis and the like. In an embodiment, the present invention relates to a method for treating an inflammatory bowel disease

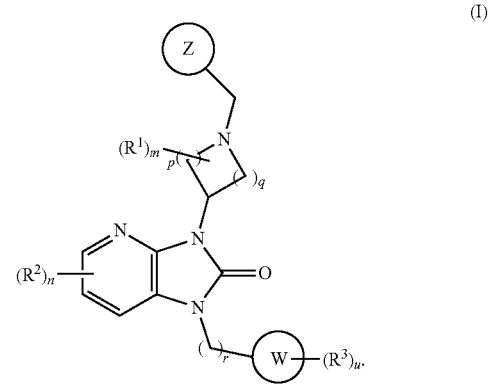

19 Claims, No Drawings

(56) References Cited

OTHER PUBLICATIONS

Chan et al., "Pharmacological targeting of the HIF hydroxylases—A new field in medicine development", Molecular Aspects of Medicine, vols. 47-48, 2016, pp. 54-75.

Deng et al., "Novel complex crystal structure of prolyl hydroxylase domain-containing protein 2 (PHD2): 2,8-Diazaspiro[4.5]decan-1-ones as potent, orally bioavailable PHD2 inhibitors", Bioorganic & Medicinal Chemistry, vol. 21, 2013, pp. 6349-6358.

Vachal et al., "1,3,8-Triazaspiro[4.5]decane-2,4-diones as Efficacious Pan-Inhibitors of Hypoxia-Inducible Factor Prolyl Hydroxylase 1-3 (HIF PHD1-3) for the Treatment of Anemia", Journal of Medicinal Chemistry, vol. 55, 2012, pp. 2945-2959.

International Search Report and Written Opinion, dated Nov. 12, 2019 issued in counterpart International Application No. PCT/JP2019/035792 (15 pages; w/ English translation and machine translation).

Wu, Yue et al: "Small-molecule inhibitors of HIF-PHD2: a valid strategy to renal anemia treatment in clinical therapy". MedChemComm 2016, vol. 7, No. 7, pp. 1271-1284; Cited in European Extended Search Report dated Feb. 7, 2022. (14 pages).

Owen D R et al: "2,4-Diaminopyridine δ-opioid receptor agonists and their associated hERG pharmacology". Bioorganic & Medicinal Chemistry Letters 2009, vol. 19, No. 6, pp. 1702-1706; Cited in European Extended Search Report dated Feb. 7, 2022. (5 pages).

Kuethe J T et al: "Synthesis of Disubstituted Imidazo[4,5-b]pyridin-2-ones". Journal of Organic Chemistry 2004, vol. 69, No. 22, pp. 7752-7754; Cited in European Extended Search Report dated Feb. 7, 2022. (3 pages).

IMIDAZOPYRIDINONE COMPOUND

TECHNICAL FIELD

The present invention relates to imidazopyridinone compounds useful as medicaments. More particularly, the present invention relates to imidazopyridinone compounds or pharmaceutically acceptable salts thereof which have a prolyl hydroxylase inhibitory activity and which are useful as agents for the treatment of an inflammatory bowel disease such as ulcerative colitis.

BACKGROUND ART

Inflammatory bowel disease (IBD) are chronic diseases in which inflammation and ulcers are caused in the intestinal mucosa due to excessive immune response. IBD include, for example, ulcerative colitis and Crohn's disease.

Ulcerative colitis is a large intestine disease causing diffuse non-specific inflammation of uncertain cause. Large intestine mucosa is ulcerated, and erosion or ulcer may be caused in mucosa. Ulcerative colitis may be divided into "active phase" in which bloody stool, erosion, ulcer and the like are observed and "remission phase" in which observations of the active phase disappear. Long-term treatment is required because relapse and remission are often repeated in the course.

For the treatment of ulcerative colitis, a 5-aminosalicylic acid formulation (5-ASA) is first used as a standard agent. However, the effectiveness of 5-ASA is approximately 50 to 65%, and patients with remission by administration of 5-ASA are approximately 30 to 45%. When the effective of 5-ASA is not observed, a steroid is used. Immunosuppressive agents, anti-TNF-α antibodies and the like are sometimes used for the treatment of ulcerative colitis in addition to those medicaments. However, all the medicaments have problems such as side effects and careful administration. Therefore, a therapeutic agent having a novel mode of action for ulcerative colitis is desired.

It has been known that expression of genes associated with barrier function of gastrointestinal epithelium is induced by hypoxia-inducible factor 1α (HIF-1α) in a pathological condition of IBD. HIF-1α is one of the subtypes of hypoxia-inducible factor α (HIF-α). HIF-α is stabilized in a hypoxic environment (Hypoxia), and then it activates the transcription of several genes in response to hypoxia. In contrast, the proline residues of HIF-α are hydroxylated by prolyl hydroxylases (PHDs) in an oxygen-rich environment (Normoxia), and then the HIF-α is degraded via the proteasomal pathway.

Three subtypes are known for PHDs, namely PHD1, PHD2 and PHD3. AKB-4924 is known as a PHD2 inhibitor. It is reported that AKB-4924 stabilizes HIF-1α in large intestine tissue (Non-patent literature 1). Furthermore, AKB-4924 has an improvement effect in a trinitrobenzene sulfonic acid (TNBS)-induced colitis model.

In contrast, PHD inhibitors, such as Roxadustat and Daprodustat, have a hematopoietic effect and have been developed as a therapeutic agent for anemia (Non-patent literature 2). Thus, it is important to avoid systemic effects such as a hematopoietic effect when a PHD inhibitor is used as a therapeutic agent for IBD.

For example, spiro compounds are described in Patent literatures 1 and 5, and Non-patent literatures 3 and 4 as PHD inhibitor. Compounds including imidazopyridinone are described or illustrated in Patent literatures 2 to 4.

However, the imidazopyridinone compounds of the present invention are neither described nor suggested in the above literatures.

CITATION LIST

Patent Literature

Patent literature 1: U.S. Published Application No. 2011/0152304
Patent literature 2: WO 2009/029609
Patent literature 3: WO 2003/037890
Patent literature 4: WO 2017/066014
Patent literature 5: U.S. Published Application No. 2010/0137297

Non-Patent Literature

Non-patent literature 1: Ellen Marks et al., "Inflamm. Bowel. Dis." 2015, Vol. 21, No. 2, pp. 267-275
Non-patent literature 2: Mun Chiang Chan et al., "Molecular Aspects of Medicine" 2016, Vol. 47-48, pp. 54-75
Non-patent literature 3: Guanghui Deng et al., "Bioorganic & Medicinal Chemistry", 2013, Vol. 21, pp. 6349-6358
Non-patent literature 4: Petr Vachal et al., "Journal of Medicinal Chemistry", 2012, Vol. 55, pp. 2945-2959

SUMMARY OF INVENTION

Problems to be Solved by the Invention

The present invention aims to provide a novel compound which has a PHD2 inhibitory effect and which is useful for the treatment of an inflammatory bowel disease.

Means for Solving the Problems

The present invention relates to a compound represented by the following formula (I) or a pharmaceutically acceptable salt thereof. That is, the present invention relates to the following [1] to [16] and the like.

[1] A compound represented by the formula (I):

[Chem. 1]

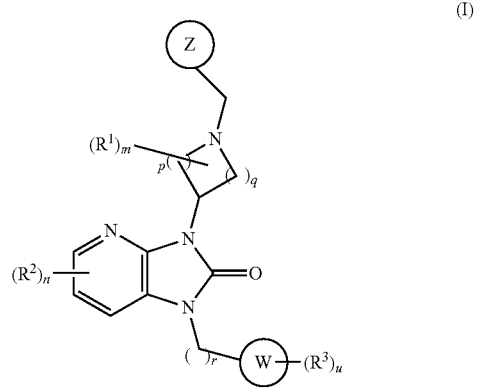

(I)

wherein
ring W is $C_{6-10}$ aryl, 5- or 6-membered heteroaryl, 9- or 10-membered heteroaryl, $C_{3-8}$ cycloalkyl or 3- to 8-membered heterocycloalkyl;

ring Z is a group selected from the group consisting of following (a) to (c):

[Chem. 2]

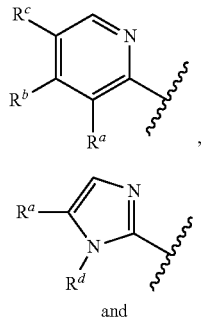

and

[Chem. 3]

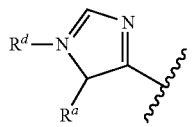

wherein
- $R^a$, $R^b$ and $R^c$ are each independently a hydrogen atom, a halogen atom, $C_{1-6}$ alkyl, cyano, hydroxy or carboxy; and
- $R^d$ is a hydrogen atom or $C_{1-6}$ alkyl;
- $R^1$ is a hydrogen atom, a halogen atom, $C_{1-6}$ alkyl, cyano, hydroxy or carboxy, wherein when m is 2 or 3, two or more $R^1$s may be different from each other;
- $R^2$ is a hydrogen atom, a halogen atom, $C_{1-6}$ alkyl, halo $C_{1-6}$ alkyl, $C_{1-6}$ alkoxy, hydroxy, —$CO_2R^4$ or —$CONR^5R^{5'}$, wherein when n is 2 or 3, two or more $R^2$s may be different from each other;
- $R^4$ is a hydrogen atom or $C_{1-6}$ alkyl; and
- $R^5$ and $R^{5'}$ are each independently a hydrogen atom, $C_{1-6}$ alkyl, carboxy $C_{1-6}$ alkyl, hydroxy $C_{1-6}$ alkyl, halo $C_{1-6}$ alkyl, $C_{3-8}$ cycloalkyl or 3- to 8-membered heterocycloalkyl;
- $R^3$ is a hydrogen atom, a halogen atom, $C_{1-6}$ alkyl, halo $C_{1-6}$ alkyl, $C_{1-6}$ alkoxy, halo $C_{1-6}$ alkoxy, $C_{2-6}$ alkenyl, $C_{2-6}$ alkynyl, $C_{1-6}$ alkylsulfanyl, $C_{1-6}$ alkylsulfinyl, $C_{1-6}$ alkylsulfonyl, hydroxy, cyano, nitro, —$NR^6R^{6'}$, —$CO_2R^7$, —$CONR^8R^{8'}$ or the following group A, wherein when u is 2 or 3, two or more $R^3$s may be different from each other;
- $R^6$ and $R^{6'}$ are each independently a hydrogen atom or $C_{1-6}$ alkyl;
- $R^7$ is a hydrogen atom or $C_{1-6}$ alkyl;
- $R^8$ and $R^{8'}$ are each independently a hydrogen atom, $C_{1-6}$ alkyl, carboxy $C_{1-6}$ alkyl, hydroxy $C_{1-6}$ alkyl, halo $C_{1-6}$ alkyl, $C_{3-8}$ cycloalkyl or 3- to 8-membered heterocycloalkyl;
- group A is a group selected from the group consisting of following (a) to (h):
  - (a) $C_{6-10}$ aryl which is unsubstituted or substituted with 1 to 3 groups selected from substituent group B,
  - (b) 5- or 6-membered heteroaryl which is unsubstituted or substituted with 1 to 3 groups selected from substituent group B,
  - (c) $C_{6-10}$ aryl $C_{1-6}$ alkyl which is unsubstituted or substituted with 1 to 3 groups selected from substituent group B,
  - (d) $C_{6-10}$ aryloxy which is unsubstituted or substituted with 1 to 3 groups selected from substituent group B,
  - (e) 5- or 6-membered heteroaryl $C_{1-6}$ alkyl which is unsubstituted or substituted with 1 to 3 groups selected from substituent group B,
  - (f) 5- or 6-membered heteroaryloxy which is unsubstituted or substituted with 1 to 3 groups selected from substituent group B,
  - (g) $C_{3-8}$ cycloalkyl which is unsubstituted or substituted with 1 to 3 groups selected from substituent group B, and
  - (h) 3- to 8-membered heterocycloalkyl which is unsubstituted or substituted with 1 to 3 groups selected from substituent group B,
- wherein substituent group B is a group consisting of a halogen atom, $C_{1-6}$ alkyl, halo $C_{1-6}$ alkyl, $C_{1-6}$ alkoxy, halo $C_{1-6}$ alkoxy, hydroxy, cyano, —$NR^9R^{9'}$, —$NR^9SO_2R^{10}$, —$CO_2R^{10}$ and —$CONR^{11}R^{11'}$;
- wherein $R^9$ and $R^{9'}$ are each independently a hydrogen atom or $C_{1-6}$ alkyl;
- $R^{10}$ is a hydrogen atom or $C_{1-6}$ alkyl; and
- $R^{11}$ and $R^{11'}$ are each independently a hydrogen atom, $C_{1-6}$ alkyl, carboxy $C_{1-6}$ alkyl, hydroxy $C_{1-6}$ alkyl, halo $C_{1-6}$ alkyl, $C_{3-8}$ cycloalkyl or 3- to 8-membered heterocycloalkyl;
- m, n and u are each independently an integer number 1 to 3;
- p and q are each independently 1 or 2; and
- r is an integer number 0 to 6;

or a pharmaceutically acceptable salt thereof.

[2] The compound according to the above [1], wherein ring Z is a group selected from the group consisting of following (a) to (j):

[Chem. 4]

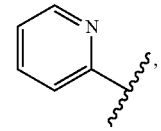

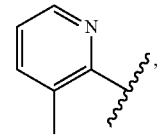

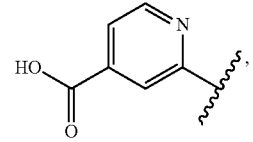

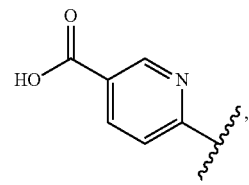

-continued

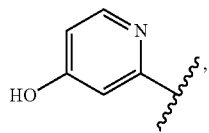 (e)

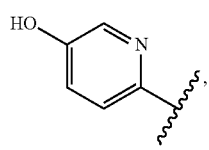 (f)

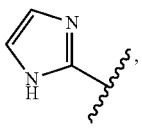 (g)

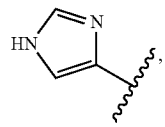 (h)

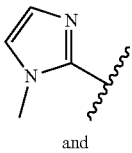 (i)

and

[Chem. 5]

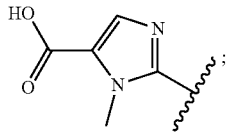 (j)

or a pharmaceutically acceptable salt thereof.

[3] The compound according to the above [1] or [2] or a pharmaceutically acceptable salt thereof, wherein ring W is phenyl or 5- or 6-membered heteroaryl.

[4] The compound according to any one of the above [1] to [3] or a pharmaceutically acceptable salt thereof, wherein r is 0.

[5] The compound according to any one of the above [1] to [4] or a pharmaceutically acceptable salt thereof, wherein p is 2, and q is 1.

[6] The compound according to any one of the above [1] to [5] or a pharmaceutically acceptable salt thereof, wherein $R^1$ is a hydrogen atom or a halogen atom.

[7] The compound according to any one of the above [1] to [6]:
wherein $R^2$ is a hydrogen atom, $C_{1-6}$ alkyl, halo $C_{1-6}$ alkyl, $C_{1-6}$ alkoxy, carboxy or —$CONR^5R^{5'}$;
wherein $R^5$ and $R^{5'}$ are each independently a hydrogen atom, carboxy $C_{1-6}$ alkyl or 3- to 8-membered heterocycloalkyl;
or a pharmaceutically acceptable salt thereof.

[8] The compound according to any one of the above [1] to [7]:
wherein $R^3$ is a hydrogen atom, a halogen atom, $C_{1-6}$ alkyl, halo $C_{1-6}$ alkyl, $C_{1-6}$ alkoxy, halo $C_{1-6}$ alkoxy, $C_{2-6}$ alkenyl, $C_{1-6}$ alkylsulfanyl, $C_{1-6}$ alkylsulfonyl, hydroxy, cyano, —$CO_2R^7$, —$CONR^8R^{8'}$ or group A;
wherein $R^7$ and u have the same meanings as those described in the above [1];
$R^8$ and $R^{8'}$ are each independently a hydrogen atom or carboxy $C_{1-6}$ alkyl; and group A is phenyl which is unsubstituted or substituted with 1 to 3 groups selected from substituent group B or unsubstituted 5- or 6-membered heteroaryl;
wherein substituent group B is a halogen atom, $C_{1-6}$ alkyl, halo $C_{1-6}$ alkyl, $C_{1-6}$ alkoxy, halo $C_{1-6}$ alkoxy, hydroxy, cyano or carboxy;
or a pharmaceutically acceptable salt thereof.

[9] The compound according to any one of the above [3] to [8], wherein ring Z is a group selected from the group consisting of following (a) to (e):

[Chem. 6]

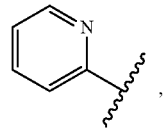 (a)

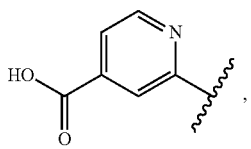 (b)

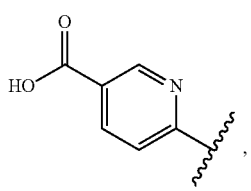 (c)

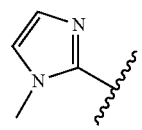 (d)

and

[Chem. 7]

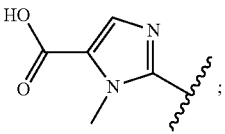 (e)

or a pharmaceutically acceptable salt thereof.

[10] A compound represented by the following formula:

[Chem. 8]

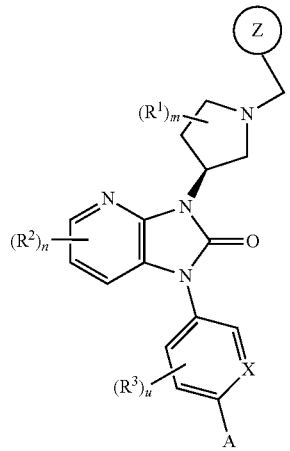

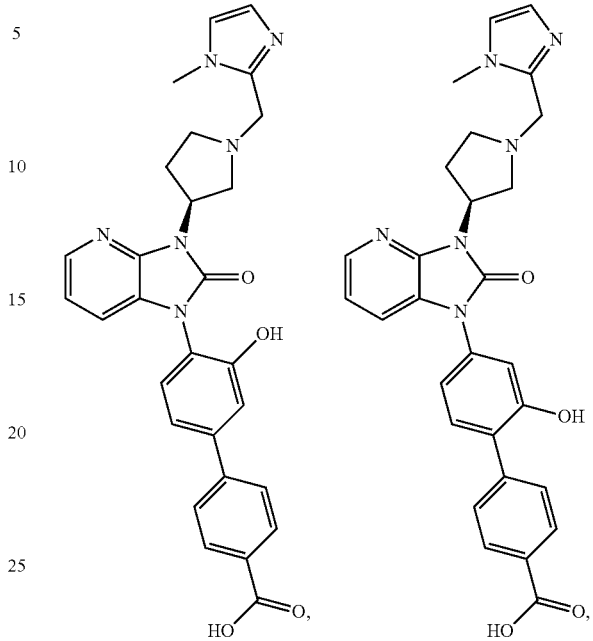

wherein
X is $CR^3$ or N;
u is 1 or 2;
$R^1$ has the same meanings as those described in the above [6];
$R^2$ has the same meanings as those described in the above [7];
$R^3$ is a hydrogen atom, $C_{1-6}$ alkyl or hydroxy;
group A has the same meanings as those described in the above [8];
ring Z has the same meaning as those described in the above [9]; and
m and n have the same meanings as those described in the above [1];
or a pharmaceutically acceptable salt thereof.

[11] The compound according to the above [1]:
wherein u is 2 or 3;
one $R^3$ is group A; and
the other $R^3$s are each independently a hydrogen atom, a halogen atom, $C_{1-6}$ alkyl, halo $C_{1-6}$ alkyl, $C_{1-6}$ alkoxy, halo $C_{1-6}$ alkoxy, $C_{2-6}$ alkenyl, $C_{1-6}$ alkylsulfanyl, $C_{1-6}$ alkylsulfonyl, hydroxy, cyano, nitro, $-NR^6R^{6'}$, $-CO_2R^7$ or $-CONR^8R^{8'}$;
wherein group A, $R^6$, $R^{6'}$, $R^7$, $R^8$ and $R^{8'}$ have the same meanings as those described in the above [1];
or a pharmaceutically acceptable salt thereof.

[12] The compound according to the above [1] which is selected from the group consisting of the following compounds:

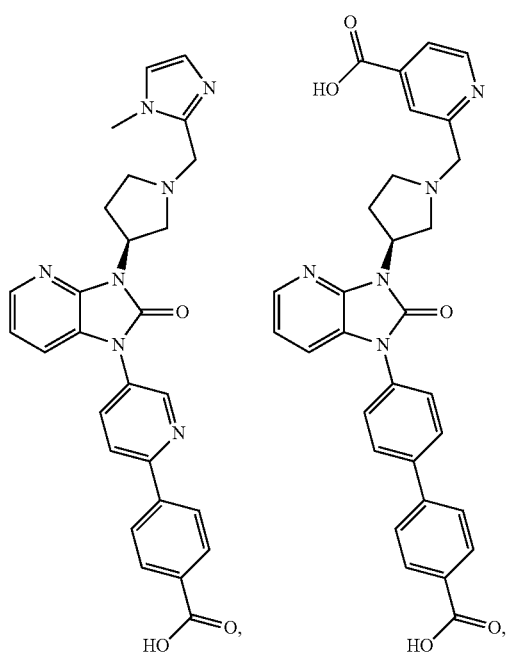

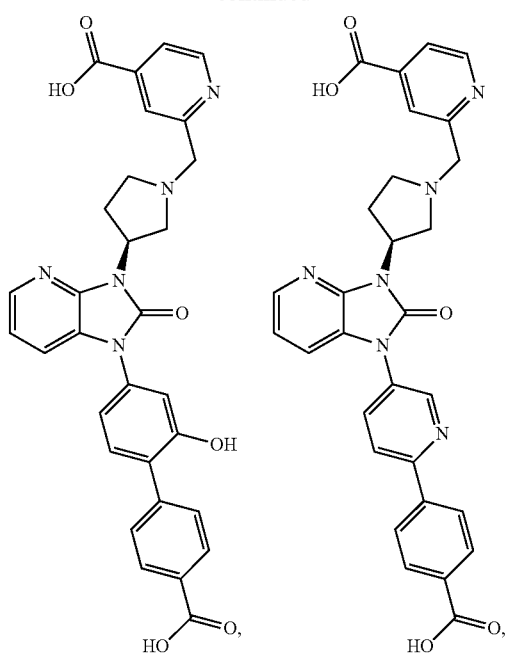
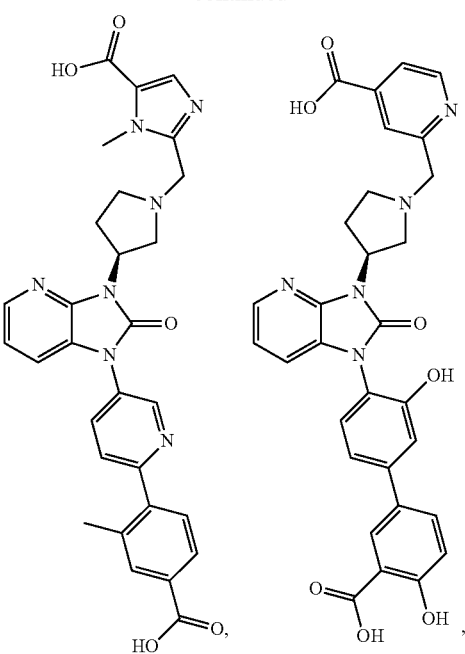
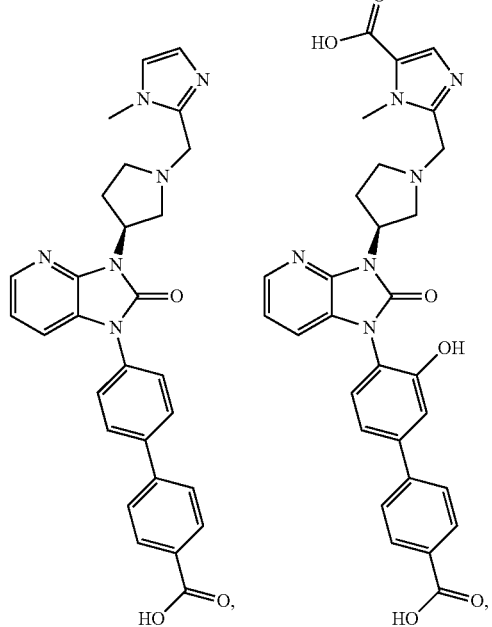
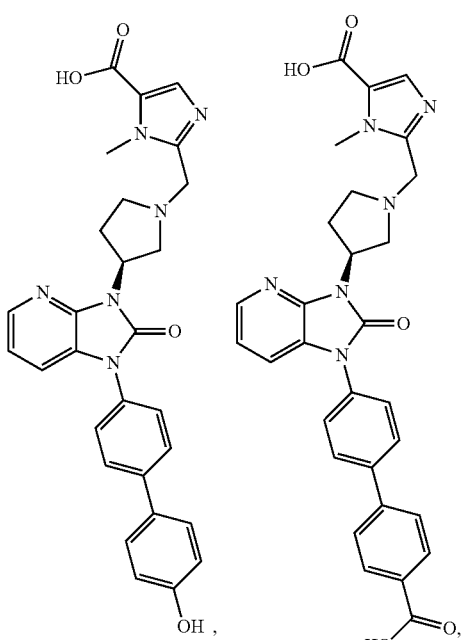
and

-continued

[Chem. 10]

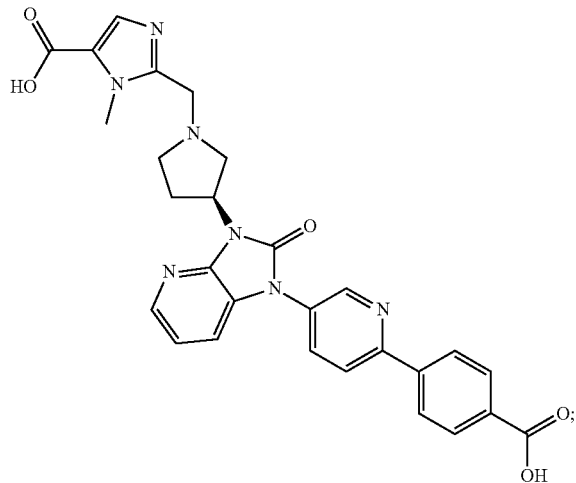

or a pharmaceutically acceptable salt thereof.

[13] The compound according to the above [1] which is represented by the following formula:

[Chem. 11]

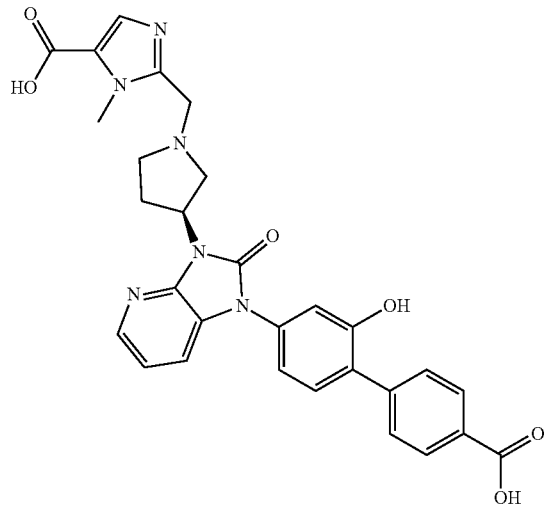

or a pharmaceutically acceptable salt thereof.

[14] A pharmaceutical composition comprising the compound according to any one of the above [1] to [13] or a pharmaceutically acceptable salt thereof, and pharmaceutical additive.

[15] The pharmaceutical composition according to the above [14] which is a pharmaceutical composition for use in the treatment of an inflammatory bowel disease.

[16] The pharmaceutical composition according to the above [15] wherein the inflammatory bowel disease is ulcerative colitis or Crohn's disease.

In an embodiment, the present invention relates to a method for treating an inflammatory bowel disease, comprising administering a necessary amount of the pharmaceutical composition according to the above [14] to a patient.

In an embodiment, the present invention relates to a use of the compound according to any one of the above [1] to [13] or a pharmaceutically acceptable salt thereof for manufacturing a pharmaceutical composition for use in the treatment of an inflammatory bowel disease.

Effect of the Invention

The compounds of the present invention have an excellent PHD2 inhibitory effect, and thus the compounds of the present invention or pharmaceutically acceptable salts thereof are useful as agents for the treatment of an inflammatory bowel disease.

MODE FOR CARRYING OUT THE INVENTION

Hereinafter, embodiments of the present invention are described in more detail.

In the present invention, each term has the following meanings unless otherwise specified.

The term "halogen atom" means a fluorine atom, a chlorine atom, a bromine atom or an iodine atom. As $R^1$, $R^2$ and $R^3$, a fluorine atom is preferable.

The term "$C_{1-6}$ alkyl" means a straight-chained or branched alkyl group having 1 to 6 carbon atoms. For example, methyl, ethyl, propyl, isopropyl, butyl, isobutyl, sec-butyl, tert-butyl and the like can be illustrated.

The term "$C_{2-6}$ alkenyl" means a straight-chained or branched alkenyl group having 2 to 6 carbon atoms. For example, vinyl, allyl, 1-propenyl, isopropenyl and the like can be illustrated.

The term "$C_{2-6}$ alkynyl" means a straight-chained or branched alkynyl group having 2 to 6 carbon atoms. For example, ethynyl, 2-propynyl and the like can be illustrated.

The term "$C_{1-6}$ alkoxy" means a straight-chained or branched alkoxy group having 1 to 6 carbon atoms. For example, methoxy, ethoxy, propoxy, isopropoxy and the like can be illustrated.

The term "carboxy $C_{1-6}$ alkyl" means $C_{1-6}$ alkyl substituted with one carboxy. For example, carboxymethyl and the like can be illustrated.

The term "hydroxy $C_{1-6}$ alkyl" means $C_{1-6}$ alkyl substituted with one hydroxy. For example, hydroxymethyl, 1-hydroxyethyl, 1-hydroxy-1,1-dimethylmethyl, 2-hydroxyethyl, 2-hydroxy-2-methylpropyl, 3-hydroxypropyl and the like can be illustrated.

The term "halo $C_{1-6}$ alkyl" means $C_{1-6}$ alkyl substituted with 1 to 3 same or different halogen atoms. For example, monofluoromethyl, 2-fluoroethyl, difluoromethyl, trifluoromethyl, 2,2,2-trifluoroethyl, 3,3,3-trifluoropropyl, 4,4,4-trifluorobutyl and the like can be illustrated.

The term "halo $C_{1-6}$ alkoxy" means $C_{1-6}$ alkoxy substituted with 1 to 3 same or different halogen atoms. For example, monofluoromethoxy, difluoromethoxy, trifluoromethoxy and the like can be illustrated.

The term "$C_{1-6}$ alkylsulfanyl" means a group represented by ($C_{1-6}$ alkyl)-S—.

The term "$C_{1-6}$ alkylsulfinyl" means a group represented by ($C_{1-6}$ alkyl)-S(=O)—.

The term "$C_{1-6}$ alkylsulfonyl" means a group represented by ($C_{1-6}$ alkyl)-SO$_2$—. For example, methylsulfonyl, ethylsulfonyl and the like can be illustrated.

The term "$C_{6-10}$ aryl" means phenyl or naphthyl. As group A, phenyl is preferable.

The term "5- or 6-membered heteroaryl" means a 5- or 6-membered aromatic heterocyclic group having any 1 to 4 hetero atoms selected from an oxygen atom, a nitrogen atom and a sulfur atom in the ring. For example, furyl, pyrrolyl, thienyl, imidazolyl, pyrazolyl, 1,2,4-triazolyl, isothiazolyl, isoxazolyl, oxazolyl, thiazolyl, 1,3,4-oxadiazolyl, 1,2,4-oxadiazolyl pyridyl, pyrimidyl, pyrazinyl, pyridazinyl, and the like can be illustrated. As ring W, thienyl, pyridyl and the like are preferable, and pyridyl is more preferable. As group A, pyridyl and the like are preferable.

The term "9- or 10-membered heteroaryl" means a bicyclic aromatic heterocyclic group having any 1 to 4 hetero atoms selected from an oxygen atom, a nitrogen atom and a sulfur atom in the ring. For example, indolyl, isoindolyl, benzofuryl, benzothiophenyl, benzoimidazolyl, purinyl, benzotriazolyl, quinolyl, isoquinolyl, quinazolyl, quinoxalyl, cinnolyl, pteridinyl, chromenyl, isochromenyl and the like can be illustrated. As ring W, quinolyl and the like are preferable.

The term "$C_{3-8}$ cycloalkyl" means a 3- to 8-membered saturated hydrocarbon group. For example, cyclopropyl, cyclobutyl, cyclopentyl, cyclohexyl and the like can be illustrated.

The term "3- to 8-membered heterocycloalkyl" means a 3- to 8-membered heterocycloalkyl group having any 1 or 2 hetero atoms selected from an oxygen atom, a nitrogen atom and a sulfur atom in the ring. For example, aziridino, azetidino, morpholino, thiomorpholino, 1-pyrrolidinyl, piperidino, 4-piperidinyl, 1-piperazinyl, 1-pyrrolyl, tetrahydrofuranyl, tetrahydropyranyl and the like can be illustrated. As $R^5$ and $R^{5'}$, tetrahydropyranyl and the like are preferable.

The term "$C_{6-10}$ aryl $C_{1-6}$ alkyl" means $C_{1-6}$ alkyl substituted with one $C_{6-10}$ aryl. For example, benzyl can be illustrated.

The term "$C_{6-10}$ aryloxy" means a group represented by ($C_{6-10}$ aryl)-O—. For example, phenoxy can be illustrated.

The term "5- or 6-membered heteroaryl $C_{1-6}$ alkyl" means $C_{1-6}$ alkyl substituted with one 5- or 6-membered heteroaryl.

The term "5- or 6-membered heteroaryloxy" means a group represented by (5- or 6-membered heteroaryl)-O—.

When a group is substituted with 2 or 3 groups selected from substituent group B, these groups may be the same or different from each other.

The following abbreviations in the description, figures and tables have the following meanings, respectively.

CDI: carbonyldiimidazole
CPME: cyclopentyl methyl ether
DEAD: diethyl azodicarboxylate
DIPEA: N,N-diisopropylethylamine
DMA: N,N-dimethylacetamide
DMAP: 4-dimethylaminopyridine
DMF: N,N-dimethylformamide
DMSO: dimethylsulfoxide
DMTMM: 4-(4,6-dimethoxy-1,3,5-triazin-2-yl)-4-methylmorpholinium chloride EDC-HCl: 1-(3-dimethylaminopropyl)-3-ethylcarbodiimide hydrochloride
HOBt: 1-hydroxybenzotriazole
HOBt-H$_2$O: 1-hydroxybenzotriazole monohydrate
LAH: lithium aluminium hydride
LDA: lithium diisopropylamide
NaBH(OAc)$_3$: sodium triacetoxyborohydride
NMP: 1-methyl-2-pyrrolidinone
Pd(amphos)Cl$_2$: bis[di-tert-butyl(4-dimethylaminophenyl)phosphine]dichloropalladium (II)
THF: tetrahydrofuran
TsCl: p-toluenesulfonyl chloride
T3P (registered trademark): propylphosphonic acid anhydride (cyclic trimer)
9-BBN: 9-borabicyclo[3.3.1]nonane amino-silica gel: aminopropylated silica gel
ODS column chromatography: octadecyl-silylated silica gel column chromatography
Process: process
Scheme: scheme
Ref. No.: Reference Example Number
Ex. No.: Example Number
Structure: structural formula
Physical data: physical data
IC$_{50}$: concentration required for 50% inhibition
(Numerals with "*" in the tables mean the inhibition rates at the compound concentration of 100 μM.)
FITC: Fluorescein isothiocyanate
$^1$H-NMR: hydrogen nuclear magnetic resonance spectrum
DMSO-d6: dimethylsulfoxide-d6
CDCl$_3$: chloroform-d1
MS: mass spectrometry
ESI_APCI: multiionization using electrospray ionization-atmospheric pressure chemical ionization In an embodiment, the compound represented by the formula (I) is, for example, a compound represented by the following formula. In the formula, $R^{3'}$ has the same meanings as those of $R^3$ in the above [1], with the proviso that $R^{3'}$ is not group A. The other symbols have the same meanings as those described in the above [1].

[Chem. 12]

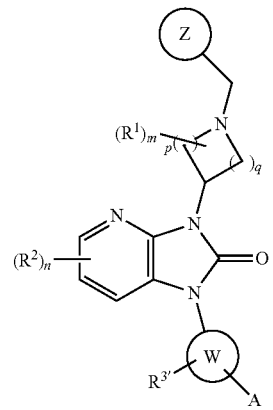

In an embodiment, the compound represented by the formula (I) is a compound, wherein the group represented by the following formula is a group selected from the group consisting of following (a) to (d).

[Chem. 13]

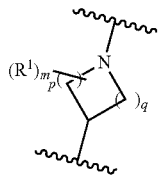

The symbols in the formula have the same meanings as those described in the above [1].

[Chem. 14]

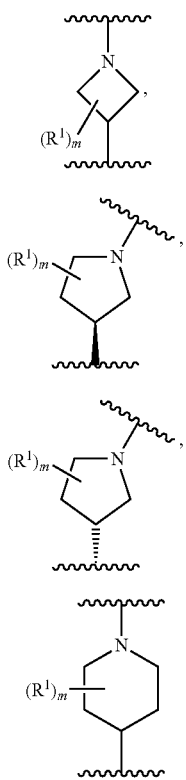

In an embodiment, the compound represented by the formula (I) is preferably the compound according to the above [1], wherein the groups are groups selected from the groups consisting of following [A] to [I] or any combination thereof.

[A] ring W is phenyl, naphthyl, thienyl, pyridyl, quinolyl or cyclohexyl.
[B] $R^a$, $R^b$ and $R^c$ are each independently a hydrogen atom, a halogen atom, methyl, cyano, hydroxy or carboxy.
[C] $R^d$ is a hydrogen atom or methyl.
[D] $R^1$ is a hydrogen atom, a halogen atom or methyl.
[E] $R^2$ is a hydrogen atom, methyl, trifluoromethyl, methoxy, —$CO_2H$ or —$CONR^5R^{5'}$;
wherein $R^5$ and $R^{5'}$ are each independently a hydrogen atom, carboxymethyl or tetrahydropyranyl.
[F] $R^3$ is a hydrogen atom, a halogen atom, methyl, trifluoromethyl, methoxy, trifluoromethoxy, vinyl, methylthio, ethylsulfony, hydroxy, cyano, nitro, dimethylamino, —$CO_2R^7$, —$CONR^8R^{8'}$ or group A, wherein when u is 2, two $R^3$s may be different from each other;
group A is a group selected from the group consisting of following (a) to (f):
(a) phenyl which is unsubstituted or substituted with 1 or 2 groups selected from substituent group B,
(b) pyridyl,
(c) benzyl,
(d) phenyloxy,
(e) cyclopropyl and
(f) morpholino;
wherein substituent group B is a group consisting of a halogen atom, methyl, trifluoromethyl, methoxy, trifluoromethoxy, hydroxy, cyano, —$NHSO_2R^{10}$ and —$CO_2R^{10'}$;

wherein $R^{10}$ and $R^{10'}$ are each independently a hydrogen atom or methyl;
$R^7$ is a hydrogen atom or methyl; and
$R^8$ and $R^{8'}$ are each independently a hydrogen atom or carboxymethyl.
[G] m, n and u are each independently 1 or 2.
[H] p and q are each independently 1 or 2.
[I] r is 0 or 1.

In the case where the compounds represented by the formula (I) contain one or more asymmetric carbon atoms, stereoisomers in the R- or S-configuration at each of the asymmetric carbon atoms and mixtures of any combinations thereof are included in the present invention. In such cases, racemic compounds, racemic mixtures, individual enantiomers and mixtures of diastereomers are also included in the scope of the present invention.

In the case where the compounds represented by the formula (I) have the cis-trans isomers, all the cis-trans isomers are included in the present invention.

In the case where tautomers of the compounds represented by the formula (I) exist, the present invention includes all the tautomers.

In the present invention, stereochemical determination can also be conducted according to well-known methods in the art.

A compound represented by the formula (I) can also be converted into pharmaceutically acceptable salts thereof according to a general method, if necessary. As such salts, an acid addition salt and a salt with a base can be illustrated.

As the acid addition salt, an acid addition salt with a mineral acid such as hydrochloric acid, hydrobromic acid, hydroiodic acid, sulfuric acid, nitric acid, and phosphoric acid and an acid addition salt with an organic acid such as formic acid, acetic acid, trifluoroacetic acid, methanesulfonic acid, benzenesulfonic acid, p-toluenesulfonic acid, propionic acid, citric acid, succinic acid, tartaric acid, fumaric acid, butyric acid, oxalic acid, malonic acid, maleic acid, lactic acid, malic acid, carbonic acid, benzoic acid, glutamic acid and aspartic acid can be illustrated.

As the salt with a base, a salt formed with an inorganic base such as lithium, sodium, potassium, calcium and magnesium, and a salt formed with an organic base such as N-methyl-D-glucamine, N,N'-dibenzylethylenediamine, triethylamine, piperidine, morpholine, pyrrolidine, arginine, lysine and choline can be illustrated.

In the case where a compound represented by the formula (I) or a pharmaceutically acceptable salt thereof exists, for example, as crystal, the present invention includes all the crystalline forms. For example, a pharmaceutically acceptable salt also includes a solvate thereof with a pharmaceutically acceptable solvent such as water or ethanol, a cocrystal thereof with an appropriate cocrystal former (coformer) and the like.

In the compounds represented by the formula (I), part of the atoms may be replaced with corresponding isotopes. The present invention includes compounds in which atoms are replaced with these isotopes. Examples of the isotopes include isotopes of a hydrogen atom, a carbon atom, a chlorine atom, a fluorine atom, an iodine atom, a nitrogen atom, an oxygen atom, a phosphorus atom and a sulfur atom represented by $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$ and $^{35}S$. In an embodiment, a compound represented by the formula (I) in which part of the hydrogen atoms are replaced with $^2H$ (D: deuterium atom) can be illustrated.

The compounds represented by the formula (I) in which part of the atoms are replaced with isotopes can be prepared by a similar method to the method for manufacturing described below using a commercial isotope-introduced building block. For example, a compound represented by the formula (I) in which part of the hydrogen atoms are replaced with deuterium atoms can also be prepared by the above method and a method described in literatures (see, for example, Yukigosei-kagaku kyokaishi, Vol. 65, No. 12, pp. 1179-1190, 2007). For example, a compound represented by the formula (I) in which part of the carbon atoms are replaced with $^{13}C$ can also be prepared by the above method and a method described in literatures (see, for example, RADIOISOTOPES 2007, Vol. 56, No. 11, pp. 35-44).

A compound represented by the formula (I) can be prepared, for example, by a method described in Schemes 1 to 5, a similar method thereto, a method described in literatures or a similar method thereto.

For reaction in each process, commercial products can be used when the starting materials and the reagents are commercially available.

For reaction in each process, the reaction time is usually from 30 minutes to 3 days, varying with the used starting material, solvent, reaction temperature or the like, unless otherwise specified.

For reaction in each process, the reaction temperature is usually at −78° C. to reflux temperature, varying with the used starting material, solvent or the like, unless otherwise specified.

For reaction in each process, the pressure is usually at 1 atm. to 20 atm., varying with the used starting material, solvent, reaction temperature or the like, unless otherwise specified.

For reaction in each process, a microwave reactor such as Biotage's Initiator can also be used. When the reaction is conducted using a microwave reactor, the reaction can be conducted at pressure range: 1 to 30 bar, power range: 1 to 400 W, reaction temperature: room temperature to 300° C., and reaction time: a minute to 1 day, varying with the used starting material, solvent, model or the like.

For reaction in each process, the reactions is conducted without any solvent or using an appropriate solvent unless otherwise specified. As an example of the appropriate solvent, a solvent which is inert to the reaction can be illustrated. As specific examples of the solvent, the solvents which are described in the Reference Examples or the Examples corresponding to each process or the following solvents can be illustrated:
  alcohols: methanol, ethanol, tert-butyl alcohol, 2-propanol and the like;
  ethers: diethyl ether, THF, 1,2-dimethoxy ethane, 1,4-dioxane, 2-methyloxolane, CPME and the like;
  aromatic hydrocarbons: chlorobenzene, 1,2-dichlorobenzene, toluene, xylene and the like;
  saturated hydrocarbons: cyclohexane, n-hexane and the like;
  amides: DMF, DMA, NMP and the like;
  halogenated hydrocarbons: dichloromethane, 1,2-dichloroethane, carbontetrachloride and the like;
  nitriles: acetonitrile and the like;
  sulfoxides: dimethylsulfoxide and the like;
  aromatic organic bases: pyridine and the like;
  acid anhydrides: acetic anhydride and the like;
  organic acids: formic acid, acetic acid, trifluoroacetic acid and the like;
  esters: ethyl acetate, methyl acetate, isopropyl acetate and the like;
  ketones: acetone, methyl ethyl ketone and the like; and
  water.

The above solvents may be used as a mixture of two or more thereof at an appropriate ratio.

When a base is used for reaction in each process, the reaction is conducted using an appropriate base for the reaction. As specific examples of the base, the bases which are described in the Reference Examples or the Examples corresponding to each process or the following bases can be illustrated:
  inorganic bases: sodium hydroxide, lithium hydroxide, potassium hydroxide, sodium carbonate, sodium bicarbonate, potassium carbonate, cesium carbonate and the like; organic bases: triethylamine, DIPEA, diethylamine, pyridine, DMAP, 2,6-lutidine, piperidine and the like;
  metal alkoxides: sodium ethoxide, sodium methoxide, potassium tert-butoxide and the like;
  alkali metal hydrides: sodium hydride and the like;
  metal amides: sodium amide, LDA, lithium bis(trimethylsilyl)amide, sodium bis(trimethylsilyl)amide, potassium bis(trimethylsilyl)amide and the like;
  organic magnesiums: methylmagnesium bromide, isopropylmagnesium chloride, allylmagnesium bromide, phenylmagnesium bromide and the like; and
  organic lithiums: n-butyllithium, sec-butyllithium, tert-butyllithium and the like.

When an acid or an acidic catalyst is used for reaction in each process, the reaction is conducted using an acid or an acid catalyst which is appropriate for the reaction. As specific examples of the acid or the acidic catalyst, the acids or the acidic catalysts which are described in the Reference Examples or the Examples corresponding to each process or the following acids or acidic catalysts can be illustrated:
  inorganic acids: hydrochloric acid, sulfuric acid, nitric acid, hydrobromic acid, phosphoric acid and the like;
  organic acids: acetic acid, trifluoroacetic acid, citric acid, p-toluenesulfonic acid, 10-camphorsulfonic acid and the like; and
  Lewis acid: boron trifluoride-diethyl ether complex, zinc iodide, aluminum chloride, zinc chloride, titanium (IV) chloride and the like.

When a condensing reagent is used for reaction in each process, the reaction is conducted using an appropriate condensing reagent for the reaction. As specific examples of the condensing reagent, the condensing reagents which are described in the Reference Examples or the Examples corresponding to each process or the following condensing reagents can be illustrated:
  carbodiimides: EDC-HCl, N,N'-dicyclohexylcarbodiimide and the like;
  carbonyldiimidazoles: CDI and the like;
  uronium and phosphonium salts: O-(7-azabenzotriazol-1-yl)-N,N,N',N'-tetramethyluronium hexafluorophosphate, 1H-benzotriazol-1-yloxytris(dimethylamino) phosphonium hexafluorophosphate and the like;
  triazins: DMTMM and the like; and
  others: T3P and the like.

When a reducing reagent is used for reaction in each process, the reaction is conducted using an appropriate reducing reagent for the reaction. As specific examples of the reducing reagent, the reducing reagents which are described in the Reference Examples or the Examples corresponding to each process or the following reducing reagents can be illustrated: metal hydrides: LAH, lithium borohydride, sodium borohydride, $NaBH(OAc)_3$, sodium cyanoborohydride, diisobutylaluminum hydride and the like; and boranes: borane-tetrahydrofuran complex, 9-BBN, picoline borane and the like.

In each process, when a protective group is necessary based on the kind of a functional group, operations of introduction and removal can also be conducted optionally in combination according to a general method. Examples regarding the types of the protective groups, protection and deprotection include the methods described in Theodora W. Greene & Peter G. M. Wuts Eds., "Greene's Protective Groups in Organic Synthesis", fourth edition, Wiley-Interscience, 2006.

In each process, when removal of a protective group is conducted, the reaction can be conducted by hydrolysis reaction or the like.

In each process, when hydrolysis reaction is conducted, the reaction can be conducted in the presence of an acid or a base. As the acid and the base, the above-mentioned examples can be illustrated.

In each process, when catalytic reduction reaction is conducted, the reaction can be conducted under a hydrogen atmosphere in the presence of a catalyst. As the catalyst, palladium on carbon powder, platinum on carbon powder, Raney nickel and the like can be illustrated.

In each process, when reduction reaction is conducted, the reaction can be conducted in the presence of a reducing reagent. As the reducing reagent, the above-mentioned examples can be illustrated.

In each process, when amidation reaction is conducted, the reaction can be conducted in the presence of a condensing reagent and a base or in the presence of a condensing reagent. As the condensing reagent and the base, the above-mentioned examples can be illustrated. When a carbodiimide is used as the condensing reagent, an additive such as HOBt or DMAP may be added, if necessary. The amidation reaction may also be conducted using an acyl halide or an acid anhydride.

In each process, when reductive amination reaction is conducted, the reaction can be conducted in the presence of a reducing reagent. As the reducing reagent, the above-mentioned examples can be illustrated. As the reducing reagent, $NaBH(OAc)_3$ and the like can preferably be illustrated.

In each process, when aromatic nucleophilic substitution reaction is conducted, the reaction can be conducted in the presence of a base. As the base, the above-mentioned examples can be illustrated.

In each process, when intramolecular carbonylation reaction is conducted, the reaction can be conducted in the presence of a condensing reagent. As the condensing reagent, the above-mentioned examples can be illustrated.

In each process, when Ullmann condensation reaction is conducted, the reaction can be conducted in the presence of a copper catalyst, a ligand and a base. As the copper catalyst, copper iodide and the like can be illustrated. As the ligand, N,N'-dimethylethylenediamine and the like can be illustrated. As the base, the above-mentioned examples can be illustrated.

In each process, when Chan-Lam-Evans coupling reaction is conducted, the reaction can be conducted in the presence of a copper catalyst and a base. As the copper catalyst, copper (II) acetate and the like can be illustrated. As the base, the above-mentioned examples can be illustrated.

In each process, when Mitsunobu reaction is conducted, the reaction can be conducted in the presence of azodicarboxylic acid ester and phosphine. As the azodicarboxylic acid ester, DEAD and the like can be illustrated. As the phosphine, triphenylphosphine and the like can be illustrated.

In each process, when Suzuki-Miyaura cross coupling reaction is conducted, the reaction can be conducted in the presence of a palladium catalyst and a base. As the palladium catalyst, $Pd(amphos)Cl_2$ and the like can be illustrated. As the base, the above-mentioned examples can be illustrated.

In each process, the symbols in the formulae have the same meanings as those described in the above [1] unless otherwise specified. Y is a bromine atom, an iodine atom, boronic acid or hydroxy. Y' is a fluorine atom or a chlorine atom. Y'' is boronic acid or boronic acid ester. X is $CR^3$ or N.

A compound represented by the formula (I) can be prepared, for example, by the method described in Processes 1-1 to 1-3 in Scheme 1.

Scheme 1

[Chem. 15]

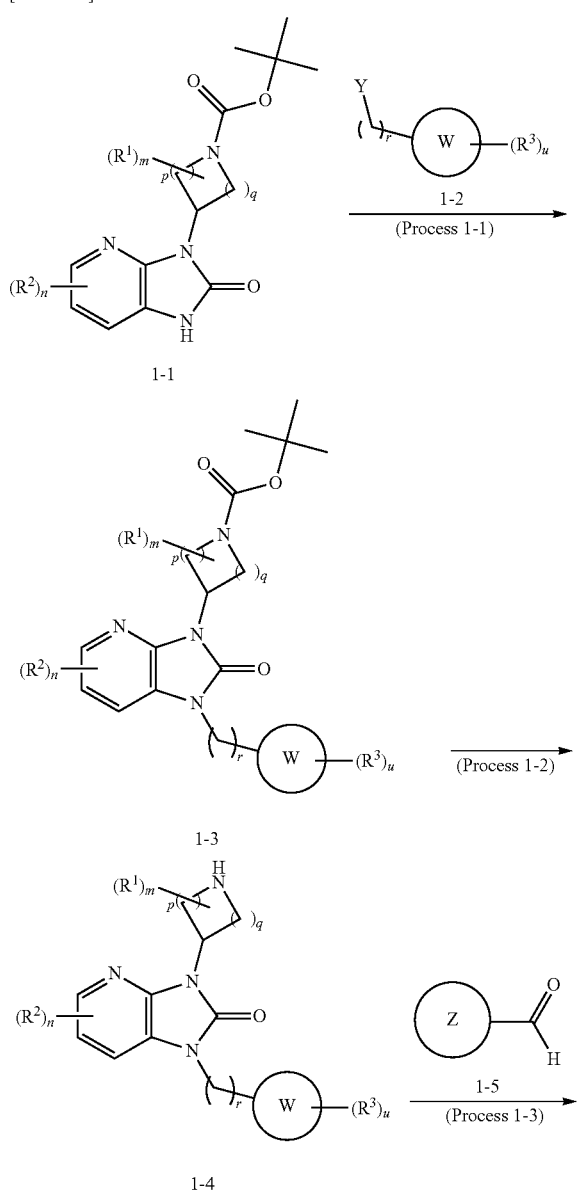

-continued

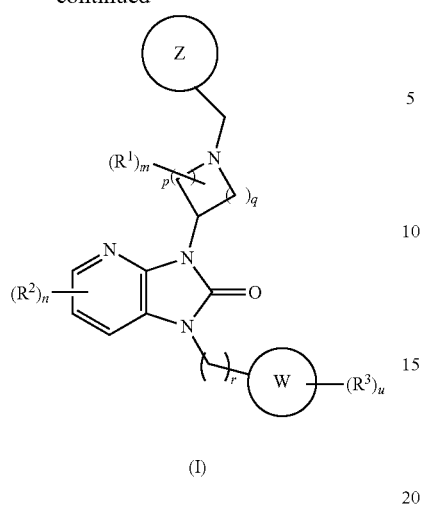

(I)

Process 1-1

Compound (1-3) can also be prepared by Ullmann condensation reaction, Chan-Lam-Evans coupling reaction or Mitsunobu reaction of Compound (1-1) and Compound (1-2).

When Y is a bromine atom or an iodine atom, r is 0, and W is aryl or heteroaryl, Ullmann condensation reaction is preferable. When Y is boronic acid, r is 0, and W is aryl or heteroaryl, Chan-Lam-Evans coupling reaction is preferable. When Y is hydroxy, r is 0, and W is cycloalkyl or heterocycloalkyl, Mitsunobu reaction is preferable. When Y is hydroxy and r is an integer number 1 to 6, Mitsunobu reaction is preferable.

Process 1-2

Compound (1-4) can also be prepared by removing a protective group of Compound (1-3).

Process 1-3

Compound (I) can also be prepared by reductive amination reaction of Compound (1-4) and Compound (1-5). Removal of a protective group can also be conducted, if necessary.

Compound (1-1) can be prepared, for example, by the method described in Processes 2-1 to 2-3 in Scheme 2.

Scheme 2

[Chem. 16]

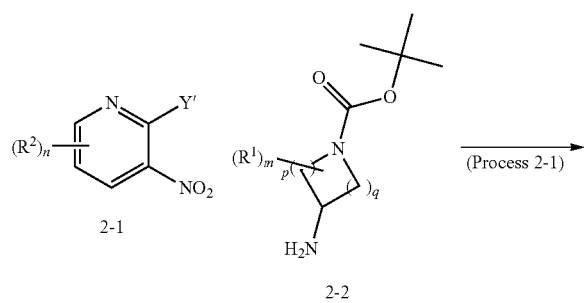

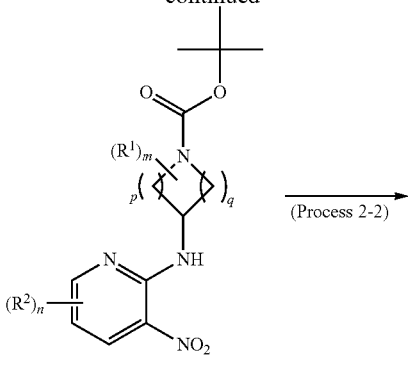

2-3

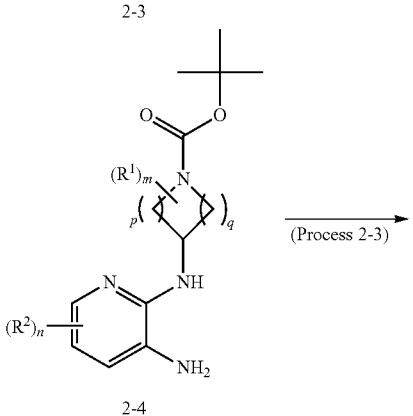

2-4

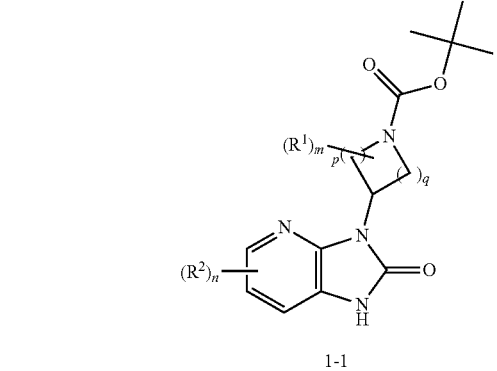

1-1

Process 2-1

Compound (2-3) can also be prepared by aromatic nucleophilic substitution reaction of Compound (2-1) and Compound (2-2).

Process 2-2

Compound (2-4) can also be prepared by catalytic reduction reaction of Compound (2-3).

Process 2-3

Compound (1-1) can also be prepared by intramolecular carbonylation reaction of Compound (2-4).

Compound (IA) can be prepared, for example, by the method described in Processes 3-1 to 3-4 in Scheme 3.

Scheme 3

[Chem. 17]

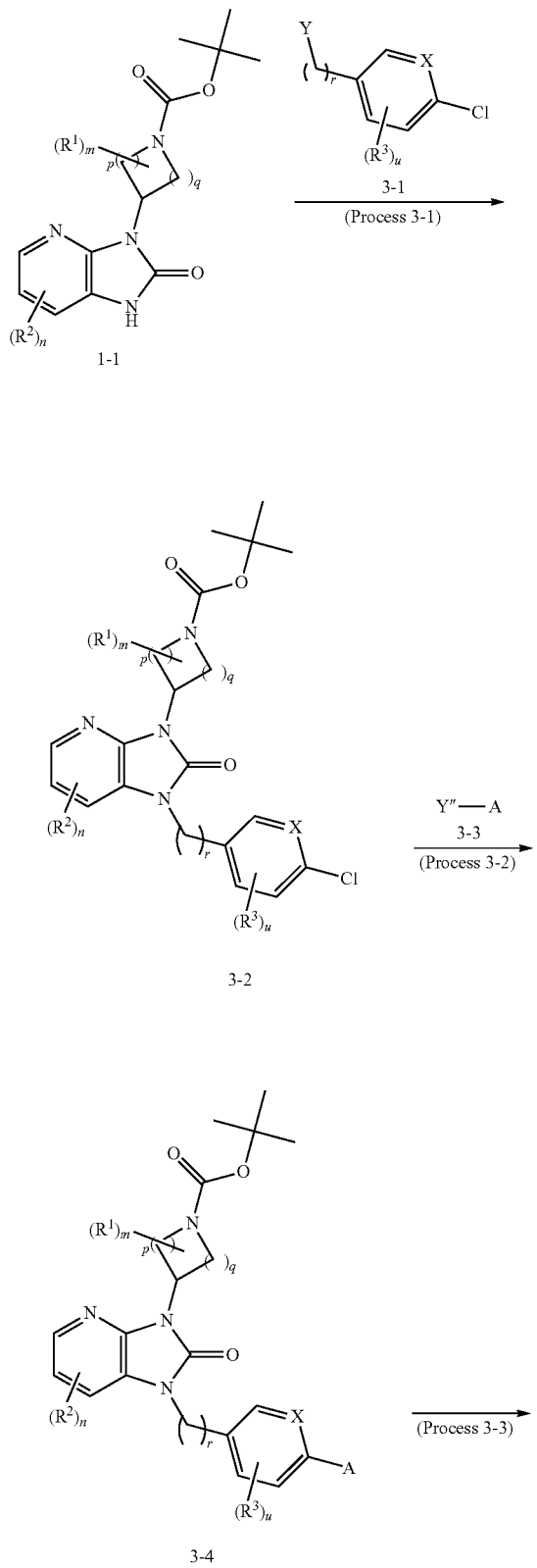

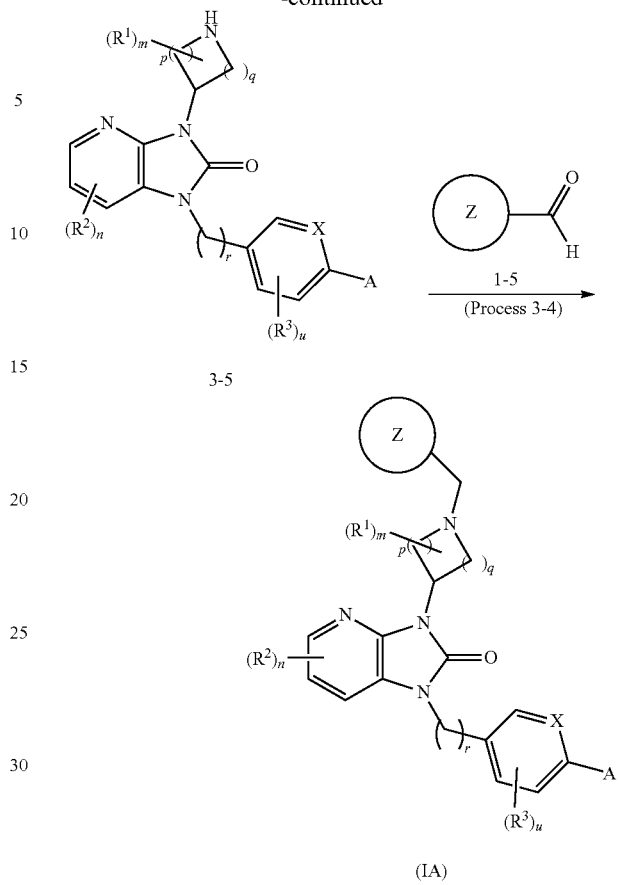

Process 3-1

Compound (3-2) can also be prepared by Ullmann condensation reaction, Chan-Lam-Evans coupling reaction or Mitsunobu reaction of Compound (1-1) and Compound (3-1).

When Y is a bromine atom or an iodine atom, and r is 0, Ullmann condensation reaction is preferable. When Y is boronic acid, and r is 0, Chan-Lam-Evans coupling reaction is preferable. When Y is hydroxy and r is an integer number 1 to 6, Mitsunobu reaction is preferable.

Process 3-2

Compound (3-4) can also be prepared by Suzuki-Miyaura cross coupling reaction of Compound (3-2) and Compound (3-3).

Process 3-3

Compound (3-5) can also be prepared by removing a protective group of Compound (3-4).

Process 3-4

Compound (IA) can also be prepared by reductive amination reaction of Compound (3-5) and Compound (1-5). Removal of a protective group can also be conducted, if necessary.

Compound (I) can be prepared, for example, by the method described in Processes 4-1 to 4-3 in Scheme 4.

Scheme 4

[Chem. 18]

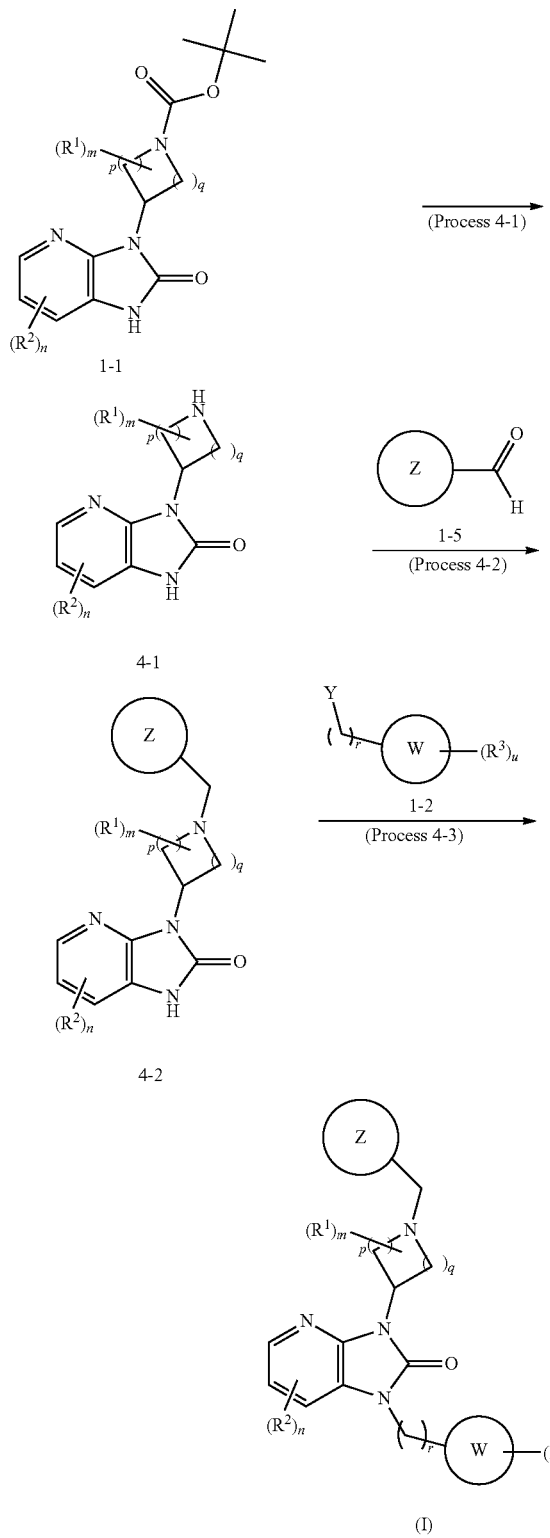

Process 4-1

Compound (4-1) can also be prepared by removing a protective group of Compound (1-1).

Process 4-2

Compound (4-2) can also be prepared by reductive amination reaction of Compound (4-1) and Compound (1-5).

Process 4-3

Compound (I) can also be prepared by Ullmann condensation reaction, Chan-Lam-Evans coupling reaction or Mitsunobu reaction of Compound (4-2) and Compound (1-2). Removal of a protective group can also be conducted, if necessary.

When Y is a bromine atom or an iodine atom, r is 0, and W is aryl or heteroaryl, Ullmann condensation reaction is preferable. When Y is boronic acid, r is 0, and W is aryl or heteroaryl, Chan-Lam-Evans coupling reaction is preferable. When Y is hydroxy, r is 0, and W is cycloalkyl or heterocycloalkyl, Mitsunobu reaction is preferable. When Y is hydroxy and r is an integer number 1 to 6, Mitsunobu reaction is preferable.

Compound (IA) can be prepared, for example, by the method described in Processes 5-1 to 5-2 in Scheme 5.

Scheme 5

[Chem. 19]

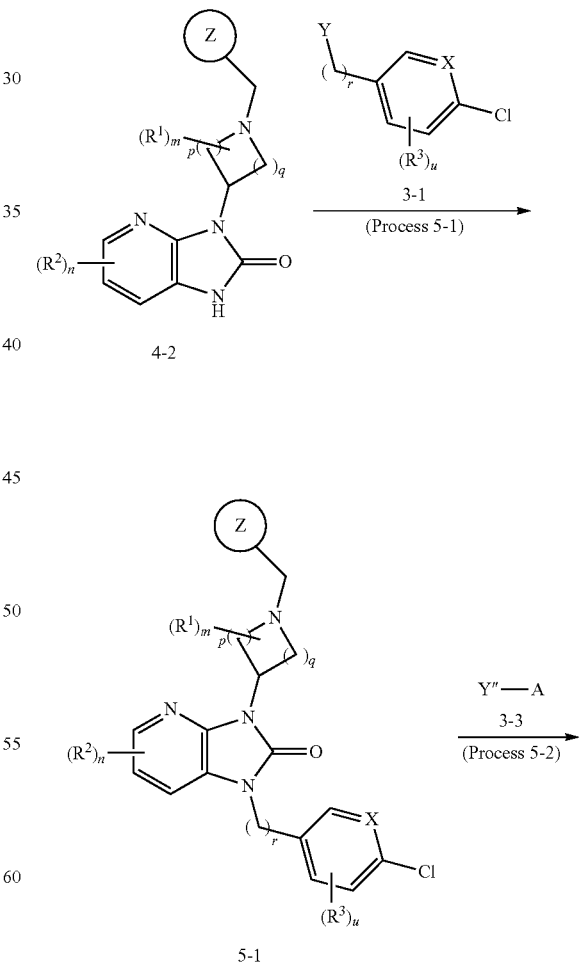

-continued

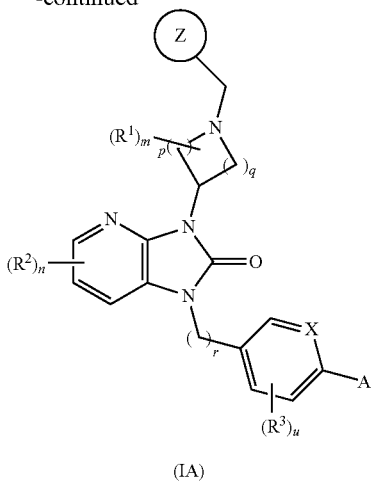

(IA)

Process 5-1

Compound (5-1) can also be prepared by Ullmann condensation reaction, Chan-Lam-Evans coupling reaction or Mitsunobu reaction of Compound (4-2) and Compound (3-1).

When Y is a bromine atom or an iodine atom, and r is 0, Ullmann condensation reaction is preferable. When Y is boronic acid, and r is 0, Chan-Lam-Evans coupling reaction is preferable. When Y is hydroxy and r is an integer number 1 to 6, Mitsunobu reaction is preferable.

Process 5-2

Compound (IA) can also be prepared by Suzuki-Miyaura cross coupling reaction of Compound (5-1) and Compound (3-3). Removal of a protective group can also be conducted, if necessary.

The above-mentioned schemes are exemplary methods for preparing the compounds represented by the formula (I) or synthetic intermediates thereof. The above schemes can be changed or modified into schemes which a person ordinarily skilled in the art can easily understand.

The compounds represented by the formula (I) and synthetic intermediates thereof can also be isolated and purified, if required, according to isolation and purification techniques well known to a person ordinarily skilled in the art, such as solvent extraction, crystallization, recrystallization, chromatography or preparative high performance liquid chromatography.

As column chromatography on silica gel and column chromatography on amino-silica gel, flash chromatography using, for example, SNAP Ultra and SNAP Isolute NH2 (Biotage), Hi-Flash column (Yamazen) and the like can be illustrated.

As ODS column chromatography, preparative isolation using, for example, preparative purification LC system (Gilson, flow rate: 30 mL/min, detection: UV at 225 nm) and column: CAPCELL PAK C18 UG80 (5 μm 20×50 mm) can be illustrated.

The compounds of the present invention have an excellent PHD2 inhibitory effect, and thus can be used as therapeutic agents for IBD (see, Nature Reviews Drug Discovery, 2014, 13, pp. 852-869). In the present invention, the phrase "IBD" includes, for example, ulcerative colitis, Crohn's disease, intestinal Behcet disease, infectious enteritis, radiation enteritis, drug-induced enteritis, ischemic enteritis, mesenteric phlebosclerosis (phlebosclerotic colitis), obstructive colitis and enteritis due to collagen disease. Preferably, the compounds of the present invention can be used as therapeutic agents for ulcerative colitis or Crohn's disease (see, Inflamm. Bowel. Dis., 2015, 21 (2), pp. 267-275).

In the present invention, the phrase "treatment" includes the meanings of "prevention". The treatment of ulcerative colitis includes, for example, the meanings of "prevention of relapse" and "maintenance of remission".

The therapeutic effects on colitis of the compounds of the present invention can be determined according to the method described in Test example 2 or well-known methods in the art. For example, the method described in Biol. Pharm. Bull., 2004, 27 (10), pp. 1599-1603 and the like or similar methods thereto can be illustrated.

In an embodiment, the compounds of the present invention are PHD2 inhibitor that act specifically on large intestine tissue to limit the off-target effects of stabilization of HIF-α. The term "act specifically on large intestine tissue" means, for example, that the concentration of the compound is high in large intestine tissue compared to that in the blood and that the compound exerts a therapeutic effect on large intestine without systemic effects (for example, hematopoietic effect) (see, Test examples 2 and 3).

The pharmaceutical composition of the present invention is used in various dosage forms depending on the usage. As such dosage forms, for example, powders, granules, fine granules, dry syrups, tablets, capsules, injections, liquids, ointments, suppositories, poultices and enema agents can be illustrated.

The pharmaceutical composition of the present invention comprises a compound represented by the formula (I) or a pharmaceutically acceptable salt thereof as an active ingredient.

The pharmaceutical composition of the present invention can be prepared using a compound represented by the formula (I) or a pharmaceutically acceptable salt thereof and at least one pharmaceutical additive. The pharmaceutical composition can be formulated by appropriately admixing, diluting or dissolving with appropriate pharmaceutical additives such as excipients, disintegrants, binders, lubricants, diluents, buffers, tonicity agents, preservatives, wetting agents, emulsifying agents, dispersing agents, stabilizing agents and solubilizing agents, according to a well-known formulation procedure depending upon the dosage form.

When the pharmaceutical composition of the present invention is used in the treatment, the dosage of the compound represented by the formula (I) or the pharmaceutically acceptable salt thereof is appropriately decided depending on the age, sex, body weight, degree of disorders and treatment of each patient and the like. The daily dose can be divided into one, two, three or four times per day and administered. Preferably, the pharmaceutical composition of the present invention is orally administered.

The dosage for an adult can be decided within the range of, for example, 0.1 to 1000 mg per day in the case of oral administration. In an embodiment, the oral administration dosage can be decided within the range of 1 to 500 mg per day, preferably 10 to 200 mg per day.

The dosage for an adult can be decided at, for example, 0.1 to 1000 mg per day in the case of parenteral administration. In an embodiment, the parenteral administration dosage can be decided within the range of 0.5 to 200 mg per day, preferably 1 to 20 mg per day.

In an embodiment, the pharmaceutical composition of the present invention can also be used in combination with any other medicament other than PHD inhibitors. As such other medicaments used in combination for the treatment of inflammatory bowel diseases, for example, 5-ASA, steroids, immunosuppressive agents, anti-TNF-α antibodies, Janus kinase inhibitors and α₄β₇ integrin antibodies can be illustrated.

When a compound represented by the formula (I) or a pharmaceutically acceptable salt thereof is used in combination with the other medicament, they can be administered as a formulation comprising these active ingredients or as formulations which are each separately formulated from each active ingredient. When separately formulated, these formulations can be administered separately or concurrently. Furthermore, the dosage of the compound represented by the formula (I) or a pharmaceutically acceptable salt thereof can be appropriately reduced depending on the dosage of the other medicament used in combination.

The compounds represented by the formula (I) may be each converted to a prodrug appropriately and be used. For example, a prodrug of a compound represented by the formula (I) can also be prepared by introducing a group forming a prodrug using a corresponding reagent for prodrug preparation such as a halide compound and purifying. As the group forming a prodrug, for example, a group described in "Development of medicine" 1990, Vol. 7, pp. 163-198, published by Hirokawa Shoten can be illustrated.

EXAMPLES

The present invention is further illustrated in more detail by way of the following Examples. However, the present invention is not limited thereto.

The compound names described in the following examples were named using ChemDraw Professional (PerkinElmer), MarvinSketch (ChemAxon) or the like except for commercially available reagents.

Reference Example A-1 tert-Butyl (S)-3-((3-nitropyridin-2-yl)amino)pyrrolidine-1-carboxylate

To NMP (100 mL) were added 2-fluoro-3-nitropyridine (10.00 g), tert-butyl (S)-3-aminopyrrolidine-1-carboxylate (13.10 g) and potassium carbonate (11.67 g) under ice-cooling. The reaction mixture was stirred at 150° C. for 1 hour. The reaction mixture was allowed to cool to room temperature. To the reaction mixture were added ethyl acetate and water, and the mixture was stirred. The mixture was extracted with ethyl acetate. The organic layer was washed with water and brine, dried over anhydrous magnesium sulfate, and concentrated under reduced pressure to give the title compound (21.70 g).

Reference Example A-2 tert-Butyl (R)-3-((3-nitropyridin-2-yl)amino)pyrrolidine-1-carboxylate

A mixture of 2-fluoro-3-nitropyridine (2.00 g), tert-butyl (R)-3-aminopyrrolidine-1-carboxylate (2.62 g), potassium carbonate (2.33 g) and NMP (15 mL) was stirred at 150° C. under microwave irradiation for 1 hour. The reaction mixture was poured into a mixture of ethyl acetate and water, and the resulting mixture was stirred. The mixture was filtered through Celite (registered trademark), and the filtrate was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=95/5-70/30) to give the title compound (3.61 g).

Reference Example A-3 tert-Butyl 4-((3-nitropyridin-2-yl)amino)piperidine-1-carboxylate

A mixture of 2-fluoro-3-nitropyridine (1.00 g), tert-butyl 4-aminopiperidine-1-carboxylate (1.41 g), potassium carbonate (1.94 g) and DMF (10 mL) was stirred at 120° C. under microwave irradiation for 1 hour. The reaction mixture was poured into a mixture of ethyl acetate and water, and the resulting mixture was stirred. The mixture was filtered through Celite, and the filtrate was extracted with ethyl acetate. The organic layer was washed with water and brine, dried over anhydrous magnesium sulfate, and concentrated under reduced pressure to give the title compound (2.25 g).

Reference Example A-4 tert-Butyl 3-((3-nitropyridin-2-yl)amino)azetidine-1-carboxylate

The title compound was prepared in a similar manner to that described in Reference Example A-3 using tert-butyl 3-aminoazetidine-1-carboxylate instead of tert-butyl 4-aminopiperidine-1-carboxylate.

Reference Example A-5 tert-Butyl (3R,4R)-3-fluoro-4-((3-nitropyridin-2-yl)amino)pyrrolidine-1-carboxylate A mixture of 2-fluoro-3-nitropyridine (0.69 g), tert-butyl (3R,4R)-3-amino-4-fluoropyrrolidine-1-carboxylate (1.00 g), potassium carbonate (1.35 g) and DMF (10 mL) was stirred at 80° C. under microwave irradiation for 1 hour. To the reaction mixture were added ethyl acetate and water, and the mixture was stirred. The mixture was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-20/80) to give the title compound (1.40 g).

Reference Example A-6 tert-Butyl (S)-3-((3-nitro-5-(trifluoromethyl)pyridin-2-yl)amino)pyrrolidine-1-carboxylate A mixture of 2-chloro-3-nitro-5-(trifluoromethyl)pyridine (1.00 g), tert-butyl (S)-3-aminopyrrolidine-1-carboxylate (0.82 g), potassium carbonate (1.22 g) and DMF (10 mL) was stirred at 80° C. under microwave irradiation for 1 hour. To the reaction mixture were added ethyl acetate and water, and the mixture was stirred. The mixture was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-20/80) to give the title compound (1.66 g).

Reference Example A-7 tert-Butyl 4-methyl-4-((3-nitropyridin-2-yl)amino) piperidine-1-carboxylate

The title compound was prepared in a similar manner to that described in Reference Example A-5 using tert-butyl 4-amino-4-methylpiperidine-1-carboxylate instead of tert-butyl (3R,4R)-3-amino-4-fluoropyrrolidine-1-carboxylate.

Reference Example A-8

Methyl (S)-6-((1-(tert-butoxycarbonyl)pyrrolidin-3-yl)amino)-5-nitropicolinate

A mixture of methyl 6-chloro-5-nitropicolinate (1.00 g), tert-butyl (S)-3-aminopyrrolidine-1-carboxylate (0.86 g), potassium carbonate (1.27 g) and DMF (10 mL) was stirred at 120° C. under microwave irradiation for 1 hour. The reaction mixture was poured into a mixture of ethyl acetate and water, and the resulting mixture was stirred. The mixture was filtered through Celite, and the filtrate was extracted with ethyl acetate. The organic layer was washed with water and brine, dried over anhydrous magnesium sulfate, and concentrated under reduced pressure to give the title compound (1.47 g).

Reference Example A-9 tert-Butyl (S)-3-((5-methyl-3-nitropyridin-2-yl) amino)pyrrolidine-1-carboxylate The title compound was prepared in a similar manner to that described in Reference Example A-6 using 2-chloro-5-methyl-3-nitropyridine instead of 2-chloro-3-nitro-5-(trifluoromethyl)pyridine.

Reference Example A-10 tert-Butyl (S)-3-((5-methoxy-3-nitropyridin-2-yl) amino)pyrrolidine-1-carboxylate The title compound was prepared in a similar manner to that described in Reference Example A-6 using 2-chloro-5-methoxy-3-nitropyridine instead of 2-chloro-3-nitro-5-(trifluoromethyl)pyridine.

Reference Example B-1 tert-Butyl (S)-3-((3-aminopyridin-2-yl)amino)pyrrolidine-1-carboxylate

To a mixture of Reference Example A-1 (21.70 g) and ethanol (300 mL) was added 10% palladium on carbon (2.17 g, wet) under an argon atmosphere. The mixture was stirred under a hydrogen atmosphere at room temperature for 6 hours. The reaction mixture was filtered through Celite, and the filtrate was concentrated under reduced pressure to give the title compound (19.74 g).

Reference Example B-2 tert-Butyl (R)-3-((3-aminopyridin-2-yl)amino)pyrrolidine-1-carboxylate

The title compound was prepared in a similar manner to that described in Reference Example B-1 using Reference Example A-2 instead of Reference Example A-1.

Reference Example B-3 tert-Butyl 4-((3-aminopyridin-2-yl)amino)piperidine-1-carboxylate

To a mixture of Reference Example A-3 (2.25 g), ethanol (20 mL) and THF (10 mL) was added 10% palladium on carbon (0.22 g, wet) under an argon atmosphere. The mixture was stirred under a hydrogen atmosphere at room temperature for 7 hours. The reaction mixture was filtered through Celite, and the filtrate was concentrated under reduced pressure to give the title compound (2.06 g).

Reference Example B-4 tert-Butyl 3-((3-aminopyridin-2-yl)amino)azetidine-1-carboxylate

The title compound was prepared in a similar manner to that described in Reference Example B-1 using Reference Example A-4 instead of Reference Example A-1.

Reference Example B-5 tert-Butyl (3R,4R)-3-((3-aminopyridin-2-yl)amino)-4-fluoropyrrolidine-1-carboxylate The title compound was prepared in a similar manner to that described in Reference Example B-1 using Reference Example A-5 instead of Reference Example A-1.

Reference Example B-6 tert-Butyl (S)-3-((3-amino-5-(trifluoromethyl)pyridin-2-yl)amino)pyrrolidine-1-carboxylate The title compound was prepared in a similar manner to that described in Reference Example B-1 using Reference Example A-6 instead of Reference Example A-1.

Reference Example B-7 tert-Butyl 4-((3-aminopyridin-2-yl)amino)-4-methylpiperidine-1-carboxylate

The title compound was prepared in a similar manner to that described in Reference Example B-1 using Reference Example A-7 instead of Reference Example A-1.

Reference Example B-8

Methyl (S)-5-amino-6-((1-(tert-butoxycarbonyl) pyrrolidin-3-yl)amino)picolinate

The title compound was prepared in a similar manner to that described in Reference Example B-1 using Reference Example A-8 instead of Reference Example A-1.

Reference Example B-9 tert-Butyl (S)-3-((3-amino-5-methylpyridin-2-yl) amino)pyrrolidine-1-carboxylate The title compound was prepared in a similar manner to that described in Reference Example B-1 using Reference Example A-9 instead of Reference Example A-1.

Reference Example B-10 tert-Butyl (S)-3-((3-amino-5-methoxypyridin-2-yl)amino)pyrrolidine-1-carboxylate The title compound was prepared in a similar manner to that described in Reference Example B-1 using Reference Example A-10 instead of Reference Example A-1.

Reference Example C-1 tert-Butyl (S)-3-(2-oxo-1,2-dihydro-3H-imidazo[4,5-b]pyridin-3-yl)pyrrolidine-1-carboxylate To a mixture of Reference Example B-1 (19.59 g) and THF (200 mL) was added CDI (22.82 g) under ice-cooling with stirring. The reaction mixture was stirred at room temperature for 30 minutes. To the reaction mixture was added an aqueous solution of sodium hydroxide (5 mol/L, 30 mL), and the resulting mixture was stirred for 10 minutes. To the reaction mixture was added hydrochloric acid (2 mol/L, 75 mL). After stirring, the mixture was concentrated under reduced pressure. To the obtained mixture was added water, and the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=50/50-0/100) to give the title compound (17.61 g). MS (ESI_APCI, m/z): 303 (M−H)⁻

Reference Example C-2 tert-Butyl (R)-3-(2-oxo-1,2-dihydro-3H-imidazo[4,5-b]pyridin-3-yl)pyrrolidine-1-carboxylate To a mixture of Reference Example B-2 (3.68 g) and THF (20 mL) was added CDI (4.28 g). The reaction mixture was stirred at room temperature for 30 minutes. To the reaction mixture was added an aqueous solution of sodium hydroxide (5 mol/L, 4 mL), and the resulting mixture was stirred for 5 minutes. To the reaction mixture was added hydrochloric acid (2 mol/L, 10 mL), and the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=50/50-0/100) to give the title compound (4.00 g). MS (ESI_APCI, m/z): 303 (M−H)⁻

Reference Example C-3 tert-Butyl 4-(2-oxo-1,2-dihydro-3H-imidazo[4,5-b]pyridin-3-yl)piperidine-1-carboxylate To a mixture of Reference Example B-3 (2.06 g) and THF (30 mL) was added CDI (2.29 g). The reaction mixture was stirred at room temperature for 1 hour. To the reaction mixture was added water, and the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-0/100) to give the title compound (1.96 g). MS (ESI_APCI, m/z): 317 (M−H)⁻

Reference Example C-4 tert-Butyl 3-(2-oxo-1,2-dihydro-3H-imidazo[4,5-b]pyridin-3-yl)azetidine-1-carboxylate The title compound was prepared in a similar manner to that described in Reference Example C-1 using Reference Example B-4 instead of Reference Example B-1. MS (ESI_APCI, m/z): 289 (M−H)⁻

Reference Example C-5 tert-Butyl (3R,4R)-3-fluoro-4-(2-oxo-1,2-dihydro-3H-imidazo[4,5-b]pyridin-3-yl)pyrrolidine-1-carboxylate The title compound was prepared in a similar manner to that described in Reference Example C-2 using Reference Example B-5 instead of Reference Example B-2. MS (ESI_APCI, m/z): 321 (M−H)⁻

Reference Example C-6 tert-Butyl (S)-3-(2-oxo-6-(trifluoromethyl)-1,2-dihydro-3H-imidazo[4,5-b]pyridin-3-yl)pyrrolidine-1-carboxylate The title compound was prepared in a similar manner to that described in Reference Example C-2 using Reference Example B-6 instead of Reference Example B-2. MS (ESI_APCI, m/z): 371 (M−H)⁻

Reference Example C-7 tert-Butyl 4-methyl-4-(2-oxo-1,2-dihydro-3H-imidazo[4,5-b]pyridin-3-yl)piperidine-1-carboxylate The title compound was prepared in a similar manner to that described in Reference Example C-2 using Reference Example B-7 instead of Reference Example B-2. MS (ESI_APCI, m/z): 331 (M−H)⁻

Reference Example C-8

Methyl (S)-3-(1-(tert-butoxycarbonyl)pyrrolidin-3-yl)-2-oxo-2,3-dihydro-1H-imidazo[4,5-b]pyridine-5-carboxylate The title compound was prepared in a similar manner to that described in Reference Example C-3 using Reference Example B-8 instead of Reference Example B-3. MS (ESI_APCI, m/z): 361 (M−H)⁻

Reference Example C-9 tert-Butyl (S)-3-(6-methyl-2-oxo-1,2-dihydro-3H-imidazo[4,5-b]pyridin-3-yl)pyrrolidine-1-carboxylate The title compound was prepared in a similar manner to that described in Reference Example C-2 using Reference Example B-9 instead of Reference Example B-2. MS (ESI_APCI, m/z): 317 (M−H)⁻

Reference Example C-10 tert-Butyl (S)-3-(6-methoxy-2-oxo-1,2-dihydro-3H-imidazo[4,5-b]pyridin-3-yl)pyrrolidine-1-carboxylate The title compound was prepared in a similar manner to that described in Reference Example C-2 using Reference Example B-10 instead of Reference Example B-2. MS (ESI_APCI, m/z): 333 (M−H)⁻

Reference Example D-1 tert-Butyl (S)-3-(1-(4-chloro-2-methylphenyl)-2-oxo-1,2-dihydro-3H-imidazo[4,5-b]pyridin-3-yl)pyrrolidine-1-carboxylate A mixture of Reference Example C-1 (168 mg), (4-chloro-2-methylphenyl)boronic acid (282 mg), copper (II) acetate (201 mg), triethylamine (0.383 mL) and dichloromethane (3 mL) was stirred at room temperature for 3 hours. To the reaction mixture were added water and hydrochloric acid (1 mol/L). After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-50/50) to give the title compound (114 mg).

Reference Example D-2 tert-Butyl (S)-3-(1-(4-chlorophenyl)-2-oxo-1,2-dihydro-3H-imidazo[4,5-b]pyridin-3-yl)pyrrolidine-1-carboxylate A mixture of Reference Example C-1 (500 mg), 1-chloro-4-iodobenzene (431 mg), N,N'-dimethylethylenediamine (0.212 mL), copper (I) iodide (375 mg), potassium carbonate (681 mg) and acetonitrile (10 mL) was stirred at 90° C. under microwave irradiation for 1 hour. The reaction mixture was poured into a mixture of water and hydrochloric acid (1 mol/L). After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-50/50) to give the title compound (583 mg).

Reference Example D-3 tert-Butyl (R)-3-(1-(4-chloro-2-methylphenyl)-2-oxo-1,2-dihydro-3H-imidazo[4,5-b]pyridin-3-yl)pyrrolidine-1-carboxylate The title compound was prepared in a similar manner to that described in Reference Example D-1 using Reference Example C-2 instead of Reference Example C-1.

Reference Example D-4 tert-Butyl (S)-3-(1-(4-chloro-2-hydroxyphenyl)-2-oxo-1,2-dihydro-3H-imidazo[4,5-b]pyridin-3-yl)pyrrolidine-1-carboxylate A mixture of Reference Example C-1 (100 mg), 5-chloro-2-iodophenol (125 mg), N,N'-dimethylethylenediamine (0.042 mL), copper (I) iodide (75 mg), potassium carbonate (136 mg) and acetonitrile (3 mL) was stirred at 100° C. under microwave irradiation for 2 hours. The reaction mixture was poured into a mixture of water and hydrochloric acid (1 mol/L). After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=35/65) to give the title compound (61 mg).

Reference Example D-5 tert-Butyl (S)-3-(1-(4-chloro-3-hydroxyphenyl)-2-oxo-1,2-dihydro-3H-imidazo[4,5-b]pyridin-3-yl)pyrrolidine-1-carboxylate A mixture of Reference Example C-1 (100 mg), 2-chloro-5-iodophenol (100 mg), N,N'-dimethylethylenediamine (0.042 mL), copper (I) iodide (75 mg), potassium carbonate (136 mg) and acetonitrile (3 mL) was stirred at 100° C. under microwave irradiation for 1 hour. The reaction mixture was poured into a mixture of water and hydrochloric acid (1 mol/L). After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=35/65) to give the title compound (135 mg).

Reference Example D-6 tert-Butyl (S)-3-(1-(6-chloropyridin-3-yl)-2-oxo-1,2-dihydro-3H-imidazo[4,5-b]pyridin-3-yl)pyrrolidine-1-carboxylate A mixture of Reference Example C-1 (100 mg), 2-chloro-5-iodopyridine (94 mg), N,N'-dimethylethylenediamine (0.042 mL), copper (I) iodide (75 mg), potassium carbonate (136 mg) and acetonitrile (3 mL) was stirred at 100° C. under microwave irradiation for 1 hour. The reaction mixture was poured into a mixture of water and hydrochloric acid (1 mol/L). After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=35/65) to give the title compound (117 mg).

Reference Example D-7 tert-Butyl (R)-3-(1-(6-chloropyridin-3-yl)-2-oxo-1,2-dihydro-3H-imidazo[4,5-b]pyridin-3-yl)pyrrolidine-1-carboxylate A mixture of Reference Example C-2 (500 mg), 2-chloro-5-iodopyridine (433 mg), N,N'-dimethylethylenediamine (0.212 mL), copper (I) iodide (375 mg), potassium carbonate (681 mg) and acetonitrile (10 mL) was stirred at 100° C. under microwave irradiation for 1 hour. The reaction mixture was poured into a mixture of water and ethyl acetate. After stirring, the mixture was filtered through Celite. The filtrate was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-45/55) to give the title compound (420 mg).

Reference Example E-1 tert-Butyl (S)-3-(1-([1,1'-biphenyl]-4-yl)-2-oxo-1,2-dihydro-3H-imidazo[4,5-b]pyridin-3-yl)pyrrolidine-1-carboxylate A mixture of Reference Example C-1 (113 mg), 4-iodo-1,1'-biphenyl (125 mg), N,N'-dimethylethylenediamine (0.048 mL), copper (I) iodide (85 mg), potassium carbonate (154 mg) and acetonitrile (4 mL) was stirred at 100° C. under microwave irradiation for 1 hour. The reaction mixture was poured into a mixture of water and hydrochloric acid (1 mol/L). After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-50/50) to give the title compound (138 mg).

Reference Example E-2 tert-Butyl (R)-3-(1-([1,1'-biphenyl]-4-yl)-2-oxo-1,2-dihydro-3H-imidazo[4,5-b]pyridin-3-yl)pyrrolidine-1-carboxylate The title compound was prepared in a similar manner to that described in Reference Example E-1 using Reference Example C-2 instead of Reference Example C-1.

Reference Example E-3 tert-Butyl (S)-3-(2-oxo-1-phenyl-1,2-dihydro-3H-imidazo[4,5-b]pyridin-3-yl)pyrrolidine-1-carboxylate The title compound was prepared in a similar manner to that described in Reference Example E-1 using iodobenzene instead of 4-iodo-1,1'-biphenyl.

Reference Example E-4 tert-Butyl 4-(1-([1,1'-biphenyl]-4-yl)-2-oxo-1,2-dihydro-3H-imidazo[4,5-b]pyridin-3-yl)piperidine-1-carboxylate The title compound was prepared in a similar manner to that described in Reference Example E-1 using Reference Example C-3 instead of Reference Example C-1.

Reference Example E-5 tert-Butyl 3-(1-([1,1'-biphenyl]-4-yl)-2-oxo-1,2-dihydro-3H-imidazo[4,5-b]pyridin-3-yl)azetidine-1-carboxylate A mixture of Reference Example C-4 (100 mg), 4-iodo-1,1'-biphenyl (96 mg), N,N'-dimethylethylenediamine (0.044 mL), copper (I) iodide (79 mg), potassium carbonate (143 mg) and acetonitrile (3 mL) was stirred at 100° C. under microwave irradiation for 1 hour. The reaction mixture was poured into a mixture of water and ethyl acetate. After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-50/50) to give the title compound (105 mg).

Reference Example E-6 tert-Butyl (S)-3-(1-(4-(methoxycarbonyl)phenyl)-2-oxo-1,2-dihydro-3H-imidazo[4,5-b]pyridin-3-yl)pyrrolidine-1-carboxylate A mixture of Reference Example C-1 (200 mg), methyl 4-iodobenzoate (172 mg), N,N'-dimethylethylenediamine (0.085 mL), copper (I) iodide (150 mg), potassium carbonate (272 mg) and acetonitrile (1 mL) was stirred at 100° C. under microwave irradiation for 1 hour. The reaction mixture was poured into a mixture of water and ethyl acetate. After stirring, the mixture was filtered through Celite. The filtrate was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-45/55) to give the title compound (271 mg).

Reference Example E-7 tert-Butyl (S)-3-(1-(4-methoxyphenyl)-2-oxo-1,2-dihydro-3H-imidazo[4,5-b]pyridin-3-yl)pyrrolidine-1-carboxylate A mixture of Reference Example C-1 (100 mg), 1-iodo-4-methoxybenzene (85 mg), N,N'-dimethylethylenediamine (0.042 mL), copper (I) iodide (75 mg), potassium carbonate (136 mg) and acetonitrile (1 mL) was stirred at 100° C. under microwave irradiation for 1 hour. The reaction mixture was poured into a mixture of water and hydrochloric acid (1 mol/L). After stirring, the mixture was filtered through Celite. The filtrate was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-50/50) to give the title compound (119 mg).

Reference Example E-8

Methyl (S)-1-([1,1'-biphenyl]-4-yl)-3-(1-(tert-butoxycarbonyl)pyrrolidin-3-yl)-2-oxo-2,3-dihydro-1H-imidazo[4,5-b]pyridine-5-carboxylate A mixture of Reference Example C-8 (100 mg), 4-iodo-1,1'-biphenyl (93 mg), N,N'-dimethylethylenediamine (0.036 mL), copper (I) iodide (63 mg), potassium carbonate (114 mg) and acetonitrile (1 mL) was stirred at 100° C. under microwave irradiation for 1 hour. The reaction mixture was poured into a mixture of water and ethyl acetate. After stirring, the mixture was filtered through Celite. The filtrate was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-45/55) to give the title compound (120 mg).

Reference Example E-9 tert-Butyl 4-(1-([1,1'-biphenyl]-4-yl)-2-oxo-1,2-dihydro-3H-imidazo[4,5-b]pyridin-3-yl)-4-methylpiperidine-1-carboxylate A mixture of Reference Example C-7 (50 mg), 4-iodo-1,1'-biphenyl (51 mg), N,N'-dimethylethylenediamine (0.019 mL), copper (I) iodide (34 mg), potassium carbonate (50 mg) and acetonitrile (3 mL) was stirred at 100° C. under microwave irradiation for 1 hour. The reaction mixture was poured into ethyl acetate, and the resulting mixture was stirred. The mixture was filtered through Celite, and the filtrate was concentrated under reduced pressure. The residue was purified by column chromatography on silica gel (eluent: n-hexane/ethyl acetate=80/20-40/60) to give the title compound (70 mg).

Reference Example E-10 tert-Butyl (S)-3-(6-methoxy-1-(4'-(methoxycarbonyl)-[1,1'-biphenyl]-4-yl)-2-oxo-1,2-dihydro-3H-imidazo[4,5-b]pyridin-3-yl)pyrrolidine-1-carboxylate A mixture of Reference Example C-10 (136 mg), methyl 4'-bromo-[1,1'-biphenyl]-4-carboxylate (131 mg), N,N'-dimethylethylenediamine (0.053 mL), copper (I) iodide (94 mg), potassium carbonate (136 mg) and acetonitrile (1 mL) was stirred at 100° C. under microwave irradiation for 1 hour. The reaction mixture was poured into ethyl acetate, and the resulting mixture was stirred. The mixture was filtered through Celite, and the filtrate was concentrated under reduced pressure. The residue was purified by column chromatography on silica gel (eluent: n-hexane/ethyl acetate=80/20-25/75) to give the title compound (128 mg).

Reference Example E-11 tert-Butyl (3R,4R)-3-fluoro-4-(1-(4'-(methoxycarbonyl)-[1,1'-biphenyl]-4-yl)-2-oxo-1,2-dihydro-3H-imidazo[4,5-b]pyridin-3-yl)pyrrolidine-1-carboxylate The title compound was prepared in a similar manner to that described in Reference Example E-10 using Reference Example C-5 instead of Reference Example C-10.

Reference Example E-12 tert-Butyl (S)-3-(1-(4'-(methoxycarbonyl)-[1,1'-biphenyl]-4-yl)-2-oxo-6-(trifluoromethyl)-1,2-dihydro-3H-imidazo[4,5-b]pyridin-3-yl)pyrrolidine-1-carboxylate The title compound was prepared in a similar manner to that described in Reference Example E-10 using Reference Example C-6 instead of Reference Example C-10.

Reference Example E-13 tert-Butyl (S)-3-(1-(3-methyl-[1,1'-biphenyl]-4-yl)-2-oxo-1,2-dihydro-3H-imidazo[4,5-b]pyridin-3-yl)pyrrolidine-1-carboxylate A mixture of Reference Example D-1 (114 mg), phenylboronic acid (39 mg), Pd(amphos)Cl$_2$ (19 mg), sodium carbonate (68 mg), DMF (1 mL) and water (0.1 mL) was stirred at 150° C. under microwave irradiation for 1 hour. The reaction mixture was poured into a mixture of water and ethyl acetate. After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-50/50) to give the title compound (87 mg).

Reference Example E-14 tert-Butyl (S)-3-(1-(2'-methyl-[1,1'-biphenyl]-4-yl)-2-oxo-1,2-dihydro-3H-imidazo[4,5-b]pyridin-3-yl)pyrrolidine-1-carboxylate A mixture of Reference Example D-2 (100 mg), o-tolylboronic acid (39 mg), Pd(amphos)Cl$_2$ (17 mg), sodium carbonate (61 mg), DMF (1 mL) and water (0.1 mL) was stirred at 150° C. under microwave irradiation for 1 hour. The reaction mixture was poured into a mixture of water and ethyl acetate. After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-50/50) to give the title compound (105 mg).

Reference Example E-15 tert-Butyl (R)-3-(1-(3-methyl-[1,1'-biphenyl]-4-yl)-2-oxo-1,2-dihydro-3H-imidazo[4,5-b]pyridin-3-yl)pyrrolidine-1-carboxylate The title compound was prepared in a similar manner to that described in Reference Example E-13 using Reference Example D-3 instead of Reference Example D-1.

Reference Example E-16 tert-Butyl (S)-3-(1-(4'-fluoro-[1,1'-biphenyl]-4-yl)-2-oxo-1,2-dihydro-3H-imidazo[4,5-b]pyridin-3-yl)pyrrolidine-1-carboxylate The title compound was prepared in a similar manner to that described in Reference Example E-14 using (4-fluorophenyl)boronic acid instead of o-tolylboronic acid.

Reference Example E-17 tert-Butyl (S)-3-(1-(4'-methoxy-[1,1'-biphenyl]-4-yl)-2-oxo-1,2-dihydro-3H-imidazo[4,5-b]pyridin-3-yl)pyrrolidine-1-carboxylate The title compound was prepared in a similar manner to that described in Reference Example E-14 using (4-methoxyphenyl)boronic acid instead of o-tolylboronic acid.

Reference Example E-18 tert-Butyl (S)-3-(2-oxo-1-(2'-(trifluoromethyl)-[1,1'-biphenyl]-4-yl)-1,2-dihydro-3H-imidazo[4,5-b]pyridin-3-yl)pyrrolidine-1-carboxylate The title compound was prepared in a similar manner to that described in Reference Example E-14 using (2-(trifluoromethyl)phenyl)boronic acid instead of o-tolylboronic acid.

Reference Example E-19 tert-Butyl (S)-3-(1-(4'-cyano-[1,1'-biphenyl]-4-yl)-2-oxo-1,2-dihydro-3H-imidazo[4,5-b]pyridin-3-yl)pyrrolidine-1-carboxylate The title compound was prepared in a similar manner to that described in Reference Example E-14 using (4-cyanophenyl)boronic acid instead of o-tolylboronic acid.

Reference Example E-20 tert-Butyl (S)-3-(2-oxo-1-(4'-(trifluoromethoxy)-[1,1'-biphenyl]-4-yl)-1,2-dihydro-3H-imidazo[4,5-b]pyridin-3-yl)pyrrolidine-1-carboxylate The title compound was prepared in a similar manner to that described in Reference Example E-14 using (4-(trifluoromethoxy)phenyl)boronic acid instead of o-tolylboronic acid.

Reference Example E-21 tert-Butyl (S)-3-(1-(4'-hydroxy-[1,1'-biphenyl]-4-yl)-2-oxo-1,2-dihydro-3H-imidazo[4,5-b]pyridin-3-yl)pyrrolidine-1-carboxylate The title compound was prepared in a similar manner to that described in Reference Example E-1 using 4'-iodo-[1,1'-biphenyl]-4-ol instead of 4-iodo-1,1'-biphenyl.

Reference Example E-22 tert-Butyl (S)-3-(2-oxo-1-(4-(pyridin-4-yl)phenyl)-1,2-dihydro-3H-imidazo[4,5-b]pyridin-3-yl)pyrrolidine-1-carboxylate The title compound was prepared in a similar manner to that described in Reference Example E-14 using 4-pyridylboronic acid instead of o-tolylboronic acid.

Reference Example E-23 tert-Butyl (S)-3-(1-(4'-(methoxycarbonyl)-[1,1'-biphenyl]-4-yl)-2-oxo-1,2-dihydro-3H-imidazo[4,5-b]pyridin-3-yl)pyrrolidine-1-carboxylate A mixture of Reference Example D-2 (200 mg), (4-(methoxycarbonyl)phenyl)boronic acid (104 mg), Pd(amphos)Cl$_2$ (34 mg), sodium carbonate (123 mg), DMF (2 mL) and water (0.2 mL) was stirred at 150° C. under microwave irradiation for 1 hour. The reaction mixture was poured into a mixture of water and ethyl acetate. After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-50/50) to give the title compound (212 mg).

Reference Example E-24 tert-Butyl (R)-3-(1-(4'-(methoxycarbonyl)-3-methyl-[1,1'-biphenyl]-4-yl)-2-oxo-1,2-dihydro-3H-imidazo[4,5-b]pyridin-3-yl)pyrrolidine-1-carboxylate The title compound was prepared in a similar manner to that described in Reference Example E-23 using Reference Example D-3 instead of Reference Example D-2.

Reference Example E-25 tert-Butyl (S)-3-(1-(3-hydroxy-4'-(methoxycarbonyl)-[1,1'-biphenyl]-4-yl)-2-oxo-1,2-dihydro-3H-imidazo[4,5-b]pyridin-3-yl)pyrrolidine-1-carboxylate A mixture of Reference Example D-4 (61 mg), (4-(methoxycarbonyl)phenyl)boronic acid (31 mg), Pd(amphos)Cl$_2$ (10 mg), sodium carbonate (36 mg), DMF (1 mL) and water (0.1 mL) was stirred at 150° C. under microwave irradiation for 1 hour. The reaction mixture was poured into a mixture of water and ethyl acetate. After stirring, the mixture was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-35/65) to give the title compound (55 mg).

Reference Example E-26 tert-Butyl (S)-3-(1-(2-hydroxy-4'-(methoxycarbonyl)-[1,1'-biphenyl]-4-yl)-2-oxo-1,2-dihydro-3H-imidazo[4,5-b]pyridin-3-yl)pyrrolidine-1-carboxylate A mixture of Reference Example D-5 (135 mg), (4-(methoxycarbonyl)phenyl)boronic acid (113 mg), Pd(amphos)Cl$_2$ (22 mg), sodium carbonate (80 mg), NMP (3 mL) and water (0.3 mL) was stirred at 150° C. under microwave irradiation for 5 hours. The reaction mixture was poured into a mixture of water and ethyl acetate. After stirring, the mixture was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-30/70) to give the title compound (122 mg).

Reference Example E-27 tert-Butyl (S)-3-(1-(6-(4-(methoxycarbonyl)phenyl)pyridin-3-yl)-2-oxo-1,2-dihydro-3H-imidazo[4,5-b]pyridin-3-yl)pyrrolidine-1-carboxylate A mixture of Reference Example D-6 (117 mg), (4-(methoxycarbonyl)phenyl)boronic acid (61 mg), Pd(amphos)Cl$_2$ (20 mg), sodium carbonate (72 mg), DMF (3 mL) and water (0.3 mL) was stirred at 150° C. under microwave irradiation for 1 hour. The reaction mixture was poured into a mixture of water and ethyl acetate. After stirring, the mixture was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-30/70) to give the title compound (95 mg).

Reference Example E-28 tert-Butyl (S)-3-(1-(4'-hydroxy-3'-(methoxycarbonyl)-[1,1'-biphenyl]-4-yl)-2-oxo-1,2-dihydro-3H-imidazo[4,5-b]pyridin-3-yl)pyrrolidine-1-carboxylate A mixture of Reference Example D-2 (121 mg), methyl 2-hydroxy-5-(4,4,5,5-tetramethyl-1,3,2-dioxaborolan-2-yl)

benzoate (98 mg), Pd(amphos)Cl$_2$ (21 mg), sodium carbonate (75 mg), DMF (1 mL) and water (0.1 mL) was stirred at 150° C. under microwave irradiation for 1 hour. The reaction mixture was poured into a mixture of water and ethyl acetate. After stirring, the mixture was filtered through Celite. The filtrate was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-30/70) to give the title compound (71 mg).

Reference Example E-29 tert-Butyl (S)-3-(1-(2'-hydroxy-4'-(methoxycarbonyl)-[1,1'-biphenyl]-4-yl)-2-oxo-1,2-dihydro-3H-imidazo[4,5-b]pyridin-3-yl)pyrrolidine-1-carboxylate A mixture of Reference Example D-2 (200 mg), methyl 3-hydroxy-4-(4,4,5,5-tetramethyl-1,3,2-dioxaborolan-2-yl) benzoate (147 mg), Pd(amphos)Cl$_2$ (34 mg), sodium carbonate (123 mg), DMF (1 mL) and water (0.1 mL) was stirred at 150° C. under microwave irradiation for 1 hour. The reaction mixture was poured into a mixture of water and ethyl acetate. After stirring, the mixture was filtered through Celite. The filtrate was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-35/65) to give the title compound (165 mg).

Reference Example E-30 tert-Butyl (S)-3-(1-(6-(4-(methoxycarbonyl)-2-methylphenyl)pyridin-3-yl)-2-oxo-1,2-dihydro-3H-imidazo[4,5-b]pyridin-3-yl)pyrrolidine-1-carboxylate A mixture of Reference Example D-6 (353 mg), (4-(methoxycarbonyl)-2-methylphenyl)boronic acid (198 mg), Pd(amphos)Cl$_2$ (60 mg), sodium carbonate (216 mg), DMF (10 mL) and water (1 mL) was stirred at 120° C. under microwave irradiation for 1 hour. The reaction mixture was poured into a mixture of water and ethyl acetate. After stirring, the mixture was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-35/65) to give the title compound (406 mg).

Reference Example K-19 tert-Butyl (S)-3-(1-(4-chloro-3-(methoxymethoxy) phenyl)-2-oxo-1,2-dihydro-3H-imidazo[4,5-b]pyridin-3-yl)pyrrolidine-1-carboxylate To a mixture of Reference Example D-5 (1.29 g) and THF (15 mL) were added DIPEA (1.55 mL) and chloromethyl methyl ether (0.34 mL). The reaction mixture was stirred at room temperature overnight. The reaction mixture was concentrated under reduced pressure. The residue was purified by column chromatography on silica gel (eluent: n-hexane/ ethyl acetate=80/20-50/50) to give the title compound (1.33 g).

Reference Example E-31 tert-Butyl (S)-3-(1-(3'-cyano-4'-hydroxy-2-(methoxymethoxy)-[1,1'-biphenyl]-4-yl)-2-oxo-1,2-dihydro-3H-imidazo[4,5-b]pyridin-3-yl)pyrrolidine-1-carboxylate A mixture of Reference Example K-19 (500 mg), 2-hydroxy-5-(4,4,5,5-tetramethyl-1,3,2-dioxaborolan-2-yl) benzonitrile (387 mg), Pd(amphos)Cl$_2$ (75 mg), sodium carbonate (268 mg), DMF (10 mL) and water (1 mL) was stirred at 150° C. under microwave irradiation for 1 hour. The reaction mixture was poured into a mixture of water and ethyl acetate. After stirring, the mixture was filtered through Celite. The filtrate was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-40/60) to give the title compound (332 mg).

Reference Example E-32 tert-Butyl (S)-3-(1-(6-(3-cyano-4-hydroxyphenyl) pyridin-3-yl)-2-oxo-1,2-dihydro-3H-imidazo[4,5-b] pyridin-3-yl)pyrrolidine-1-carboxylate The title compound was prepared in a similar manner to that described in Reference Example E-31 using Reference Example D-6 instead of Reference Example K-19.

Reference Example K-20 tert-Butyl (S)-3-(1-(4-chloro-2-(methoxymethoxy) phenyl)-2-oxo-1,2-dihydro-3H-imidazo[4,5-b]pyridin-3-yl)pyrrolidine-1-carboxylate The title compound was prepared in a similar manner to that described in Reference Example K-19 using Reference Example D-4 instead of Reference Example D-5.

Reference Example E-33 tert-Butyl (S)-3-(1-(3'-cyano-4'-hydroxy-3-(methoxymethoxy)-[1,1'-biphenyl]-4-yl)-2-oxo-1,2-dihydro-3H-imidazo[4,5-b]pyridin-3-yl)pyrrolidine-1-carboxylate The title compound was prepared in a similar manner to that described in Reference Example E-31 using Reference Example K-20 instead of Reference Example K-19.

Reference Example K-2 (S)-1-([1,1'-Biphenyl]-4-yl)-3-(1-(tert-butoxycarbonyl)pyrrolidin-3-yl)-2-oxo-2,3-dihydro-1H-imidazo[4,5-b]pyridine-5-carboxylic acid To a mixture of Reference Example E-8 (251 mg), methanol (0.5 mL), THF (0.5 mL) and water (1 mL) was added lithium hydroxide monohydrate (103 mg). The reaction mixture was stirred at room temperature for 3 hours. To the reaction mixture was added hydrochloric acid (2 mol/L, 1.2 mL). After stirring, the mixture was extracted with ethyl acetate. The organic layer was washed with brine, dried over anhydrous magnesium sulfate, and concentrated under reduced pressure to give the title compound (227 mg).

Reference Example E-34 tert-Butyl (S)-3-(1-([1,1'-biphenyl]-4-yl)-2-oxo-5-((tetrahydro-2H-pyran-4-yl)carbamoyl)-1,2-dihydro-3H-imidazo[4,5-b]pyridin-3-yl)pyrrolidine-1-carboxylate To a mixture of Reference Example K-2 (100 mg) and DMF (1 mL) were added EDC-HCl (77 mg), HOBt-H$_2$O (61 mg), triethylamine (0.139 mL) and 4-aminotetrahydropyran (24 mg). The reaction mixture was stirred at room temperature for 4 hours. To the reaction mixture were added water and ethyl acetate. After stirring, the mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=80/20-20/80) to give the title compound (19 mg).

Reference Example E-35 tert-Butyl (S)-3-(1-([1,1'-biphenyl]-4-yl)-5-((2-methoxy-2-oxoethyl)carbamoyl)-2-oxo-1,2-dihydro-3H-imidazo[4,5-b]pyridin-3-yl)pyrrolidine-1-carboxylate The title compound was prepared in a similar manner to that described in Reference Example E-34 using methyl glycinate hydrochloride instead of 4-aminotetrahydropyran.

Reference Example E-36 tert-Butyl (R)-3-(1-(6-(4-(methoxycarbonyl)phenyl)pyridin-3-yl)-2-oxo-1,2-dihydro-3H-imidazo[4,5-b]pyridin-3-yl)pyrrolidine-1-carboxylate A mixture of Reference Example D-7 (420 mg), (4-(methoxycarbonyl)phenyl)boronic acid (236 mg), Pd(amphos)Cl$_2$ (72 mg), sodium carbonate (257 mg), DMF (10 mL) and water (1 mL) was stirred at 120° C. under microwave irradiation for 1 hour. The reaction mixture was poured into a mixture of water and ethyl acetate. After stirring, the mixture was filtered through Celite. The filtrate was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-40/60) to give the title compound (377 mg).

Reference Example E-37 tert-Butyl (S)-3-(1-(naphthalen-2-yl)-2-oxo-1,2-dihydro-3H-imidazo[4,5-b]pyridin-3-yl)pyrrolidine-1-carboxylate A mixture of Reference Example C-1 (200 mg), 2-bromonaphthalene (136 mg), N,N'-dimethylethylenediamine (0.085 mL), copper (I) iodide (150 mg), potassium carbonate (218 mg) and acetonitrile (3 mL) was stirred at 100° C. under microwave irradiation for 1 hour. The reaction mixture was poured into a mixture of ethyl acetate and water. After stirring, the mixture was filtered through Celite. The filtrate was extracted with ethyl acetate. The organic layer was washed with water and brine, dried over anhydrous magnesium sulfate, and concentrated under reduced pressure. The residue was purified by column chromatography on silica gel (eluent: n-hexane/ethyl acetate=80/20-50/50) to give the title compound (250 mg).

Reference Example E-38 tert-Butyl (S)-3-(1-([1,1'-biphenyl]-3-yl)-2-oxo-1,2-dihydro-3H-imidazo[4,5-b]pyridin-3-yl)pyrrolidine-1-carboxylate A mixture of Reference Example C-1 (200 mg), 3-bromo-1,1'-biphenyl (153 mg), N,N'-dimethylethylenediamine (0.085 mL), copper (I) iodide (150 mg), potassium carbonate (218 mg) and acetonitrile (3 mL) was stirred at 100° C. under microwave irradiation for 1 hour. The reaction mixture was poured into ethyl acetate, and the resulting mixture was stirred. The mixture was filtered through Celite, and the filtrate was concentrated under reduced pressure. The residue was purified by column chromatography on silica gel (eluent: n-hexane/ethyl acetate=80/20-50/50) to give the title compound (345 mg).

Reference Example E-39 tert-Butyl (S)-3-(1-(4'-(methoxycarbonyl)-[1,1'-biphenyl]-4-yl)-6-methyl-2-oxo-1,2-dihydro-3H-imidazo[4,5-b]pyridin-3-yl)pyrrolidine-1-carboxylate The title compound was prepared in a similar manner to that described in Reference Example E-10 using Reference Example C-9 instead of Reference Example C-10.

Reference Example F-1

(S)-1-([1,1'-Biphenyl]-4-yl)-3-(pyrrolidin-3-yl)-1,3-dihydro-2H-imidazo[4,5-b]pyridin-2-one hydrochloride A mixture of Reference Example E-1 (138 mg) and hydrogen chloride (4 mol/L, 1,4-dioxane solution, 1 mL) was stirred at room temperature for 30 minutes. The reaction mixture was concentrated under reduced pressure to give the title compound (110 mg). MS (ESI_APCI, m/z): 357 (M+H)$^+$

Reference Example F-2

(R)-1-([1,1'-Biphenyl]-4-yl)-3-(pyrrolidin-3-yl)-1,3-dihydro-2H-imidazo[4,5-b]pyridin-2-one hydrochloride The title compound was prepared in a similar manner to that described in Reference Example F-1 using Reference Example E-2 instead of Reference Example E-1. MS (ESI_APCI, m/z): 357 (M+H)$^+$

Reference Example F-3

(S)-1-Phenyl-3-(pyrrolidin-3-yl)-1,3-dihydro-2H-imidazo[4,5-b]pyridin-2-one hydrochloride A mixture of Reference Example E-3 (360 mg), hydrogen chloride (4 mol/L, 1,4-dioxane solution, 2 mL) and methanol (2 mL) was stirred at room temperature for 30 minutes. The reaction mixture was concentrated under reduced pressure to give the title compound (400 mg). MS (ESI_APCI, m/z): 281 (M+H)$^+$

Reference Example F-4

1-([1,1'-Biphenyl]-4-yl)-3-(piperidin-4-yl)-1,3-dihydro-2H-imidazo[4,5-b]pyridin-2-one hydrochloride The title compound was prepared in a similar manner to that described in Reference Example F-3 using Reference Example E-4 instead of Reference Example E-3. MS (ESI_APCI, m/z): 371 (M+H)$^+$

Reference Example F-5

1-([1,1'-Biphenyl]-4-yl)-3-(azetidin-3-yl)-1,3-dihydro-2H-imidazo[4,5-b]pyridin-2-one hydrochloride The title compound was prepared in a similar manner to that described in Reference Example F-3 using Reference Example E-5 instead of Reference Example E-3. MS (ESI_APCI, m/z): 343 (M+H)$^+$

Reference Example F-6

Methyl (S)-4-(2-oxo-3-(pyrrolidin-3-yl)-2,3-dihydro-1H-imidazo[4,5-b]pyridin-1-yl)benzoate hydrochloride The title compound was prepared in a similar manner to that described in Reference Example F-1 using Reference Example E-6 instead of Reference Example E-1. MS (ESI_APCI, m/z): 339 (M+H)$^+$

Reference Example F-7

(S)-1-(4-Methoxyphenyl)-3-(pyrrolidin-3-yl)-1,3-dihydro-2H-imidazo[4,5-b]pyridin-2-one hydrochloride The title compound was prepared in a similar manner to that described in Reference Example F-3 using Reference Example E-7 instead of Reference Example E-3.

Reference Example F-8

Methyl (S)-1-([1,1'-biphenyl]-4-yl)-2-oxo-3-(pyrrolidin-3-yl)-2,3-dihydro-1H-imidazo[4,5-b]pyridine-5-carboxylate hydrochloride The title compound was prepared in a similar manner to that described in Reference Example F-3 using Reference Example E-8 instead of Reference Example E-3.

Reference Example F-9

1-([1,1'-Biphenyl]-4-yl)-3-(4-methylpiperidin-4-yl)-1,3-dihydro-2H-imidazo[4,5-b]pyridin-2-one hydrochloride The title compound was prepared in a similar manner to that described in Reference Example F-3 using Reference Example E-9 instead of Reference Example E-3.

Reference Example F-10

Methyl (S)-4'-(6-methoxy-2-oxo-3-(pyrrolidin-3-yl)-2,3-dihydro-1H-imidazo[4,5-b]pyridin-1-yl)-[1,1'-biphenyl]-4-carboxylate hydrochloride The title compound was prepared in a similar manner to that described in Reference Example F-3 using Reference Example E-10 instead of Reference Example E-3.

Reference Example F-11

Methyl 4'-(3-((3R,4R)-4-fluoropyrrolidin-3-yl)-2-oxo-2,3-dihydro-1H-imidazo[4,5-b]pyridin-1-yl)-[1,1'-biphenyl]-4-carboxylate hydrochloride The title compound was prepared in a similar manner to that described in Reference Example F-3 using Reference Example E-11 instead of Reference Example E-3.

Reference Example F-12

Methyl (S)-4'-(2-oxo-3-(pyrrolidin-3-yl)-6-(trifluoromethyl)-2,3-dihydro-1H-imidazo[4,5-b]pyridin-1-yl)-[1,1'-biphenyl]-4-carboxylate hydrochloride The title compound was prepared in a similar manner to that described in Reference Example F-3 using Reference Example E-12 instead of Reference Example E-3.

Reference Example F-13

(S)-1-(3-Methyl-[1,1'-biphenyl]-4-yl)-3-(pyrrolidin-3-yl)-1,3-dihydro-2H-imidazo[4,5-b]pyridin-2-one hydrochloride The title compound was prepared in a similar manner to that described in Reference Example F-1 using Reference Example E-13 instead of Reference Example E-1. MS (ESI_APCI, m/z): 371 (M+H)$^+$

Reference Example F-14

(S)-1-(2'-Methyl-[1,1'-biphenyl]-4-yl)-3-(pyrrolidin-3-yl)-1,3-dihydro-2H-imidazo[4,5-b]pyridin-2-one hydrochloride The title compound was prepared in a similar manner to that described in Reference Example F-1 using Reference Example E-14 instead of Reference Example E-1. MS (ESI_APCI, m/z): 371 (M+H)$^+$

Reference Example F-15

(R)-1-(3-Methyl-[1,1'-biphenyl]-4-yl)-3-(pyrrolidin-3-yl)-1,3-dihydro-2H-imidazo[4,5-b]pyridin-2-one hydrochloride The title compound was prepared in a similar manner to that described in Reference Example F-1 using Reference Example E-15 instead of Reference Example E-1. MS (ESI_APCI, m/z): 371 (M+H)⁺

Reference Example F-16

(S)-1-(4'-Fluoro-[1,1'-biphenyl]-4-yl)-3-(pyrrolidin-3-yl)-1,3-dihydro-2H-imidazo[4,5-b]pyridin-2-one hydrochloride The title compound was prepared in a similar manner to that described in Reference Example F-1 using Reference Example E-16 instead of Reference Example E-1. MS (ESI_APCI, m/z): 375 (M+H)⁺

Reference Example F-17

(S)-1-(4'-Methoxy-[1,1'-biphenyl]-4-yl)-3-(pyrrolidin-3-yl)-1,3-dihydro-2H-imidazo[4,5-b]pyridin-2-one hydrochloride The title compound was prepared in a similar manner to that described in Reference Example F-1 using Reference Example E-17 instead of Reference Example E-1. MS (ESI_APCI, m/z): 387 (M+H)⁺

Reference Example F-18

(S)-3-(Pyrrolidin-3-yl)-1-(2'-(trifluoromethyl)-[1,1'-biphenyl]-4-yl)-1,3-dihydro-2H-imidazo[4,5-b]pyridin-2-one hydrochloride The title compound was prepared in a similar manner to that described in Reference Example F-1 using Reference Example E-18 instead of Reference Example E-1. MS (ESI_APCI, m/z): 425 (M+H)⁺

Reference Example F-19

(S)-4'-(2-Oxo-3-(pyrrolidin-3-yl)-2,3-dihydro-1H-imidazo[4,5-b]pyridin-1-yl)-[1,1'-biphenyl]-4-carbonitrile hydrochloride The title compound was prepared in a similar manner to that described in Reference Example F-1 using Reference Example E-19 instead of Reference Example E-1. MS (ESI_APCI, m/z): 382 (M+H)⁺

Reference Example F-20

(S)-3-(Pyrrolidin-3-yl)-1-(4'-(trifluoromethoxy)-[1,1'-biphenyl]-4-yl)-1,3-dihydro-2H-imidazo[4,5-b]pyridin-2-one hydrochloride The title compound was prepared in a similar manner to that described in Reference Example F-1 using Reference Example E-20 instead of Reference Example E-1. MS (ESI_APCI, m/z): 441 (M+H)⁺

Reference Example F-21

(S)-1-(4'-Hydroxy-[1,1'-biphenyl]-4-yl)-3-(pyrrolidin-3-yl)-1,3-dihydro-2H-imidazo[4,5-b]pyridin-2-one hydrochloride The title compound was prepared in a similar manner to that described in Reference Example F-1 using Reference Example E-21 instead of Reference Example E-1. MS (ESI_APCI, m/z): 373 (M+H)⁺

Reference Example F-22

(S)-1-(4-(Pyridin-4-yl)phenyl)-3-(pyrrolidin-3-yl)-1,3-dihydro-2H-imidazo[4,5-b]pyridin-2-one hydrochloride The title compound was prepared in a similar manner to that described in Reference Example F-1 using Reference Example E-22 instead of Reference Example E-1. MS (ESI_APCI, m/z): 358 (M+H)⁺

Reference Example F-23

Methyl (S)-4'-(2-oxo-3-(pyrrolidin-3-yl)-2,3-dihydro-1H-imidazo[4,5-b]pyridin-1-yl)-[1,1'-biphenyl]-4-carboxylate hydrochloride A mixture of Reference Example E-23 (212 mg) and hydrogen chloride (4 mol/L, 1,4-dioxane solution, 1 mL) was stirred at room temperature for 1 hour. The reaction mixture was concentrated under reduced pressure to give the title compound (205 mg). MS (ESI_APCI, m/z): 415 (M+H)⁺

Reference Example F-24

Methyl (R)-3'-methyl-4'-(2-oxo-3-(pyrrolidin-3-yl)-2,3-dihydro-1H-imidazo[4,5-b]pyridin-1-yl)-[1,1'-biphenyl]-4-carboxylate hydrochloride The title compound was prepared in a similar manner to that described in Reference Example F-1 using Reference Example E-24 instead of Reference Example E-1. MS (ESI_APCI, m/z): 429 (M+H)⁺

Reference Example F-25

Methyl (S)-3'-hydroxy-4'-(2-oxo-3-(pyrrolidin-3-yl)-2,3-dihydro-1H-imidazo[4,5-b]pyridin-1-yl)-[1,1'-biphenyl]-4-carboxylate hydrochloride A mixture of Reference Example E-25 (55 mg), hydrogen chloride (4 mol/L, 1,4-dioxane solution, 1 mL) and methanol (1 mL) was stirred at room temperature for 30 minutes. The reaction mixture was concentrated under reduced pressure to give the title compound (59 mg).

Reference Example F-26

Methyl (S)-2'-hydroxy-4'-(2-oxo-3-(pyrrolidin-3-yl)-2,3-dihydro-1H-imidazo[4,5-b]pyridin-1-yl)-[1,1'-biphenyl]-4-carboxylate hydrochloride A mixture of Reference Example E-26 (122 mg), hydrogen chloride (4 mol/L, 1,4-dioxane solution, 1 mL) and methanol (1 mL) was stirred at room temperature for 30 minutes. The reaction mixture was concentrated under reduced pressure to give the title compound (147 mg).

Reference Example F-27

Methyl (S)-4-(5-(2-oxo-3-(pyrrolidin-3-yl)-2,3-dihydro-1H-imidazo[4,5-b]pyridin-1-yl)pyridin-2-yl)benzoate hydrochloride A mixture of Reference Example E-27 (95 mg), hydrogen chloride (4 mol/L, 1,4-dioxane solution, 1 mL) and methanol (1 mL) was stirred at room temperature for 30 minutes. The reaction mixture was concentrated under reduced pressure to give the title compound (126 mg).

Reference Example F-28

Methyl (S)-4-hydroxy-4'-(2-oxo-3-(pyrrolidin-3-yl)-2,3-dihydro-1H-imidazo[4,5-b]pyridin-1-yl)-[1,1'-biphenyl]-3-carboxylate hydrochloride A mixture of Reference Example E-28 (71 mg) and hydrogen chloride (4 mol/L, 1,4-dioxane solution, 1 mL) was stirred at room temperature for 30 minutes. The reaction mixture was concentrated under reduced pressure to give the title compound (67 mg).

Reference Example F-29

Methyl (S)-2-hydroxy-4'-(2-oxo-3-(pyrrolidin-3-yl)-2,3-dihydro-1H-imidazo[4,5-b]pyridin-1-yl)-[1,1'-biphenyl]-4-carboxylate hydrochloride A mixture of Reference Example E-29 (165 mg), hydrogen chloride (4 mol/L, 1,4-dioxane solution, 1 mL) and methanol (1 mL) was stirred at room temperature for 30 minutes. The reaction mixture was concentrated under reduced pressure to give the title compound (147 mg).

Reference Example F-30

Methyl (S)-3-methyl-4-(5-(2-oxo-3-(pyrrolidin-3-yl)-2,3-dihydro-1H-imidazo[4,5-b]pyridin-1-yl)pyridin-2-yl)benzoate hydrochloride A mixture of Reference Example E-30 (406 mg), hydrogen chloride (4 mol/L, 1,4-dioxane solution, 3 mL) and methanol (2 mL) was stirred at room temperature for 30 minutes. The reaction mixture was concentrated under reduced pressure to give the title compound (308 mg).

Reference Example F-31

(S)-2',4-Dihydroxy-4'-(2-oxo-3-(pyrrolidin-3-yl)-2,3-dihydro-1H-imidazo[4,5-b]pyridin-1-yl)-[1,1'-biphenyl]-3-carbonitrile hydrochloride A mixture of Reference Example E-31 (332 mg), hydrogen chloride (4 mol/L, 1,4-dioxane solution, 3 mL) and methanol (2 mL) was stirred at room temperature for 30 minutes. The reaction mixture was concentrated under reduced pressure to give the title compound (384 mg).

Reference Example F-32

(S)-2-Hydroxy-5-(5-(2-oxo-3-(pyrrolidin-3-yl)-2,3-dihydro-1H-imidazo[4,5-b]pyridin-1-yl)pyridin-2-yl)benzonitrile hydrochloride A mixture of Reference Example E-32 (472 mg), hydrogen chloride (4 mol/L, 1,4-dioxane solution, 2 mL) and methanol (2 mL) was stirred at room temperature for 30 minutes. The reaction mixture was concentrated under reduced pressure to give the title compound (349 mg).

Reference Example F-33

(S)-3',4-Dihydroxy-4'-(2-oxo-3-(pyrrolidin-3-yl)-2,3-dihydro-1H-imidazo[4,5-b]pyridin-1-yl)-[1,1'-biphenyl]-3-carbonitrile hydrochloride A mixture of Reference Example E-33 (77 mg), hydrogen chloride (4 mol/L, 1,4-dioxane solution, 1 mL) and methanol (1 mL) was stirred at room temperature for 30 minutes. The reaction mixture was concentrated under reduced pressure to give the title compound (73 mg).

Reference Example F-34

(S)-1-([1,1'-Biphenyl]-4-yl)-2-oxo-3-(pyrrolidin-3-yl)-N-(tetrahydro-2H-pyran-4-yl)-2,3-dihydro-1H-imidazo[4,5-b]pyridine-5-carboxamide hydrochloride A mixture of Reference Example E-34 (19 mg), hydrogen chloride (4 mol/L, 1,4-dioxane solution, 1 mL) and methanol (1 mL) was stirred at room temperature for 1 hour. The reaction mixture was concentrated under reduced pressure to give the title compound (18 mg).

Reference Example F-35

Methyl (S)-(1-([1,1'-biphenyl]-4-yl)-2-oxo-3-(pyrrolidin-3-yl)-2,3-dihydro-1H-imidazo[4,5-b]pyridine-5-carbonyl)glycinate hydrochloride A mixture of Reference Example E-35 (91 mg), hydrogen chloride (4 mol/L, 1,4-dioxane solution, 1 mL) and methanol (1 mL) was stirred at room temperature for 1 hour. The reaction mixture was concentrated under reduced pressure to give the title compound (79 mg).

Reference Example F-36 Methyl (R)-4-(5-(2-oxo-3-(pyrrolidin-3-yl)-2,3-dihydro-1H-imidazo[4,5-b]pyridin-1-yl)pyridin-2-yl)benzoate hydrochloride A mixture of Reference Example E-36 (377 mg), hydrogen chloride (4 mol/L, 1,4-dioxane solution, 2 mL) and methanol (1 mL) was stirred at room temperature for 1 hour. The reaction mixture was concentrated under reduced pressure to give the title compound (418 mg).

Reference Example F-37

(S)-1-(Naphthalen-2-yl)-3-(pyrrolidin-3-yl)-1,3-dihydro-2H-imidazo[4,5-b]pyridin-2-one hydrochloride The title compound was prepared in a similar manner to that described in Reference Example F-3 using Reference Example E-37 instead of Reference Example E-3.

Reference Example F-38

(S)-1-([1,1'-Biphenyl]-3-yl)-3-(pyrrolidin-3-yl)-1,3-dihydro-2H-imidazo[4,5-b]pyridin-2-one hydrochloride The title compound was prepared in a similar manner to that described in Reference Example F-3 using Reference Example E-38 instead of Reference Example E-3.

Reference Example F-39

Methyl (S)-4'-(6-methyl-2-oxo-3-(pyrrolidin-3-yl)-2,3-dihydro-1H-imidazo[4,5-b]pyridin-1-yl)-[1,1'-biphenyl]-4-carboxylate hydrochloride The title compound was prepared in a similar manner to that described in Reference Example F-3 using Reference Example E-39 instead of Reference Example E-3.

Reference Example G-1

Methyl (S)-2-((3-(1-([1,1'-biphenyl]-4-yl)-2-oxo-1,2-dihydro-3H-imidazo[4,5-b]pyridin-3-yl)pyrrolidin-1-yl)methyl)isonicotinate To a mixture of Reference Example F-1 (30 mg), methyl 2-formylisonicotinate (25 mg) and dichloromethane (1 mL) was added NaBH(OAc)$_3$ (65 mg). The reaction mixture was stirred at room temperature for 30 minutes. To the reaction mixture was added methanol (1 mL), and the mixture was stirred for 30 minutes. The reaction mixture was concentrated under reduced pressure. The residue was purified by column chromatography on amino-silica gel (eluent: n-hexane/ethyl acetate=80/20-45/55) to give the title compound (26 mg). MS (ESI_APCI, m/z): 506 (M+H)$^+$

Reference Example G-2

Methyl (S)-6-((3-(1-([1,1'-biphenyl]-4-yl)-2-oxo-1,2-dihydro-3H-imidazo[4,5-b]pyridin-3-yl)pyrrolidin-1-yl)methyl)nicotinate The title compound was prepared in a similar manner to that described in Reference Example G-1 using methyl 6-formylnicotinate instead of methyl 2-formylisonicotinate. MS (ESI_APCI, m/z): 506 (M+H)$^+$

Reference Example G-3

Methyl (S)-2-((3-(1-(4-methoxyphenyl)-2-oxo-1,2-dihydro-3H-imidazo[4,5-b]pyridin-3-yl)pyrrolidin-1-yl)methyl)isonicotinate The title compound was prepared in a similar manner to that described in Reference Example G-1 using Reference Example F-7 instead of Reference Example F-1. MS (ESI_APCI, m/z): 460 (M+H)$^+$

Reference Example G-4

Methyl (S)-2-((3-(2-oxo-1-phenyl-1,2-dihydro-3H-imidazo[4,5-b]pyridin-3-yl)pyrrolidin-1-yl)methyl)isonicotinate The title compound was prepared in a similar manner to that described in Reference Example G-1 using Reference Example F-3 instead of Reference Example F-1. MS (ESI_APCI, m/z): 430 (M+H)$^+$

Reference Example J-1 tert-Butyl 1-methyl-1H-imidazole-5-carboxylate

A mixture of 1-methyl-1H-imidazole-5-carboxylic acid (5.00 g), tert-butanol (37.7 mL), pyridine (16.0 mL) and TsCl (15.11 g) was stirred at room temperature overnight. To the reaction mixture were added water and ethyl acetate. After stirring, the mixture was extracted with ethyl acetate. The organic layer was washed with water and brine, dried over anhydrous magnesium sulfate, and concentrated under reduced pressure to give the title compound (6.24 g).

Reference Example J-2 tert-Butyl 2-formyl-1-methyl-1H-imidazole-5-carboxylate

To a mixture of Reference Example J-1 (5.82 g), DMF (7.43 mL) and THF (60 mL) was slowly added dropwise LDA (1.0 mol/L, THF/n-hexane solution, 48 mL) at −70° C. or less in dry ice/acetone bath. The reaction mixture was stirred under ice-cooling for 10 minutes. To the reaction mixture were slowly added dropwise LDA (1.0 mol/L, THF/n-hexane solution, 16 mL) and DMF (1 mL) at −70° C. or less in dry ice/acetone bath again. The reaction mixture was stirred under ice-cooling for 10 minutes. To the reaction mixture was added a saturated aqueous solution of ammonium chloride. After stirring for 5 minutes, the mixture was extracted with ethyl acetate. The organic layer was washed with water and brine, dried over anhydrous magnesium sulfate, and concentrated under reduced pressure to give the title compound (6.72 g).

Reference Example G-6 tert-Butyl 2-((4-(1-([1,1'-biphenyl]-4-yl)-2-oxo-1,2-dihydro-3H-imidazo[4,5-b]pyridin-3-yl)-4-methylpiperidin-1-yl)methyl)-1-methyl-1H-imidazole-5-carboxylate To a mixture of Reference Example F-9 (67 mg), THF (1 mL) and triethylamine (0.112 mL) were added Reference Example J-2 (41 mg) and NaBH(OAc)$_3$ (68 mg). The reaction mixture was stirred at room temperature for 1 hour. To the reaction mixture was added methanol, and the mixture was stirred at room temperature for 10 minutes. The reaction mixture was concentrated under reduced pressure. The residue was purified by column chromatography on amino-silica gel (eluent: n-hexane/ethyl acetate=80/20-0/100) to give the title compound (73 mg). MS (ESI_APCI, m/z): 579 (M+H)$^+$

Reference Example G-7 tert-Butyl (S)-2-((3-(6-methoxy-1-(4'-(methoxycarbonyl)-[1,1'-biphenyl]-4-yl)-2-oxo-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-6 using Reference Example F-10 instead of Reference Example F-9. MS (ESI_APCI, m/z): 639 (M+H)$^+$

Reference Example G-8 tert-Butyl 2-(((3R,4R)-3-fluoro-4-(1-(4'-(methoxycarbonyl)-[1,1'-biphenyl]-4-yl)-2-oxo-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-6 using Reference Example F-11 instead of Reference Example F-9. MS (ESI_APCI, m/z): 627 (M+H)⁺

Reference Example G-9 tert-Butyl (S)-2-((3-(1-(4'-(methoxycarbonyl)-[1,1'-biphenyl]-4-yl)-2-oxo-6-(trifluoromethyl)-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-6 using Reference Example F-12 instead of Reference Example F-9. MS (ESI_APCI, m/z): 677 (M+H)⁺

Reference Example G-14

Methyl (S)-2-((3-(1-(4'-(methoxycarbonyl)-[1,1'-biphenyl]-4-yl)-2-oxo-1,2-dihydro-3H-imidazo[4,5-b]pyridin-3-yl)pyrrolidin-1-yl)methyl)isonicotinate The title compound was prepared in a similar manner to that described in Reference Example G-1 using Reference Example F-23 instead of Reference Example F-1. MS (ESI_APCI, m/z): 564 (M+H)⁺

Reference Example G-16

Methyl (S)-2-((3-(1-(2-hydroxy-4'-(methoxycarbonyl)-[1,1'-biphenyl]-4-yl)-2-oxo-1,2-dihydro-3H-imidazo[4,5-b]pyridin-3-yl)pyrrolidin-1-yl)methyl) isonicotinate To a mixture of Reference Example F-26 (200 mg), methyl 2-formylisonicotinate (141 mg) and dichloromethane (2 mL) was added NaBH(OAc)₃ (363 mg). The reaction mixture was stirred at room temperature for 30 minutes. To the reaction mixture was added methanol (2 mL), and the mixture was stirred for 30 minutes. The reaction mixture was concentrated under reduced pressure. The residue was purified by column chromatography on amino-silica gel (eluent: n-hexane/ethyl acetate/methanol=80/20/0-0/100/0-0/80/200) to give the title compound (207 mg). MS (ESI_APCI, m/z): 580 (M+H)⁺

Reference Example G-17

Methyl (S)-2-((3-(1-(6-(4-(methoxycarbonyl)phenyl) pyridin-3-yl)-2-oxo-1,2-dihydro-3H-imidazo[4,5-b] pyridin-3-yl)pyrrolidin-1-yl)methyl)isonicotinate The title compound was prepared in a similar manner to that described in Reference Example G-16 using Reference Example F-27 instead of Reference Example F-26. MS (ESI_APCI, m/z): 565 (M+H)⁺

Reference Example G-18 tert-Butyl (S)-2-((3-(1-(3-hydroxy-4'-(methoxycarbonyl)-[1,1'-biphenyl]-4-yl)-2-oxo-1,2-dihydro-3H-imidazo[4,5-b]pyridin-3-yl)pyrrolidin-1-yl)methyl)-1-methyl-1H-imidazole-5-carboxylate To a mixture of Reference Example F-25 (502 mg), Reference Example J-2 (339 mg) and dichloromethane (3 mL) was added NaBH(OAc)₃ (912 mg). The reaction mixture was stirred at room temperature for 30 minutes. To the reaction mixture was added methanol (2 mL), and the mixture was stirred for 10 minutes. The reaction mixture was concentrated under reduced pressure. The residue was purified by column chromatography on amino-silica gel (eluent: n-hexane/ethyl acetate/methanol=80/20/0-0/100/0-0/90/10) to give the title compound (450 mg). MS (ESI_APCI, m/z): 625 (M+H)⁺

Reference Example G-19 tert-Butyl (S)-2-((3-(1-(6-(4-(methoxycarbonyl)-2-methylphenyl)pyridin-3-yl)-2-oxo-1,2-dihydro-3H-imidazo[4,5-b]pyridin-3-yl)pyrrolidin-1-yl)methyl)-1-methyl-1H-imidazole-5-carboxylate To a mixture of Reference Example F-30 (308 mg), Reference Example J-2 (221 mg) and dichloromethane (3 mL) was added NaBH(OAc)₃ (561 mg). The reaction mixture was stirred at room temperature for 30 minutes. To the reaction mixture was added methanol (3 mL), and the mixture was stirred for 10 minutes. The reaction mixture was concentrated under reduced pressure. The residue was purified by column chromatography on amino-silica gel (eluent: n-hexane/ethyl acetate=80/20-0/100) to give the title compound (558 mg). MS (ESI_APCI, m/z): 624 (M+H)⁺

Reference Example G-20

Methyl (S)-2-((3-(1-(3'-cyano-2,4'-dihydroxy-[1,1'-biphenyl]-4-yl)-2-oxo-1,2-dihydro-3H-imidazo[4,5-b]pyridin-3-yl)pyrrolidin-1-yl)methyl)isonicotinate To a mixture of Reference Example F-31 (150 mg), methyl 2-formylisonicotinate (110 mg) and dichloromethane (2 mL) was added NaBH(OAc)₃ (283 mg). The reaction mixture was stirred at room temperature for 30 minutes. To the reaction mixture was added methanol (2 mL), and the mixture was stirred for 30 minutes. The reaction mixture was concentrated under reduced pressure. The residue was purified by column chromatography on amino-silica gel (eluent: n-hexane/ethyl acetate/methanol=80/20/0-0/100/0-0/50/50) to give the title compound (188 mg). MS (ESI_APCI, m/z): 563 (M+H)⁺

Reference Example G-21

Methyl (S)-2-((3-(1-(6-(3-cyano-4-hydroxyphenyl) pyridin-3-yl)-2-oxo-1,2-dihydro-3H-imidazo[4,5-b] pyridin-3-yl)pyrrolidin-1-yl)methyl)isonicotinate To a mixture of Reference Example F-32 (200 mg), methyl 2-formylisonicotinate (152 mg) and dichloromethane (2 mL) was added NaBH(OAc)₃ (390 mg). The reaction mixture was stirred at room temperature for 30 minutes. To the reaction mixture was added methanol (2 mL), and the mixture was stirred for 10 minutes. The reaction mixture was concentrated under reduced pressure. The residue was purified by column chromatography on amino-silica gel (eluent: n-hexane/ethyl acetate/methanol=80/20/0-0/100/0-

0/50/50) to give the title compound (495 mg). MS (ESI_APCI, m/z): 548 (M+H)$^+$

Reference Example G-22

Methyl (S)-2-((3-(1-(3'-cyano-3,4'-dihydroxy-[1,1'-biphenyl]-4-yl)-2-oxo-1,2-dihydro-3H-imidazo[4,5-b]pyridin-3-yl)pyrrolidin-1-yl)methyl)isonicotinate To a mixture of Reference Example F-33 (63 mg), methyl 2-formylisonicotinate (46 mg) and dichloromethane (2 mL) was added NaBH(OAc)$_3$ (119 mg). The reaction mixture was stirred at room temperature for 30 minutes. To the reaction mixture was added methanol (2 mL), and the mixture was stirred for 10 minutes. The reaction mixture was concentrated under reduced pressure. The residue was purified by column chromatography on amino-silica gel (eluent: n-hexane/ethyl acetate/methanol=80/20/0-0/100/0-0/50/50) to give the title compound (77 mg). MS (ESI_APCI, m/z): 563 (M+H)$^+$ Reference Example G-23 tert-Butyl (S)-1-methyl-2-((3-(1-(naphthalen-2-yl)-2-oxo-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-6 using Reference Example F-37 instead of Reference Example F-9. MS (ESI_APCI, m/z): 525 (M+H)$^+$ Reference Example G-24 tert-Butyl (S)-2-((3-(1-([1,1'-biphenyl]-3-yl)-2-oxo-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-6 using Reference Example F-38 instead of Reference Example F-9. MS (ESI_APCI, m/z): 551 (M+H)$^+$ Reference Example H-1

(S)-3-(Pyrrolidin-3-yl)-1,3-dihydro-2H-imidazo[4,5-b]pyridin-2-one hydrochloride A mixture of Reference Example C-1 (3.00 g), hydrogen chloride (4 mol/L, 1,4-dioxane solution, 10 mL) and methanol (4 mL) was stirred at room temperature for 30 minutes. The reaction mixture was concentrated under reduced pressure to give the title compound (2.80 g).

Reference Example I-1 tert-Butyl (S)-1-methyl-2-((3-(2-oxo-1,2-dihydro-3H-imidazo[4,5-b]pyridin-3-yl)pyrrolidin-1-yl)methyl)-1H-imidazole-5-carboxylate A mixture of Reference Example H-1 (2.68 g), Reference Example J-2 (3.05 g), THF (30 mL) and triethylamine (4.67 mL) was stirred at room temperature for 30 minutes. To the reaction mixture was added NaBH(OAc)$_3$ (3.55 g), and the mixture was stirred at room temperature for 30 minutes. To the reaction mixture was added methanol, and the mixture was stirred at room temperature for 1 hour. The reaction mixture was concentrated under reduced pressure. To the residue were added ethyl acetate and water. After stirring, the mixture was extracted with ethyl acetate. The organic layer was washed with brine, dried over anhydrous magnesium sulfate, and concentrated under reduced pressure. The residue was purified by column chromatography on amino-silica gel (eluent: n-hexane/ethyl acetate/methanol=95/5/0-0/100/0-0/90/10) to give the title compound (3.52 g).

Reference Example G-25 tert-Butyl (S)-2-((3-(1-(4-(dimethylamino)phenyl)-2-oxo-1,2-dihydro-3H-imidazo[4,5-b]pyridin-3-yl)pyrrolidin-1-yl)methyl)-1-methyl-1H-imidazole-5-carboxylate A mixture of Reference Example I-1 (100 mg), 4-bromo-N,N-dimethylaniline (55 mg), N,N'-dimethylethylenediamine (0.032 mL), copper (I) iodide (57 mg), potassium carbonate (83 mg) and acetonitrile (3 mL) was stirred at 100° C. under microwave irradiation for 1 hour. The reaction mixture was poured into ethyl acetate, and the resulting mixture was stirred. The mixture was filtered through Celite, and the filtrate was concentrated under reduced pressure. The residue was purified by column chromatography on amino-silica gel (eluent: n-hexane/ethyl acetate=80/20-20/80) to give the title compound (77 mg). MS (ESI_APCI, m/z): 518 (M+H)$^+$ Reference Example G-26 tert-Butyl (S)-1-methyl-2-((3-(2-oxo-1-(4-phenoxyphenyl)-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-25 using 1-iodo-4-phenoxybenzene instead of 4-bromo-N,N-dimethylaniline. MS (ESI_APCI, m/z): 567 (M+H)$^+$ Reference Example G-27 tert-Butyl (S)-2-((3-(1-(4-benzylphenyl)-2-oxo-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-25 using 1-benzyl-4-iodobenzene instead of 4-bromo-N,N-dimethylaniline. MS (ESI_APCI, m/z): 565 (M+H)$^+$ Reference Example G-28 tert-Butyl (S)-1-methyl-2-((3-(2-oxo-1-(p-tolyl)-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-25 using 1-iodo-4-methylbenzene instead of 4-bromo-N,N-dimethylaniline. MS (ESI_APCI, m/z): 489 (M+H)$^+$

Reference Example G-29 tert-Butyl (S)-2-((3-(1-(4-chlorophenyl)-2-oxo-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-25 using 1-chloro-4-iodobenzene instead of 4-bromo-N,N-dimethylaniline. MS (ESI_APCI, m/z): 509 (M+H)$^+$

Reference Example G-30 tert-Butyl (S)-1-methyl-2-((3-(1-(4-(methylthio)phenyl)-2-oxo-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-25 using 4-iodothioanisole instead of 4-bromo-N,N-dimethylaniline. MS (ESI_APCI, m/z): 521 (M+H)$^+$

Reference Example G-31 tert-Butyl (S)-2-((3-(1-(4-(ethylsulfonyl)phenyl)-2-oxo-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-25 using 1-bromo-4-(ethylsulfonyl)benzene instead of 4-bromo-N,N-dimethylaniline. MS (ESI_APCI, m/z): 567 (M+H)$^+$

Reference Example G-32 tert-Butyl (S)-1-methyl-2-((3-(2-oxo-1-(4-(trifluoromethoxy)phenyl)-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-25 using 1-bromo-4-(trifluoromethoxy)benzene instead of 4-bromo-N,N-dimethylaniline. MS (ESI_APCI, m/z): 559 (M+H)$^+$

Reference Example G-33 tert-Butyl (S)-1-methyl-2-((3-(2-oxo-1-(4-(trifluoromethyl)phenyl)-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-25 using 1-bromo-4-(trifluoromethyl)benzene instead of 4-bromo-N,N-dimethylaniline. MS (ESI_APCI, m/z): 543 (M+H)$^+$

Reference Example G-34 tert-Butyl (S)-2-((3-(1-(4-cyanophenyl)-2-oxo-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-25 using 4-bromobenzonitrile instead of 4-bromo-N,N-dimethylaniline. MS (ESI_APCI, m/z): 500 (M+H)$^+$

Reference Example G-35 tert-Butyl (S)-1-methyl-2-((3-(1-(4-nitrophenyl)-2-oxo-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-25 using 1-bromo-4-nitrobenzene instead of 4-bromo-N,N-dimethylaniline. MS (ESI_APCI, m/z): 520 (M+H)$^+$

Reference Example G-36 tert-Butyl (S)-1-methyl-2-((3-(2-oxo-1-(quinolin-3-yl)-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-25 using 3-bromoquinoline instead of 4-bromo-N,N-dimethylaniline. MS (ESI_APCI, m/z): 526 (M+H)$^+$

Reference Example G-37 tert-Butyl (S)-1-methyl-2-((3-(1-(4-morpholinophenyl)-2-oxo-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-25 using 4-(4-iodophenyl)morpholine instead of 4-bromo-N,N-dimethylaniline.

Reference Example G-38 tert-Butyl (S)-1-methyl-2-((3-(2-oxo-1-(4-phenylcyclohexyl)-1,2-dihydro-3H-imidazo[4,5-b]pyridin-3-yl)pyrrolidin-1-yl)methyl)-1H-imidazole-5-carboxylate To a mixture of Reference Example I-1 (100 mg), 4-phenylcyclohexan-1-ol (44 mg), triphenylphosphine (99 mg) and THF (3 mL) was slowly added DEAD (40% in toluene, 0.171 mL) under ice-cooling with stirring. The reaction mixture was stirred at the same temperature for 10 minutes, and then stirred at room temperature for 2 hours. The reaction mixture was concentrated under reduced pressure. The residue was purified by column chromatography on amino-silica gel (eluent: n-hexane/ethyl acetate=80/20-0/100) to give the title compound (59 mg). MS (ESI_APCI, m/z): 557 (M+H)$^+$

Reference Example G-39 tert-Butyl (S)-1-methyl-2-((3-(2-oxo-1-(4-vinylphenyl)-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-25 using 1-bromo-4-vinylbenzene instead of 4-bromo-N,N-dimethylaniline. MS (ESI_APCI, m/z): 501 (M+H)$^+$

Reference Example G-40 tert-Butyl (S)-1-methyl-2-((3-(2-oxo-1-(thiophen-3-yl)-1,2-dihydro-3H-imidazo[4,5-b]pyridin-3-yl)pyrrolidin-1-yl)methyl)-1H-imidazole-5-carboxylate The title compound was prepared in a similar manner to that described in Reference Example G-25 using 3-bromothiophene instead of 4-bromo-N,N-dimethylaniline. MS (ESI_APCI, m/z): 481 (M+H)$^+$

Reference Example G-41 tert-Butyl (S)-2-((3-(1-benzyl-2-oxo-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-38 using benzyl alcohol instead of 4-phenylcyclohexan-1-ol. MS (ESI_APCI, m/z): 489 (M+H)$^+$

Reference Example G-42 tert-Butyl (S)-2-((3-(1-(4-cyclopropylphenyl)-2-oxo-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-25 using 1-bromo-4-cyclopropylbenzene instead of 4-bromo-N,N-dimethylaniline. MS (ESI_APCI, m/z): 515 (M+H)$^+$

Reference Example G-43 tert-Butyl (S)-2-((3-(1-(4-hydroxyphenyl)-2-oxo-1,2-dihydro-3H-imidazo[4,5-b]pyridin-3-yl)pyrrolidin-1-yl)methyl)-1-methyl-1H-imidazole-5-carboxylate The title compound was prepared in a similar manner to that described in Reference Example G-25 using 4-bromophenol instead of 4-bromo-N,N-dimethylaniline. MS (ESI_APCI, m/z): 491 (M+H)$^+$

Reference Example G-44 tert-Butyl (S)-1-methyl-2-((3-(1-(4'-(methylsulfonamido)-[1,1'-biphenyl]-4-yl)-2-oxo-1,2-dihydro-3H-imidazo[4,5-b]pyridin-3-yl)pyrrolidin-1-yl)methyl)-1H-imidazole-5-carboxylate A mixture of Reference Example G-29 (50 mg), 4-(methylsulfonylamino)phenylboronic acid (25 mg), Pd(amphos)Cl$_2$ (6.8 mg), sodium carbonate (25 mg), DMF (1 mL) and water (0.1 mL) was stirred at 150° C. under microwave irradiation for 1 hour. The reaction mixture was poured into a mixture of water and ethyl acetate. After stirring, the mixture was extracted with ethyl acetate. The organic layer was washed with water and brine, dried over anhydrous magnesium sulfate, and concentrated under reduced pressure. The residue was purified by column chromatography on amino-silica gel (eluent: n-hexane/ethyl acetate/methanol=80/20/0-0/100/0-0/90/10) to give the title compound (37 mg). MS (ESI_APCI, m/z): 644 (M+H)$^+$

Reference Example G-45 tert-Butyl (S)-2-((3-(1-(4'-(methoxycarbonyl)-[1,1'-biphenyl]-4-yl)-6-methyl-2-oxo-1,2-dihydro-3H-imidazo[4,5-b]pyridin-3-yl)pyrrolidin-1-yl)methyl)-1-methyl-1H-imidazole-5-carboxylate To a mixture of Reference Example F-39 (72 mg) and THF (3 mL) were added triethylamine (0.065 mL) and Reference Example J-2 (36 mg). The reaction mixture was stirred at room temperature for 5 minutes. To the reaction mixture was added NaBH(OAc)$_3$ (98 mg), and the mixture was stirred at room temperature for 20 minutes. To the reaction mixture was added methanol, and the mixture was stirred for 5 minutes. The reaction mixture was concentrated under reduced pressure. The residue was purified by column chromatography on amino-silica gel (eluent: n-hexane/ethyl acetate=80/20-30/70) to give the title compound (65 mg). MS (ESI_APCI, m/z): 623 (M+H)$^+$

Reference Example G-46 tert-Butyl (S)-2-((3-(1-([1,1'-biphenyl]-4-yl)-2-oxo-5-((tetrahydro-2H-pyran-4-yl)carbamoyl)-1,2-dihydro-3H-imidazo[4,5-b]pyridin-3-yl)pyrrolidin-1-yl)methyl)-1-methyl-1H-imidazole-5-carboxylate To a mixture of Reference Example F-34 (18 mg), triethylamine (0.024 mL) and THF (1.0 mL) were added Reference Example J-2 (8.7 mg) and NaBH(OAc)$_3$ (15 mg). The reaction mixture was stirred at room temperature for 1 hour. To the reaction mixture was added methanol, and the mixture was stirred for 10 minutes. The reaction mixture was concentrated under reduced pressure. The residue was purified by column chromatography on amino-silica gel (eluent: n-hexane/ethyl acetate=80/20-0/100) to give the title compound (20 mg). MS (ESI_APCI, m/z): 678 (M+H)$^+$

Reference Example G-47 tert-Butyl (S)-2-((3-(1-([1,1'-biphenyl]-4-yl)-5-((2-methoxy-2-oxoethyl)carbamoyl)-2-oxo-1,2-dihydro-3H-imidazo[4,5-b]pyridin-3-yl)pyrrolidin-1-yl)methyl)-1-methyl-1H-imidazole-5-carboxylate To a mixture of Reference Example F-35 (79 mg), triethylamine (0.11 mL) and THF (1.0 mL) were added Reference Example J-2 (40 mg) and NaBH(OAc)$_3$ (67 mg). The reaction mixture was stirred at room temperature for 1 hour. To the reaction mixture was added methanol, and the mixture was stirred for 10 minutes. The reaction mixture was concentrated under reduced pressure. The residue was purified by column chromatography on amino-silica gel (eluent: n-hexane/ethyl acetate=80/20-20/80) to give the title compound (92 mg).

Reference Example K-1

Methyl (S)-(4-(3-(1-((3-methylpyridin-2-yl)methyl)pyrrolidin-3-yl)-2-oxo-2,3-dihydro-1H-imidazo[4,5-b]pyridin-1-yl)benzoyl)glycinate A mixture of Example 21 (50 mg), methyl glycinate hydrochloride (15 mg), EDC-HCl (31 mg), HOBt-H$_2$O (22 mg), triethylamine (0.119 mL) and DMF (1 mL) was stirred at room temperature overnight. To the reaction mixture were added water, ethyl acetate and a saturated aqueous solution of sodium bicarbonate. After stirring, the mixture was extracted with ethyl acetate. The organic layer was washed with brine, dried over anhydrous magnesium sulfate, and concentrated under reduced pressure. The residue was purified by column chromatography on amino-silica gel (eluent: n-hexane/ethyl acetate/methanol=80/20/0-0/100/0-0/90/10) to give the title compound (7 mg). MS (ESI_APCI m/z): 501 (M+H)$^+$ Reference Example K-3 Methyl (5-bromopyridine-2-carbonyl)glycinate A mixture of 5-bromopicolinic acid (300 mg), methyl glycinate hydrochloride (224 mg), EDC-HCl (427 mg), HOBt-H$_2$O (341 mg), triethylamine (1.03 mL) and THF (3 mL) was stirred at room temperature overnight. To the reaction mixture were added water and ethyl acetate, and the mixture was stirred. The mixture was extracted with ethyl acetate. The organic layer was washed with brine, dried over anhydrous magnesium sulfate, and concentrated under reduced pressure. The residue was purified by column chromatography on silica gel (eluent: n-hexane/ethyl acetate=90/10-50/50) to give the title compound (247 mg).

Reference Example K-4 tert-Butyl (S)-2-((3-(1-(6-((2-methoxy-2-oxoethyl)carbamoyl)pyridin-3-yl)-2-oxo-1,2-dihydro-3H-imidazo[4,5-b]pyridin-3-yl)pyrrolidin-1-yl)methyl)-1-methyl-1H-imidazole-5-carboxylate A mixture of Reference Example I-1 (100 mg), Reference Example K-3 (75 mg), N,N'-dimethylethylenediamine (0.032 mL), copper (I) iodide (57 mg), potassium carbonate (83 mg) and acetonitrile (1 mL) was stirred at 100° C. under microwave irradiation for 1 hour. The reaction mixture was poured into ethyl acetate, and the resulting mixture was stirred. The mixture was filtered through Celite, and the filtrate was concentrated under reduced pressure. The residue was purified by column chromatography on amino-silica gel (eluent: n-hexane/ethyl acetate=80/20-0/100) to give the title compound (25 mg). MS (ESI_APCI, m/z): 591 (M+H)$^+$ Chemical structures of some Reference Examples are shown in the following table.

TABLE 1

| Ref. No. | Structure |
| --- | --- |
| C-1 | |
| C-2 | |
| C-3 | 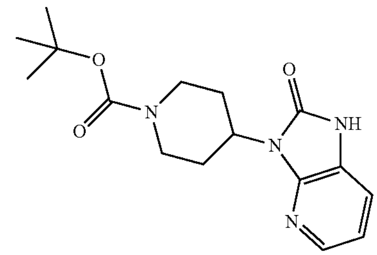 [SMILES: CC(C)(C)OC(=O)N1CCC(n2c(=O)[nH]c3cccnc32)CC1] |
| C-4 | 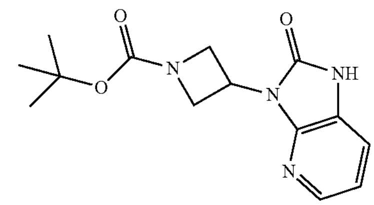 [SMILES: CC(C)(C)OC(=O)N1CC(n2c(=O)[nH]c3cccnc32)C1] |
| C-5 | 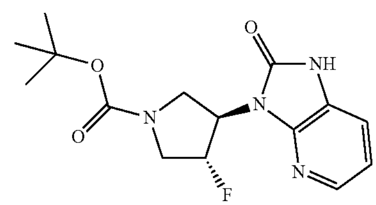 [SMILES: CC(C)(C)OC(=O)N1C[C@@H](F)[C@H](n2c(=O)[nH]c3cccnc32)C1] |
| C-6 | 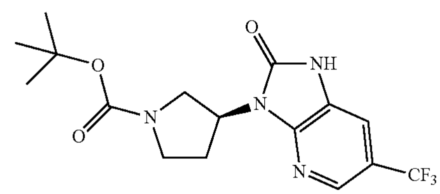 [SMILES: CC(C)(C)OC(=O)N1CC[C@H](n2c(=O)[nH]c3cc(C(F)(F)F)cnc32)C1] |
| C-7 | 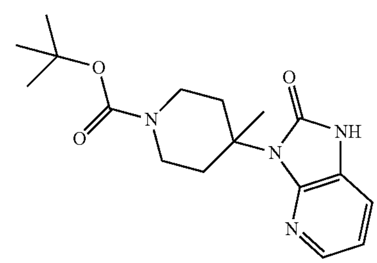 [SMILES: CC(C)(C)OC(=O)N1CCC(C)(n2c(=O)[nH]c3cccnc32)CC1] |
| C-8 | 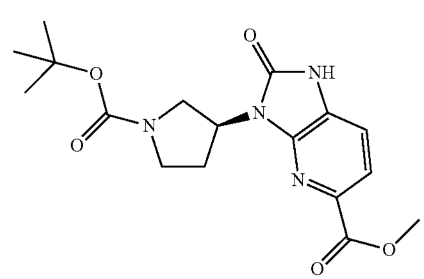 [SMILES: COC(=O)c1ccc2[nH]c(=O)n([C@H]3CCN(C(=O)OC(C)(C)C)C3)c2n1] |
| C-9 | 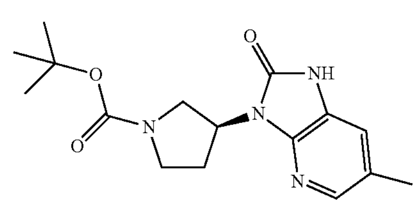 [SMILES: Cc1cnc2c(c1)[nH]c(=O)n2[C@H]1CCN(C(=O)OC(C)(C)C)C1] |

TABLE 1-continued

| Ref. No. | Structure |
|---|---|
| C-10 | (structure) |

Example G-5

Methyl (S)-1-([1,1'-biphenyl]-4-yl)-3-(1-((1-methyl-1H-imidazol-2-yl)methyl)pyrrolidin-3-yl)-2-oxo-2,3-dihydro-1H-imidazo[4,5-b]pyridine-5-carboxylate To a mixture of Reference Example F-8 (105 mg), 1-methyl-1H-imidazole-2-carbaldehyde (51 mg) and dichloromethane (2 mL) was added NaBH(OAc)$_3$ (197 mg). The reaction mixture was stirred at room temperature for 30 minutes. To the reaction mixture was added methanol (2 mL), and the mixture was stirred for 5 minutes. The reaction mixture was concentrated under reduced pressure. The residue was purified by column chromatography on amino-silica gel (eluent: n-hexane/ethyl acetate=80/20-0/100) to give the title compound (128 mg). MS (ESI_APCI, m/z): 509 (M+H)$^+$

Example G-10

Methyl (S)-3'-hydroxy-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylate The title compound was prepared in a similar manner to that described in Example G-5 using Reference Example F-25 instead of Reference Example F-8. MS (ESI_APCI, m/z): 525 (M+H)$^+$

Example G-11

Methyl (S)-2'-hydroxy-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylate The title compound was prepared in a similar manner to that described in Example G-5 using Reference Example F-26 instead of Reference Example F-8. MS (ESI_APCI, m/z): 525 (M+H)$^+$

Example G-12

Methyl (S)-4-(5-(3-(1-((1-methyl-1H-imidazol-2-yl)methyl)pyrrolidin-3-yl)-2-oxo-2,3-dihydro-1H-imidazo[4,5-b]pyridin-1-yl)pyridin-2-yl)benzoate The title compound was prepared in a similar manner to that described in Example G-5 using Reference Example F-27 instead of Reference Example F-8. MS (ESI_APCI, m/z): 510 (M+H)$^+$

Example G-13

Methyl (S)-4-hydroxy-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-3-carboxylate The title compound was prepared in a similar manner to that described in Example G-5 using Reference Example F-28 instead of Reference Example F-8. MS (ESI_APCI, m/z): 525 (M+H)$^+$

Example G-15

Methyl (S)-2-hydroxy-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylate The title compound was prepared in a similar manner to that described in Example G-5 using Reference Example F-29 instead of Reference Example F-8. MS (ESI_APCI, m/z): 525 (M+H)$^+$

Example G-48

Methyl (S)-4'-(3-(1-((3-methylpyridin-2-yl)methyl)pyrrolidin-3-yl)-2-oxo-2,3-dihydro-1H-imidazo[4,5-b]pyridin-1-yl)-[1,1'-biphenyl]-4-carboxylate To a mixture of Reference Example F-23 (100 mg), 3-methyl-2-pyridine carboxyaldehyde (54 mg) and dichloromethane (2 mL) was added NaBH(OAc)$_3$ (282 mg). The reaction mixture was stirred at room temperature for 30 minutes. To the reaction mixture was added methanol (2 mL), and the mixture was stirred for 30 minutes. The reaction mixture was concentrated under reduced pressure. The residue was purified by column chromatography on amino-silica gel (eluent: n-hexane/ethyl acetate=80/20-50/50) to give the title compound (80 mg). MS (ESI_APCI, m/z): 520 (M+H)$^+$

Example K-5

(S)-3-(1-((5-Bromo-1-methyl-1H-imidazol-2-yl)methyl)pyrrolidin-3-yl)-1-(4'-hydroxy-[1,1'-biphenyl]-4-yl)-1,3-dihydro-2H-imidazo[4,5-b]pyridin-2-one To a mixture of Reference Example F-21 (200 mg), 5-bromo-1-methyl-1H-imidazole-2-carbaldehyde (139 mg) and dichloromethane (2 mL) was added NaBH(OAc)$_3$ (415 mg). The reaction mixture was stirred at room temperature for 30 minutes. To the reaction mixture was added methanol (2 mL), and the mixture was stirred for 30 minutes. The reaction mixture was concentrated under reduced pressure. The residue was purified by column chromatography on amino-silica gel (eluent: n-hexane/ethyl acetate=80/20-0/100) to give the title compound (286 mg). MS (ESI_APCI, m/z): 545 (M+H)$^+$

Example K-6

(S)-2-((3-(1-(4'-Hydroxy-[1,1'-biphenyl]-4-yl)-2-oxo-1,2-dihydro-3H-imidazo[4,5-b]pyridin-3-yl)pyrrolidin-1-yl)methyl)-1-methyl-1H-imidazole-5-carbonitrile A mixture of Example K-5 (286 mg), tetrakis(triphenylphosphine)palladium (0) (61 mg), zinc cyanide (123 mg) and NMP (3 mL) was stirred at 150° C. under microwave irradiation for 1 hour. The reaction mixture was poured into a mixture of ethyl acetate and water, and the resulting mixture was stirred. The mixture was filtered through Celite, and the filtrate was extracted with ethyl acetate. The organic layer was washed with brine, dried over anhydrous magnesium sulfate, and concentrated under reduced pressure. The residue was purified by column chromatography on amino-silica gel (eluent: n-hexane/ethyl acetate/methanol=80/20/0-0/100/0-0/90/10) to give the title compound (185 mg). MS (ESI_APCI, m/z): 492 (M+H)$^+$

Example K-7

Methyl (S)-4'-(3-(1-((5-bromo-1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylate To a mixture of Reference Example F-23 (200 mg), 5-bromo-1-methyl-1H-imidazole-2-carbaldehyde (168 mg) and dichloromethane (2 mL) was added NaBH(OAc)$_3$ (376 mg). The reaction mixture was stirred at room temperature for 30 minutes. To the reaction mixture was added methanol (2 mL), and the mixture was stirred for 30 minutes. The reaction mixture was concentrated under reduced pressure. The residue was purified by column chromatography on amino-silica gel (eluent: n-hexane/ethyl acetate=80/20-0/100) to give the title compound (218 mg). MS (ESI_APCI, m/z): 587 (M+H)$^+$

Example K-8

Methyl (S)-4'-(3-(1-((5-cyano-1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylate A mixture of Example K-7 (218 mg), tetrakis(triphenylphosphine)palladium (0) (43 mg), zinc cyanide (87 mg) and NMP (3 mL) was stirred at 150° C. under microwave irradiation for 1 hour. The reaction mixture was poured into a mixture of ethyl acetate and water, and the resulting mixture was stirred. The mixture was filtered through Celite, and the filtrate was extracted with ethyl acetate. The organic layer was washed with brine, dried over anhydrous magnesium sulfate, and concentrated under reduced pressure. The residue was purified by column chromatography on amino-silica gel (eluent: n-hexane/ethyl acetate=80/20-0/100) to give the title compound (319 mg). MS (ESI_APCI, m/z): 534 (M+H)$^+$

Example K-9

Methyl (S)-4'-(3-(1-((5-bromo-1-methyl-1H-imidazol-2-yl)methyl)pyrrolidin-3-yl)-2-oxo-2,3-dihydro-1H-imidazo[4,5-b]pyridin-1-yl)-2'-hydroxy-[1,1'-biphenyl]-4-carboxylate To a mixture of Reference Example F-26 (200 mg), 5-bromo-1-methyl-1H-imidazole-2-carbaldehyde (162 mg) and dichloromethane (3 mL) was added NaBH(OAc)$_3$ (363 mg). The reaction mixture was stirred at room temperature for 30 minutes. To the reaction mixture was added methanol (3 mL), and the mixture was stirred for 30 minutes. The reaction mixture was concentrated under reduced pressure. The residue was purified by column chromatography on amino-silica gel (eluent: n-hexane/ethyl acetate/methanol=80/20/0-0/100/0-0/80/20) to give the title compound (297 mg). MS (ESI_APCI, m/z): 603 (M+H)$^+$

Example K-10

Methyl (S)-4'-(3-(1-((5-cyano-1-methyl-1H-imidazol-2-yl)methyl)pyrrolidin-3-yl)-2-oxo-2,3-dihydro-1H-imidazo[4,5-b]pyridin-1-yl)-2'-hydroxy-[1,1'-biphenyl]-4-carboxylate A mixture of Example K-9 (297 mg), tetrakis(triphenylphosphine)palladium (0) (57 mg), zinc cyanide (116 mg) and NMP (3 mL) was stirred at 150° C. under microwave irradiation for 1 hour. The reaction mixture was poured into a mixture of ethyl acetate and water. After stirring, the mixture was extracted with ethyl acetate. The organic layer was washed with brine, dried over anhydrous magnesium sulfate, and concentrated under reduced pressure. The residue was purified by column chromatography on amino-silica gel (eluent: n-hexane/ethyl acetate/methanol=80/20/0-0/100/0-0/80/20) to give the title compound (178 mg). MS (ESI_APCI, m/z): 550 (M+H)$^+$

Example K-11

Methyl (S)-4-(5-(3-(1-((5-bromo-1-methyl-1H-imidazol-2-yl)methyl)pyrrolidin-3-yl)-2-oxo-2,3-dihydro-1H-imidazo[4,5-b]pyridin-1-yl)pyridin-2-yl)benzoate To a mixture of Reference Example F-27 (200 mg), 5-bromo-1-methyl-1H-imidazole-2-carbaldehyde (167 mg) and dichloromethane (2 mL) was added NaBH(OAc)$_3$ (375 mg). The reaction mixture was stirred at room temperature for 30 minutes. To the reaction mixture was added methanol (2 mL), and the mixture was stirred for 30 minutes. The reaction mixture was concentrated under reduced pressure. The residue was purified by column chromatography on amino-silica gel (eluent: n-hexane/ethyl acetate=80/20-0/100) to give the title compound (214 mg). MS (ESI_APCI, m/z): 588 (M+H)$^+$

Example K-12

Methyl (S)-4-(5-(3-(1-((5-cyano-1-methyl-1H-imidazol-2-yl)methyl)pyrrolidin-3-yl)-2-oxo-2,3-dihydro-1H-imidazo[4,5-b]pyridin-1-yl)pyridin-2-yl)benzoate A mixture of Example K-11 (214 mg), tetrakis(triphenylphosphine)palladium (0) (42 mg), zinc cyanide (86 mg) and NMP (3 mL) was stirred at 150° C. under microwave irradiation for 1 hour. The reaction mixture was poured into a mixture of ethyl acetate and water. After stirring, the mixture was extracted with ethyl acetate. The organic layer was washed with brine, dried over anhydrous magnesium sulfate, and concentrated under reduced pressure. The residue was purified by column chromatography on amino-silica gel (eluent: n-hexane/ethyl acetate=80/20-0/100) to give the title compound (244 mg). MS (ESI_APCI, m/z): 535 (M+H)$^+$

Example K-13

(S)-1-([1,1'-Biphenyl]-4-yl)-3-(1-((5-bromo-1-methyl-1H-imidazol-2-yl)methyl)pyrrolidin-3-yl)-1,3-dihydro-2H-imidazo[4,5-b]pyridin-2-one The title compound was prepared in a similar manner to that described in Example K-11 using Reference Example F-1 instead of Reference Example F-27. MS (ESI_APCI, m/z): 529 (M+H)$^+$

Example K-14

(S)-2-((3-(1-([1,1'-Biphenyl]-4-yl)-2-oxo-1,2-dihydro-3H-imidazo[4,5-b]pyridin-3-yl)pyrrolidin-1-yl)methyl)-1-methyl-1H-imidazole-5-carbonitrile The title compound was prepared in a similar manner to that described in Example K-12 using Example K-13 instead of Example K-11. MS (ESI_APCI, m/z): 476 (M+H)$^+$

Example K-15

(S)-3-(1-((5-Bromo-1-methyl-1H-imidazol-2-yl)methyl)pyrrolidin-3-yl)-1-phenyl-1,3-dihydro-2H-imidazo[4,5-b]pyridin-2-one The title compound was prepared in a similar manner to that described in Example K-11 using Reference Example F-3 instead of Reference Example F-27. MS (ESI_APCI, m/z): 453 (M+H)$^+$

Example K-16

(S)-1-Methyl-2-((3-(2-oxo-1-phenyl-1,2-dihydro-3H-imidazo[4,5-b]pyridin-3-yl)pyrrolidin-1-yl)methyl)-1H-imidazole-5-carbonitrile A mixture of Example K-15 (103 mg), tetrakis(triphenylphosphine)palladium (0) (26 mg), zinc cyanide (53 mg) and DMF (1 mL) was stirred at 150° C. under microwave irradiation for 1 hour. The reaction mixture was poured into a mixture of ethyl acetate and water, and the resulting mixture was stirred. The mixture was filtered through Celite, and the filtrate was extracted with ethyl acetate. The organic layer was washed with brine, dried over anhydrous magnesium sulfate, and concentrated under reduced pressure. The residue was purified by column chromatography on amino-silica gel (eluent: n-hexane/ethyl acetate=80/20-0/100) to give the title compound (75 mg). MS (ESI_APCI, m/z): 400 (M+H)$^+$

Example K-17

Methyl (R)-4-(5-(3-(1-((5-bromo-1-methyl-1H-imidazol-2-yl)methyl)pyrrolidin-3-yl)-2-oxo-2,3-dihydro-1H-imidazo[4,5-b]pyridin-1-yl)pyridin-2-yl)benzoate The title compound was prepared in a similar manner to that described in Example K-11 using Reference Example F-36 instead of Reference Example F-27. MS (ESI_APCI, m/z): 588 (M+H)$^+$

Example K-18

Methyl (R)-4-(5-(3-(1-((5-cyano-1-methyl-1H-imidazol-2-yl)methyl)pyrrolidin-3-yl)-2-oxo-2,3-dihydro-1H-imidazo[4,5-b]pyridin-1-yl)pyridin-2-yl)benzoate The title compound was prepared in a similar manner to that described in Example K-16 using Example K-17 instead of Example K-15. MS (ESI_APCI, m/z): 535 (M+H)$^+$

Example 1

(S)-1-([1,1'-Biphenyl]-4-yl)-3-(1-((3-methylpyridin-2-yl)methyl)pyrrolidin-3-yl)-1,3-dihydro-2H-imidazo[4,5-b]pyridin-2-one To a mixture of Reference Example F-1 (20 mg), 3-methyl-2-pyridine carboxyaldehyde (8.0 mg) and dichloromethane (1 mL) was added NaBH(OAc)$_3$ (65 mg). The reaction mixture was stirred at room temperature for 20 minutes. To the reaction mixture was added methanol (1 mL), and the mixture was stirred for 10 minutes. The reaction mixture was concentrated under reduced pressure. The residue was purified by column chromatography on amino-silica gel (eluent: n-hexane/ethyl acetate=80/20-50/50) to give the title compound (16 mg).

Example 2

(S)-1-([1,1'-biphenyl]-4-yl)-3-(1-((1-methyl-1H-imidazol-2-yl)methyl)pyrrolidin-3-yl)-1,3-dihydro-2H-imidazo[4,5-b]pyridin-2-one To a mixture of Reference Example F-1 (20 mg), 1-methyl-1H-imidazole-2-carbaldehyde (7.2 mg) and dichloromethane (1 mL) was added NaBH(OAc)$_3$ (65 mg). The reaction mixture was stirred at room temperature for 20 minutes. To the reaction mixture was added methanol (1 mL), and the mixture was stirred for 10 minutes. The reaction mixture was concentrated under reduced pressure. The residue was purified by column chromatography on amino-silica gel (eluent: n-hexane/ethyl acetate=80/20-0/100), and then purified by ODS column chromatography (eluent: water/acetonitrile=80/20-30/70) to give the title compound (11 mg).

Example 3

(R)-1-([1,1'-Biphenyl]-4-yl)-3-(1-((1-methyl-1H-imidazol-2-yl)methyl)pyrrolidin-3-yl)-1,3-dihydro-2H-imidazo[4,5-b]pyridin-2-one To a mixture of Reference Example F-2 (20 mg), 1-methyl-1H-imidazole-2-carbaldehyde (11 mg) and dichloromethane (1 mL) was added NaBH(OAc)$_3$ (65 mg). The reaction mixture was stirred at room temperature for 20 minutes. To the reaction mixture was added methanol (1 mL), and the mixture was stirred for 10 minutes. The reaction mixture was concentrated under reduced pressure. The residue was purified by ODS column chromatography (eluent: water/acetonitrile=80/20-30/70) to give the title compound (10 mg).

Example 4

(S)-1-([1,1'-Biphenyl]-4-yl)-3-(1-(pyridin-2-ylmethyl)pyrrolidin-3-yl)-1,3-dihydro-2H-imidazo[4,5-b]pyridin-2-one The title compound was prepared in a similar manner to that described in Example 2 using 2-pyridine carboxyaldehyde instead of 1-methyl-1H-imidazole-2-carbaldehyde.

Example 5

(S)-3-(1-((1H-Imidazol-4-yl)methyl)pyrrolidin-3-yl)-1-([1,1'-biphenyl]-4-yl)-1,3-dihydro-2H-imidazo[4,5-b]pyridin-2-one The title compound was prepared in a similar manner to that described in Example 1 using 1H-imidazole-4-carbaldehyde instead of 3-methyl-2-pyridine carboxyaldehyde.

Example 6

(S)-1-([1,1'-Biphenyl]-4-yl)-3-(1-((1-methyl-1H-imidazol-4-yl)methyl)pyrrolidin-3-yl)-1,3-dihydro-2H-imidazo[4,5-b]pyridin-2-one hydrochloride To a mixture of Reference Example F-1 (30 mg), 1-methyl-1H-imidazole-4-carbaldehyde (17 mg) and dichloromethane (1 mL) was added NaBH(OAc)$_3$ (81 mg). The mixture was stirred at room temperature for 30 minutes. To the reaction mixture was added methanol (1 mL), and the mixture was stirred for 30 minutes. The reaction mixture was concentrated under reduced pressure. The residue was purified by column chromatography on amino-silica gel (eluent: n-hexane/ethyl acetate/methanol=80/20/0-0/100/0-0/90/10). To the obtained product was added hydrogen chloride (1 mol/L, ethanol solution, 0.2 mL), and the mixture was stirred. The mixture was concentrated under reduced pressure to give the title compound (37 mg).

Example 7

(S)-3-(1-((1H-Imidazol-2-yl)methyl)pyrrolidin-3-yl)-1-([1,1'-biphenyl]-4-yl)-1,3-dihydro-2H-imidazo[4,5-b]pyridin-2-one The title compound was prepared in a similar manner to that described in Example 1 using 1H-imidazole-2-carbaldehyde instead of 3-methyl-2-pyridine carboxyaldehyde.

Example 8

(S)-1-([1,1'-Biphenyl]-4-yl)-3-(1-((3-hydroxypyridin-2-yl)methyl)pyrrolidin-3-yl)-1,3-dihydro-2H-imidazo[4,5-b]pyridin-2-one The title compound was prepared in a similar manner to that described in Example 1 using 3-hydroxypyridine-2-carboxyaldehyde instead of 3-methyl-2-pyridine carboxyaldehyde.

Example 9

(S)-1-([1,1'-Biphenyl]-4-yl)-3-(1-((5-hydroxypyridin-2-yl)methyl)pyrrolidin-3-yl)-1,3-dihydro-2H-imidazo[4,5-b]pyridin-2-one The title compound was prepared in a similar manner to that described in Example 1 using 5-hydroxypyridine-2-carboxyaldehyde instead of 3-methyl-2-pyridine carboxyaldehyde.

Example 10

(S)-1-([1,1'-Biphenyl]-4-yl)-3-(1-((4-hydroxypyridin-2-yl)methyl)pyrrolidin-3-yl)-1,3-dihydro-2H-imidazo[4,5-b]pyridin-2-one To a mixture of Reference Example F-1 (30 mg), 4-hydroxypyridine-2-carboxyaldehyde (19 mg) and dichloromethane (1 mL) was added NaBH(OAc)$_3$ (65 mg). The reaction mixture was stirred at room temperature for 30 minutes. To the reaction mixture was added methanol (1 mL), and the mixture was stirred for 30 minutes. The reaction mixture was concentrated under reduced pressure. The residue was purified by ODS column chromatography (eluent: water/acetonitrile=80/20-30/70) to give the title compound (14 mg).

Example 11

(S)-3-(1-((1-Methyl-1H-imidazol-2-yl)methyl)pyrrolidin-3-yl)-1-phenyl-1,3-dihydro-2H-imidazo[4,5-b]pyridin-2-one hydrochloride To a mixture of Reference Example F-3 (100 mg), 1-methyl-1H-imidazole-2-carbaldehyde (70 mg) and dichloromethane (2 mL) was added NaBH(OAc)$_3$ (268 mg). The reaction mixture was stirred at room temperature for 30 minutes. To the reaction mixture was added methanol (2 mL), and the mixture was stirred for 10 minutes. The reaction mixture was concentrated under reduced pressure. The residue was purified by column chromatography on amino-silica gel (eluent: n-hexane/ethyl acetate=80/20-0/100), and then purified by ODS column chromatography (eluent: water/acetonitrile=80/20-30/70). To the obtained product was added hydrogen chloride (4 mol/L, ethyl acetate solution, 2 mL), and the mixture was stirred. The mixture was concentrated under reduced pressure to give the title compound (59 mg).

Example 12

1-([1,1'-Biphenyl]-4-yl)-3-(1-((1-methyl-1H-imidazol-2-yl)methyl)piperidin-4-yl)-1,3-dihydro-2H-imidazo[4,5-b]pyridin-2-one To a mixture of Reference Example F-4 (237 mg), 1-methyl-1H-imidazole-2-carbaldehyde (128 mg) and dichloromethane (3 mL) was added NaBH(OAc)$_3$ (495 mg). The reaction mixture was stirred at room temperature for 30 minutes. To the reaction mixture was added methanol (1 mL), and the mixture was stirred for 10 minutes. To the reaction mixture was added water, and the mixture was stirred. The mixture was extracted with dichloromethane. The organic layer was dried over anhydrous magnesium sulfate, and then concentrated under reduced pressure. The residue was purified by column chromatography on amino-silica gel (eluent: n-hexane/ethyl acetate=80/20-20/80), and then purified by ODS column chromatography (eluent: water/acetonitrile=80/20-30/70) to give the title compound (144 mg).

Example 13

1-([1,1'-Biphenyl]-4-yl)-3-(1-((1-methyl-1H-imidazol-2-yl)methyl)azetidin-3-yl)-1,3-dihydro-2H-imidazo[4,5-b]pyridin-2-one To a mixture of Reference Example F-5 (105 mg), 1-methyl-1H-imidazole-2-carbaldehyde (61 mg) and dichloromethane (2 mL) was added NaBH(OAc)$_3$ (354 mg). The reaction mixture was stirred at room temperature for 30 minutes. To the reaction mixture was added methanol (1 mL), and the mixture was stirred for 10 minutes. The reaction mixture was concentrated under reduced pressure. The residue was purified by ODS column chromatography (eluent: water/acetonitrile=80/20-30/70). To the obtained product were added hydrogen chloride (4 mol/L, ethyl acetate solution) and methanol, and the mixture was stirred. The mixture was concentrated under reduced pressure. The residue was purified by ODS column chromatography (eluent: water/acetonitrile=80/20-30/70) to give the title compound (2.8 mg).

Example 14

(S)-1-(4'-Hydroxy-[1,1'-biphenyl]-4-yl)-3-(1-((1-methyl-1H-imidazol-2-yl)methyl)pyrrolidin-3-yl)-1,3-dihydro-2H-imidazo[4,5-b]pyridin-2-one The title compound was prepared in a similar manner to that described in Example 3 using Reference Example F-21 instead of Reference Example F-2.

Example 15

Methyl (S)-4-(3-(1-((3-methylpyridin-2-yl)methyl)pyrrolidin-3-yl)-2-oxo-2,3-dihydro-1H-imidazo[4,5-b]pyridin-1-yl)benzoate The title compound was prepared in a similar manner to that described in Example 1 using Reference Example F-6 instead of Reference Example F-1.

Example 16

(S)-2-((3-(1-([1,1'-Biphenyl]-4-yl)-2-oxo-1,2-dihydro-3H-imidazo[4,5-b]pyridin-3-yl)pyrrolidin-1-yl)methyl)isonicotinic acid To a mixture of Reference Example G-1 (26 mg), methanol (0.5 mL) and THF (0.5 mL) was added an aqueous solution of sodium hydroxide (5 mol/L, 1 mL). The reaction mixture was stirred at room temperature overnight. The reaction mixture was neutralized with hydrochloric acid (2 mol/L). The mixture was purified by ODS column chromatography (eluent: water/acetonitrile=90/10-30/70) to give the title compound (9.5 mg).

Example 17

(S)-6-((3-(1-([1,1'-Biphenyl]-4-yl)-2-oxo-1,2-dihydro-3H-imidazo[4,5-b]pyridin-3-yl)pyrrolidin-1-yl)methyl)nicotinic acid The title compound was prepared in a similar manner to that described in Example 16 using Reference Example G-2 instead of Reference Example G-1.

Example 18

(S)-2-((3-(1-(4-Methoxyphenyl)-2-oxo-1,2-dihydro-3H-imidazo[4,5-b]pyridin-3-yl)pyrrolidin-1-yl)methyl)isonicotinic acid The title compound was prepared in a similar manner to that described in Example 16 using Reference Example G-3 instead of Reference Example G-1.

Example 19

(S)-2-((3-(2-Oxo-1-phenyl-1,2-dihydro-3H-imidazo[4,5-b]pyridin-3-yl)pyrrolidin-1-yl)methyl)isonicotinic acid The title compound was prepared in a similar manner to that described in Example 16 using Reference Example G-4 instead of Reference Example G-1.

Example 20

(S)-1-([1,1'-Biphenyl]-4-yl)-3-(1-((1-methyl-1H-imidazol-2-yl)methyl)pyrrolidin-3-yl)-2-oxo-2,3-dihydro-1H-imidazo[4,5-b]pyridine-5-carboxylic acid To a mixture of Example G-5 (118 mg), methanol (0.5 mL) and THF (0.5 mL) was added an aqueous solution of sodium hydroxide (5 mol/L, 1 mL). The reaction mixture was stirred at room temperature overnight. The reaction mixture was neutralized with hydrochloric acid (2 mol/L), and the mixture was stirred for 20 minutes. The precipitate was collected by filtration, and the obtained solid was dried to give the title compound (44 mg).

Example 21

(S)-4-(3-(1-((3-Methylpyridin-2-yl)methyl)pyrrolidin-3-yl)-2-oxo-2,3-dihydro-1H-imidazo[4,5-b]pyridin-1-yl)benzoic acid hydrochloride To a mixture of Example 15 (257 mg), methanol (1 mL) and THF (1 mL) was added an aqueous solution of sodium hydroxide (5 mol/L, 2 mL). The reaction mixture was stirred at room temperature for 3 hours. The reaction mixture was neutralized by the addition of hydrochloric acid (2 mol/L, 5 mL). The mixture was concentrated under reduced pressure. To the residue were added dichloromethane and anhydrous magnesium sulfate. The mixture was stirred at room temperature for 10 minutes. The mixture was filtered through Celite, and the filtrate was concentrated under reduced pressure. To the residue were added dichloromethane and hydrogen chloride (4 mol/L, ethyl acetate solution, 1 mL), and the mixture was stirred. The mixture was concentrated under reduced pressure to give the title compound (120 mg).

Example 22

(S)-1-Methyl-2-((3-(1-(naphthalen-2-yl)-2-oxo-1,2-dihydro-3H-imidazo[4,5-b]pyridin-3-yl)pyrrolidin-1-yl)methyl)-1H-imidazole-5-carboxylic acid To a mixture of Reference Example G-23 (154 mg), ethyl acetate (1 mL) and methanol (0.5 mL) was added hydrogen chloride (4 mol/L, ethyl acetate solution, 2 mL). The reaction mixture was refluxed for 2 hours. The reaction mixture was allowed to cool to room temperature, and then concentrated under reduced pressure. The residue was purified by ODS column chromatography (eluent: water with 0.1% formic acid/acetonitrile=90/10-30/70) to give the title compound (107 mg).

Example 23

2-((4-(1-([1,1'-Biphenyl]-4-yl)-2-oxo-1,2-dihydro-3H-imidazo[4,5-b]pyridin-3-yl)-4-methylpiperidin-1-yl)methyl)-1-methyl-1H-imidazole-5-carboxylic acid A mixture of Reference Example G-6 (73 mg), dichloromethane (0.5 mL) and trifluoroacetic acid (0.5 mL) was refluxed for 1 hour. The reaction mixture was allowed to cool to room temperature, and then concentrated under reduced pressure. The residue was purified by ODS column chromatography (eluent: water with 0.1% formic acid/acetonitrile=90/10-30/70) to give the title compound (39 mg).

Example 24

(S)-2-((3-(1-(4'-Carboxy-[1,1'-biphenyl]-4-yl)-6-methoxy-2-oxo-1,2-dihydro-3H-imidazo[4,5-b]pyridin-3-yl)pyrrolidin-1-yl)methyl)-1-methyl-1H-imidazole-5-carboxylic acid A mixture of Reference Example G-7 (145 mg), water (0.5 mL) and concentrated sulfuric acid (0.024 mL) was stirred at 90° C. for 3 hours. The reaction mixture was allowed to cool to room temperature. To the mixture were added methanol (0.5 mL) and lithium hydroxide monohydrate (95 mg). The reaction mixture was stirred at room temperature overnight. The reaction mixture was purified by ODS column chromatography (eluent: water with 0.1% formic acid/acetonitrile=90/10-30/70) to give the title compound (85 mg).

Example 25

2-(((3R,4R)-3-(1-(4'-Carboxy-[1,1'-biphenyl]-4-yl)-2-oxo-1,2-dihydro-3H-imidazo[4,5-b]pyridin-3-yl)-4-fluoropyrrolidin-1-yl)methyl)-1-methyl-1H-imidazole-5-carboxylic acid The title compound was prepared in a similar manner to that described in Example 24 using Reference Example G-8 instead of Reference Example G-7.

Example 26

(S)-2-((3-(1-(4'-Carboxy-[1,1'-biphenyl]-4-yl)-2-oxo-6-(trifluoromethyl)-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 24 using Reference Example G-9 instead of Reference Example G-7.

Example 27

(S)-2-((3-(1-(4'-Carboxy-[1,1'-biphenyl]-4-yl)-6-methyl-2-oxo-1,2-dihydro-3H-imidazo[4,5-b]pyridin-3-yl)pyrrolidin-1-yl)methyl)-1-methyl-1H-imidazole-5-carboxylic acid A mixture of Reference Example G-45 (65 mg), methanol (0.2 mL), water (1 mL) and concentrated sulfuric acid (0.04 mL) was stirred at 110° C. under microwave irradiation for 1 hour. To the reaction mixture was added lithium hydroxide monohydrate (100 mg), and the mixture was stirred at 50° C. for 1 hour. The reaction mixture was purified by ODS column chromatography (eluent: water with 0.1% formic acid/acetonitrile=90/10-30/70) to give the title compound (27 mg).

Example 28

(S)-3-(1-((1-Methyl-1H-imidazol-2-yl)methyl)pyrrolidin-3-yl)-1-(3-methyl-[1,1'-biphenyl]-4-yl)-1,3-dihydro-2H-imidazo[4,5-b]pyridin-2-one The title compound was prepared in a similar manner to that described in Example 3 using Reference Example F-13 instead of Reference Example F-2.

Example 29

(S)-3-(1-((1-Methyl-1H-imidazol-2-yl)methyl)pyrrolidin-3-yl)-1-(2'-methyl-[1,1'-biphenyl]-4-yl)-1,3-dihydro-2H-imidazo[4,5-b]pyridin-2-one The title compound was prepared in a similar manner to that described in Example 3 using Reference Example F-14 instead of Reference Example F-2.

Example 30

(R)-3-(1-((1-Methyl-1H-imidazol-2-yl)methyl)pyrrolidin-3-yl)-1-(3-methyl-[1,1'-biphenyl]-4-yl)-1,3-dihydro-2H-imidazo[4,5-b]pyridin-2-one The title compound was prepared in a similar manner to that described in Example 3 using Reference Example F-15 instead of Reference Example F-2.

Example 31

(S)-1-(4'-Fluoro-[1,1'-biphenyl]-4-yl)-3-(1-((3-methylpyridin-2-yl)methyl)pyrrolidin-3-yl)-1,3-dihydro-2H-imidazo[4,5-b]pyridin-2-one The title compound was prepared in a similar manner to that described in Example 1 using Reference Example F-16 instead of Reference Example F-1.

Example 32

(S)-1-(4'-Methoxy-[1,1'-biphenyl]-4-yl)-3-(1-((3-methylpyridin-2-yl)methyl)pyrrolidin-3-yl)-1,3-dihydro-2H-imidazo[4,5-b]pyridin-2-one The title compound was prepared in a similar manner to that described in Example 1 using Reference Example F-17 instead of Reference Example F-1.

Example 33

(S)-3-(1-((3-Methylpyridin-2-yl)methyl)pyrrolidin-3-yl)-1-(2'-(trifluoromethyl)-[1,1'-biphenyl]-4-yl)-1,3-dihydro-2H-imidazo[4,5-b]pyridin-2-one The title compound was prepared in a similar manner to that described in Example 1 using Reference Example F-18 instead of Reference Example F-1.

Example 34

(S)-4'-(3-(1-((3-Methylpyridin-2-yl)methyl)pyrrolidin-3-yl)-2-oxo-2,3-dihydro-1H-imidazo[4,5-b]pyridin-1-yl)-[1,1'-biphenyl]-4-carbonitrile The title compound was prepared in a similar manner to that described in Example 1 using Reference Example F-19 instead of Reference Example F-1.

Example 35

(S)-3-(1-((3-Methylpyridin-2-yl)methyl)pyrrolidin-3-yl)-1-(4'-(trifluoromethoxy)-[1,1'-biphenyl]-4-yl)-1,3-dihydro-2H-imidazo[4,5-b]pyridin-2-one The title compound was prepared in a similar manner to that described in Example 1 using Reference Example F-20 instead of Reference Example F-1.

Example 36

(S)-3-(1-((1-Methyl-1H-imidazol-2-yl)methyl)pyrrolidin-3-yl)-1-(4-(pyridin-4-yl)phenyl)-1,3-dihydro-2H-imidazo[4,5-b]pyridin-2-one hydrochloride To a mixture of Reference Example F-22 (43 mg), 1-methyl-1H-imidazole-2-carbaldehyde (22 mg) and dichloromethane (1 mL) was added NaBH(OAc)₃ (127 mg). The reaction mixture was stirred at room temperature for 30 minutes. To the reaction mixture was added methanol (1 mL), and the mixture was stirred for 30 minutes. The reaction mixture was concentrated under reduced pressure. The residue was purified by ODS column chromatography (eluent: water/acetonitrile=80/20-30/70). To the obtained product were added hydrogen chloride (4 mol/L, ethyl acetate solution) and methanol, and the mixture was stirred. The mixture was concentrated under reduced pressure to give the title compound (25 mg).

Example 37

Methyl (S)-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylate The title compound was prepared in a similar manner to that described in Example 3 using Reference Example F-23 instead of Reference Example F-2.

Example 38

Methyl (R)-3'-methyl-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylate The title compound was prepared in a similar manner to that described in Example 3 using Reference Example F-24 instead of Reference Example F-2.

Example 39

(S)-3'-Hydroxy-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylic acid A mixture of Example G-10 (20 mg), methanol (0.5 mL), THF (0.5 mL) and an aqueous solution of sodium hydroxide (5 mol/L, 1 mL) was stirred at room temperature overnight. To the reaction mixture was added hydrochloric acid (2 mol/L, 2.5 mL), and the mixture was stirred. The mixture was concentrated under reduced pressure. To the residue was added methanol, and the mixture was stirred. The mixture was filtered through Celite, and the filtrate was concentrated under reduced pressure. The residue was purified by ODS column chromatography (eluent: water/acetonitrile=90/10-30/70) to give the title compound (6.3 mg).

Example 40

(S)-2'-Hydroxy-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylic acid The title compound was prepared in a similar manner to that described in Example 39 using Example G-11 instead of Example G-10.

Example 41

(S)-4-(5-(3-(1-((1-Methyl-1H-imidazol-2-yl)methyl)pyrrolidin-3-yl)-2-oxo-2,3-dihydro-1H-imidazo[4,5-b]pyridin-1-yl)pyridin-2-yl)benzoic acid The title compound was prepared in a similar manner to that described in Example 39 using Example G-12 instead of Example G-10.

Example 42

(S)-4-Hydroxy-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-3-carboxylic acid The title compound was prepared in a similar manner to that described in Example 16 using Example G-13 instead of Reference Example G-1.

Example 43

(S)-2-((3-(1-(4'-Carboxy-[1,1'-biphenyl]-4-yl)-2-oxo-1,2-dihydro-3H-imidazo[4,5-b]pyridin-3-yl)pyrrolidin-1-yl)methyl)isonicotinic acid The title compound was prepared in a similar manner to that described in Example 16 using Reference Example G-14 instead of Reference Example G-1.

Example 44

(S)-2-Hydroxy-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylic acid The title compound was prepared in a similar manner to that described in Example 16 using Example G-15 instead of Reference Example G-1.

Example 45

(S)-2-((3-(1-(4'-Carboxy-2-hydroxy-[1,1'-biphenyl]-4-yl)-2-oxo-1,2-dihydro-3H-imidazo[4,5-b]pyridin-3-yl)pyrrolidin-1-yl)methyl)isonicotinic acid To a mixture of Reference Example G-16 (207 mg), methanol (0.5 mL) and THF (0.5 mL) was added an aqueous solution of sodium hydroxide (5 mol/L, 1 mL). The reaction mixture was stirred at room temperature overnight. The reaction mixture was neutralized with hydrochloric acid. The mixture was purified by ODS column chromatography (eluent: water/acetonitrile=98/2-30/70) to give the title compound (109 mg).

Example 46

(S)-2-((3-(1-(6-(4-Carboxyphenyl)pyridin-3-yl)-2-oxo-1,2-dihydro-3H-imidazo[4,5-b]pyridin-3-yl)pyrrolidin-1-yl)methyl)isonicotinic acid To a mixture of Reference Example G-17 (455 mg), methanol (0.5 mL) and THF (0.5 mL) was added an aqueous solution of sodium hydroxide (5 mol/L, 1 mL). The reaction mixture was stirred at room temperature overnight. The reaction mixture was neutralized by the addition of hydrochloric acid (2 mol/L), and the precipitate was collected by filtration. The obtained solid was purified by ODS column chromatography (eluent: water/acetonitrile=98/2-30/70) to give the title compound (280 mg).

Example 47

(S)-4'-(3-(1-((1-Methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylic acid To a mixture of Example 37 (48 mg), methanol (0.5 mL) and THF (0.5 mL) was added an aqueous solution of sodium hydroxide (5 mol/L, 1 mL). The reaction mixture was stirred at room temperature for 4 hours. To the reaction mixture was added hydrochloric acid (2 mol/L, 2.5 mL), and the mixture was stirred. The mixture was concentrated under reduced pressure. To the residue was added methanol, and the mixture was stirred. The insoluble material was removed through Celite, and the filtrate was concentrated under reduced pressure. The residue was purified by ODS column chromatography (eluent: water/acetonitrile=90/10-30/70) to give the title compound (17 mg).

Example 48

(R)-3'-Methyl-4'-(3-(1-((1-methyl-1H-imidazol-2-yl)methyl)pyrrolidin-3-yl)-2-oxo-2,3-dihydro-1H-imidazo[4,5-b]pyridin-1-yl)-[1,1'-biphenyl]-4-carboxylic acid The title compound was prepared in a similar manner to that described in Example 47 using Example 38 instead of Example 37.

Example 49

(S)-2-((3-(1-(4'-Carboxy-3-hydroxy-[1,1'-biphenyl]-4-yl)-2-oxo-1,2-dihydro-3H-imidazo[4,5-b]pyridin-3-yl)pyrrolidin-1-yl)methyl)-1-methyl-1H-imidazole-5-carboxylic acid A mixture of Reference Example G-18 (450 mg) and concentrated hydrochloric acid (2 mL) was stirred at 110° C. under microwave irradiation for 1 hour. The reaction mixture was allowed to stand at room temperature, and the precipitate was collected by filtration. The obtained solid was washed with cold water, and dried. A part of the obtained product (26 mg, out of 222 mg) was purified by ODS column chromatography (eluent: water with 0.10% formic acid/acetonitrile=98/2-30/70) to give the title compound (15 mg).

Example 50

(S)-2-((3-(1-(6-(4-Carboxy-2-methylphenyl)pyridin-3-yl)-2-oxo-1,2-dihydro-3H-imidazo[4,5-b]pyridin-3-yl)pyrrolidin-1-yl)methyl)-1-methyl-1H-imidazole-5-carboxylic acid A mixture of Reference Example G-19 (413 mg) and concentrated hydrochloric acid (2 mL) was stirred at 110° C. under microwave irradiation for 1 hour. The reaction mixture was neutralized with the addition of an aqueous solution of sodium hydroxide (5 mol/L). The insoluble material was removed by filtration. The filtrate was purified by ODS column chromatography (eluent: water with 0.1% formic acid/acetonitrile=90/10-70/30-10/90) to give the title compound (224 mg).

Example 51

(S)-2-((3-(1-(3'-Carboxy-2,4'-dihydroxy-[1,1'-biphenyl]-4-yl)-2-oxo-1,2-dihydro-3H-imidazo[4,5-b]pyridin-3-yl)pyrrolidin-1-yl)methyl)isonicotinic acid A mixture of Reference Example G-20 (188 mg) and concentrated hydrochloric acid (1 mL) was stirred at 110° C. under microwave irradiation for 1 hour. To the reaction mixture was added concentrated sulfuric acid (0.2 mL) under ice-cooling with stirring. The reaction mixture was refluxed for 4 days. The reaction mixture was allowed to cool to room temperature, and then the mixture was neutralized by the addition of an aqueous solution of sodium hydroxide (5 mol/L). The precipitate was collected by filtration. The obtained solid was purified by ODS column chromatography (eluent: water/acetonitrile=98/2-30/70) to give the title compound (16 mg).

Example 52

(S)-2-((3-(1-(6-(3-Carboxy-4-hydroxyphenyl)pyridin-3-yl)-2-oxo-1,2-dihydro-3H-imidazo[4,5-b]pyridin-3-yl)pyrrolidin-1-yl)methyl)isonicotinic acid The title compound was prepared in a similar manner to that described in Example 51 using Reference Example G-21 instead of Reference Example G-20.

Example 53

(S)-2-((3-(1-(3'-Carboxy-3,4'-dihydroxy-[1,1'-biphenyl]-4-yl)-2-oxo-1,2-dihydro-3H-imidazo[4,5-b]pyridin-3-yl)pyrrolidin-1-yl)methyl)isonicotinic acid A mixture of Reference Example G-22 (77 mg), water (0.5 mL) and concentrated sulfuric acid (0.5 mL) was refluxed for 7 hours. The reaction mixture was allowed to cool to room temperature. To the mixture was added an aqueous solution of sodium hydroxide (5 mol/L, 4 mL) under ice-cooling. The mixture was stirred at room temperature overnight. The reaction mixture was purified by ODS column chromatography (eluent: water/acetonitrile=98/2-30/70) to give the title compound (3 mg).

Example 54

(S)-2-((3-(1-([1,1'-Biphenyl]-3-yl)-2-oxo-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 23 using Reference Example G-24 instead of Reference Example G-6.

Example 55

(S)-2-((3-(1-(4-(Dimethylamino)phenyl)-2-oxo-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 23 using Reference Example G-25 instead of Reference Example G-6.

Example 56

(S)-1-Methyl-2-((3-(2-oxo-1-(4-phenoxyphenyl)-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-26 instead of Reference Example G-6.

Example 57

(S)-2-((3-(1-(4-Benzylphenyl)-2-oxo-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 23 using Reference Example G-27 instead of Reference Example G-6.

Example 58

(S)-1-Methyl-2-((3-(2-oxo-1-(p-tolyl)-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-28 instead of Reference Example G-6.

Example 59

(S)-2-((3-(1-(4-Chlorophenyl)-2-oxo-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 23 using Reference Example G-29 instead of Reference Example G-6.

Example 60

(S)-1-Methyl-2-((3-(1-(4-(methylthio)phenyl)-2-oxo-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-30 instead of Reference Example G-6.

Example 61

(S)-2-((3-(1-(4-(Ethylsulfonyl)phenyl)-2-oxo-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 23 using Reference Example G-31 instead of Reference Example G-6.

Example 62

(S)-1-Methyl-2-((3-(2-oxo-1-(4-(trifluoromethoxy)phenyl)-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-32 instead of Reference Example G-6.

Example 63

(S)-1-Methyl-2-((3-(2-oxo-1-(4-(trifluoromethyl)phenyl)-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-33 instead of Reference Example G-6.

Example 64

(S)-2-((3-(1-(4-Cyanophenyl)-2-oxo-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 23 using Reference Example G-34 instead of Reference Example G-6.

Example 65

(S)-1-Methyl-2-((3-(1-(4-nitrophenyl)-2-oxo-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-35 instead of Reference Example G-6.

Example 66

(S)-1-Methyl-2-((3-(2-oxo-1-(quinolin-3-yl)-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-36 instead of Reference Example G-6.

Example 67

(S)-1-Methyl-2-((3-(1-(4-morpholinophenyl)-2-oxo-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-37 instead of Reference Example G-6.

Example 68

(S)-1-Methyl-2-((3-(2-oxo-1-(4-phenylcyclohexyl)-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-38 instead of Reference Example G-6.

Example 69

(S)-1-Methyl-2-((3-(2-oxo-1-(4-vinylphenyl)-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-39 instead of Reference Example G-6.

Example 70

(S)-1-Methyl-2-((3-(2-oxo-1-(thiophen-3-yl)-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-40 instead of Reference Example G-6.

Example 71

(S)-2-((3-(1-Benzyl-2-oxo-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 23 using Reference Example G-41 instead of Reference Example G-6.

Example 72

(S)-2-((3-(1-(4-Cyclopropylphenyl)-2-oxo-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 23 using Reference Example G-42 instead of Reference Example G-6.

Example 73

(S)-2-((3-(1-(4-Hydroxyphenyl)-2-oxo-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 23 using Reference Example G-43 instead of Reference Example G-6.

Example 74

(S)-1-Methyl-2-((3-(1-(4'-(methylsulfonamido)-[1,1'-biphenyl]-4-yl)-2-oxo-1,2-dihydro-3H-imidazo[4,5-b]pyridin-3-yl)pyrrolidin-1-yl)methyl)-1H-imidazole-5-carboxylic acid The title compound was prepared in a similar manner to that described in Example 23 using Reference Example G-44 instead of Reference Example G-6.

Example 75

(S)-(4-(3-(1-((3-Methylpyridin-2-yl)methyl)pyrrolidin-3-yl)-2-oxo-2,3-dihydro-1H-imidazo[4,5-b]pyridin-1-yl)benzoyl)glycine To a mixture of Reference Example K-1 (7.7 mg), methanol (0.5 mL) and THF (0.5 mL) was added an aqueous solution of sodium hydroxide (5 mol/L, 1 mL). The reaction mixture was stirred at room temperature for 6 hours. The reaction mixture was purified by ODS column chromatography (eluent: water/acetonitrile=90/10-30/70) to give the title compound (2.5 mg).

Example 76

(S)-2-((3-(1-([1,1'-Biphenyl]-4-yl)-2-oxo-5-((tetrahydro-2H-pyran-4-yl)carbamoyl)-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 23 using Reference Example G-46 instead of Reference Example G-6.

Example 77

(S)-2-((3-(1-([1,1'-Biphenyl]-4-yl)-5-((carboxymethyl)carbamoyl)-2-oxo-1,2-dihydro-3H-imidazo[4,5-b]pyridin-3-yl)pyrrolidin-1-yl)methyl)-1-methyl-1H-imidazole-5-carboxylic acid A mixture of Reference Example G-47 (92 mg), methanol (0.5 mL), water (0.5 mL) and concentrated sulfuric acid (0.022 mL) was refluxed for 1 hour. The reaction mixture was allowed to cool to room temperature. To the mixture was added lithium hydroxide monohydrate (70 mg), and the mixture was stirred at room temperature overnight. The reaction mixture was purified by ODS column chromatography (eluent: water with 0.1% formic acid/acetonitrile=98/2-30/70) to give the title compound (33 mg).

Example 78

(S)-2-((3-(1-(6-(((Carboxymethyl)carbamoyl)pyridin-3-yl)-2-oxo-1,2-dihydro-3H-imidazo[4,5-b]pyridin-3-yl)pyrrolidin-1-yl)methyl)-1-methyl-1H-imidazole-5-carboxylic acid The title compound was prepared in a similar manner to that described in Example 77 using Reference Example K-4 instead of Reference Example G-47.

Example 79

(S)-3-(1-((5-Bromo-1-methyl-1H-imidazol-2-yl)methyl)pyrrolidin-3-yl)-1-(4-(pyridin-4-yl)phenyl)-1,3-dihydro-2H-imidazo[4,5-b]pyridin-2-one To a mixture of Reference Example F-22 (285 mg), 5-bromo-1-methyl-1H-imidazole-2-carbaldehyde (250 mg) and dichloromethane (2 mL) was added NaBH(OAc)$_3$ (561 mg). The reaction mixture was stirred at room temperature for 30 minutes. To the reaction mixture was added methanol (2 mL), and the mixture was stirred for 30 minutes. The reaction mixture was concentrated under reduced pressure. The residue was purified by column chromatography on amino-silica gel (eluent: n-hexane/ethyl acetate=80/20-0/100) to give the title compound (363 mg).

Example 80

(S)-1-Methyl-2-((3-(2-oxo-1-(4-(pyridin-4-yl)phenyl)-1,2-dihydro-3H-imidazo[4,5-b]pyridin-3-yl)pyrrolidin-1-yl)methyl)-1H-imidazole-5-carbonitrile A mixture of Example 79 (351 mg), tetrakis(triphenylphosphine)palladium (0) (77 mg), zinc cyanide (155 mg) and NMP (3 mL) was stirred at 120° C. under microwave irradiation for 90 minutes. The reaction mixture was poured into a mixture of ethyl acetate and water, and the resulting mixture was stirred. The mixture was filtered through Celite, and the filtrate was extracted with ethyl acetate. The organic layer was washed with brine, dried over anhydrous magnesium sulfate, and concentrated under reduced pressure. The residue was purified by column chromatography on amino-silica gel (eluent: n-hexane/ethyl acetate/methanol=80/20/0-0/100/0-0/90/10) to give the title compound (68 mg).

Example 81

(S)-1-Methyl-2-((3-(2-oxo-1-(4-(pyridin-4-yl)phenyl)-1,2-dihydro-3H-imidazo[4,5-b]pyridin-3-yl)pyrrolidin-1-yl)methyl)-1H-imidazole-5-carboxylic acid A mixture of Example 80 (190 mg) and concentrated hydrochloric acid (1 mL) was stirred at 110° C. under microwave irradiation for 1 hour. To the reaction mixture was added an aqueous solution of sodium hydroxide (5 mol/L) under ice-cooling until a precipitate was formed. The precipitate was collected by filtration. The obtained solid was purified by ODS column chromatography (eluent: water/acetonitrile=98/2-30/70) to give the title compound (25 mg).

Example 82

(S)-2-((3-(1-(4'-Hydroxy-[1,1'-biphenyl]-4-yl)-2-oxo-1,2-dihydro-3H-imidazo[4,5-b]pyridin-3-yl)pyrrolidin-1-yl)methyl)-1-methyl-1H-imidazole-5-carboxylic acid A mixture of Example K-6 (150 mg) and concentrated hydrochloric acid (2 mL) was stirred at 110° C. under microwave irradiation for 1 hour. The reaction mixture was neutralized by the addition of an aqueous solution of sodium hydroxide (5 mol/L). The mixture was diluted with DMSO, and then purified by ODS column chromatography (eluent: water/acetonitrile=98/2-30/70) to give the title compound (83 mg).

Example 83

(S)-2-((3-(1-(4'-Carboxy-[1,1'-biphenyl]-4-yl)-2-oxo-1,2-dihydro-3H-imidazo[4,5-b]pyridin-3-yl)pyrrolidin-1-yl)methyl)-1-methyl-1H-imidazole-5-carboxylic acid A mixture of Example K-8 (199 mg) and concentrated hydrochloric acid (1 mL) was stirred at 110° C. under microwave irradiation for 1 hour. The reaction mixture was neutralized by the addition of an aqueous solution of sodium hydroxide (5 mol/L). The mixture was diluted with DMSO, and then purified by ODS column chromatography (eluent: water/acetonitrile=98/2-30/70) to give the title compound (101 mg).

Example 84

(S)-2-((3-(1-(4'-Carboxy-2-hydroxy-[1,1'-biphenyl]-4-yl)-2-oxo-1,2-dihydro-3H-imidazo[4,5-b]pyridin-3-yl)pyrrolidin-1-yl)methyl)-1-methyl-1H-imidazole-5-carboxylic acid A mixture of Example K-10 (178 mg) and concentrated hydrochloric acid (1 mL) was stirred at 110° C. under microwave irradiation for 1 hour. The reaction mixture was neutralized with an aqueous solution of sodium hydroxide (5 mol/L), and then purified by ODS column chromatography (eluent: water/acetonitrile=98/2-30/70). A part of the obtained product (16 mg, out of 107 mg) was further purified by ODS column chromatography (eluent: water with 0.1% formic acid/acetonitrile=98/2-30/70) to give the title compound (8 mg).

Example 85

(S)-2-((3-(1-(6-(4-Carboxyphenyl)pyridin-3-yl)-2-oxo-1,2-dihydro-3H-imidazo[4,5-b]pyridin-3-yl)pyrrolidin-1-yl)methyl)-1-methyl-1H-imidazole-5-carboxylic acid A mixture of Example K-12 (195 mg) and concentrated hydrochloric acid (1 mL) was stirred at 110° C. under microwave irradiation for 1 hour. The reaction mixture was neutralized by the addition of an aqueous solution of sodium hydroxide (5 mol/L). The mixture was diluted with DMSO. The insoluble material was removed through Celite. The filtrate was purified by ODS column chromatography (eluent: water/acetonitrile=98/2-30/70) to give the title compound (60 mg).

Example 86

(S)-2-((3-(1-([1,1'-Biphenyl]-4-yl)-2-oxo-1,2-dihydro-3H-imidazo[4,5-b]pyridin-3-yl)pyrrolidin-1-yl)methyl)-1-methyl-1H-imidazole-5-carboxylic acid A mixture of Example K-14 (58 mg) and concentrated hydrochloric acid (1 mL) was stirred at 110° C. under microwave irradiation for 1 hour. The reaction mixture was neutralized by the addition of an aqueous solution of sodium hydroxide (5 mol/L), and then concentrated under reduced pressure. To the residue was added DMSO. The insoluble material was removed through Celite. The filtrate was purified by ODS column chromatography (eluent: water/acetonitrile=90/10-30/70) to give the title compound (2.2 mg).

Example 87

(S)-1-Methyl-2-((3-(2-oxo-1-phenyl-1,2-dihydro-3H-imidazo[4,5-b]pyridin-3-yl)pyrrolidin-1-yl)methyl)-1H-imidazole-5-carboxylic acid A mixture of Example K-16 (75 mg) and concentrated hydrochloric acid (1 mL) was stirred at 110° C. under microwave irradiation for 1 hour. The reaction mixture was neutralized by the addition of an aqueous solution of sodium hydroxide (5 mol/L). The mixture was diluted with DMSO, and then purified by ODS column chromatography (eluent: water/acetonitrile=98/2-30/70) to give the title compound (48 mg).

Example 88

(R)-2-((3-(1-(6-(4-Carboxyphenyl)pyridin-3-yl)-2-oxo-1,2-dihydro-3H-imidazo[4,5-b]pyridin-3-yl)pyrrolidin-1-yl)methyl)-1-methyl-1H-imidazole-5-carboxylic acid A mixture of Example K-18 (207 mg) and concentrated hydrochloric acid (1 mL) was stirred at 110° C. under microwave irradiation for 1 hour. The reaction mixture was neutralized by the addition of an aqueous solution of sodium hydroxide (5 mol/L). The precipitate was collected by filtration, and the obtained solid was dried to give the title compound (40 mg).

Example 89

(S)-1-(4'-Hydroxy-[1,1'-biphenyl]-4-yl)-3-(1-((3-methylpyridin-2-yl)methyl)pyrrolidin-3-yl)-1,3-dihydro-2H-imidazo[4,5-b]pyridin-2-one To a mixture of Reference Example F-21 (35 mg), 3-methyl-2-pyridine carboxyaldehyde (18 mg) and dichloromethane (1 mL) was added NaBH(OAc)$_3$ (94 mg). The reaction mixture was stirred at room temperature for 30 minutes. To the reaction mixture was added methanol (1 mL), and the mixture was stirred for 30 minutes. The reaction mixture was concentrated under reduced pressure. The residue was purified by column chromatography on amino-silica gel (eluent: n-hexane/ethyl acetate/methanol=80/20/0-0/100/0-0/90/10) to give the title compound (32 mg).

Example 90

(S)-3-(1-((3-Methylpyridin-2-yl)methyl)pyrrolidin-3-yl)-1-(4-(pyridin-4-yl)phenyl)-1,3-dihydro-2H-imidazo[4,5-b]pyridin-2-one The title compound was prepared in a similar manner to that described in Example 89 using Reference Example F-22 instead of Reference Example F-21.

Example 91

(S)-4'-(3-(1-((3-Methylpyridin-2-yl)methyl)pyrrolidin-3-yl)-2-oxo-2,3-dihydro-1H-imidazo[4,5-b]pyridin-1-yl)-[1,1'-biphenyl]-4-carboxylic acid To a mixture of Example G-48 (72 mg), methanol (1 mL) and THF (1 mL) was added an aqueous solution of sodium hydroxide (5 mol/L, 2 mL). The reaction mixture was stirred at room temperature for 4 hours. To the reaction mixture was added hydrochloric acid (2 mol/L, 5 mL), and the mixture was stirred under ice-cooling for 30 minutes. The precipitate was collected by filtration, and the obtained solid was dried to give the title compound (37 mg).

The following tables show chemical structure, physical property and PHD2 inhibitory activity (see, Test Example 1) of Examples.

TABLE 2

| Ex. No. | Structure | Physical data | IC$_{50}$ (μM) |
|---|---|---|---|
| 1 | 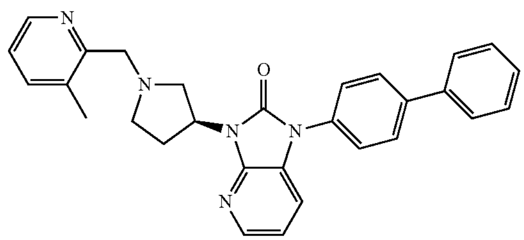 [SMILES: Cc1cccnc1CN1CC[C@H](n2c(=O)n(-c3ccc(-c4ccccc4)cc3)c3cccnc32)C1] | $^1$H-NMR (CDCl3) δ ppm: 2.30-2.48 (4H, m), 2.50-2.60 (1H, m), 3.10-3.13 (3H, m), 3.17-3.25 (1H, m), 3.83-3.99 (2H, m), 5.25-5.38 (1H, m), 6.99 (1H, dd, J = 5.2, 7.8 Hz), 7.09 (1H, dd, J = 4.8, 7.6 Hz), 7.33 (1H, dd, J = 1.4, 7.8 Hz), 7.38-7.54 (4H, m), 7.56-7.66 (4H, m), 7.71-7.78 (2H, m), 8.10 (1H, dd, J = 1.4, 5.2 Hz), 8.37-8.42 (1H, m) | 8.43 |
| 2 | 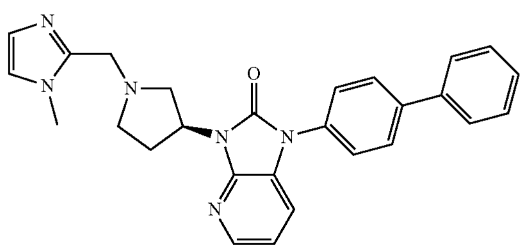 [SMILES: Cn1ccnc1CN1CC[C@H](n2c(=O)n(-c3ccc(-c4ccccc4)cc3)c3cccnc32)C1] | $^1$H-NMR (CDCl3) δ ppm: 2.25-2.41 (1H, m), 2.52-2.64 (1H, m), 2.89-3.12 (4H, m), 3.76 (3H, s), 3.80-3.90 (2H, m), 5.21-5.33 (1H, m), 6.84 (1H, d, J = 1.2 Hz), 6.91 (1H, d, J = 1.2 Hz), 7.00 (1H, dd, J = 5.2, 7.8 Hz), 7.33 (1H, dd, J = 1.4, 7.8 Hz), 7.36-7.52 (3H, m), 7.55-7.65 (4H, m), 7.72-7.77 (2H, m), 8.09 (1H, dd, J = 1.4, 5.2 Hz) | 0.79 |
| 3 | 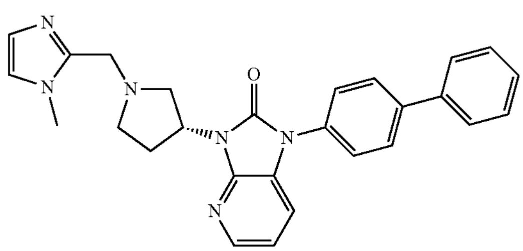 [SMILES: Cn1ccnc1CN1CC[C@@H](n2c(=O)n(-c3ccc(-c4ccccc4)cc3)c3cccnc32)C1] | $^1$H-NMR (CDCl3) δ ppm: 2.23-2.40 (1H, m), 2.53-2.64 (1H, m), 2.89-3.09 (4H, m), 3.76 (3H, s), 3.81-3.89 (2H, m), 5.23-5.32 (1H, m), 6.84 (1H, d, J = 1.2 Hz), 6.91 (1H, d, J = 1.2 Hz), 7.00 (1H, dd, J = 5.2, 7.8 Hz), 7.33 (1H, dd, J = 1.4, 7.8 Hz), 7.38-7.52 (3H, m), 7.56-7.64 (4H, m), 7.71-7.76 (2H, m), 8.09 (1H, dd, J = 1.4, 5.2 Hz) | 3.90 |
| 4 | 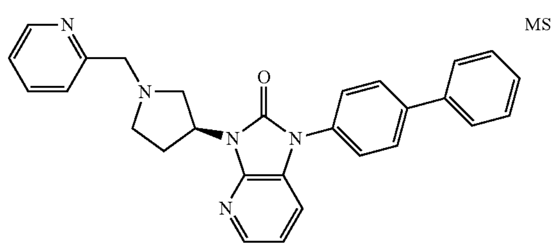 | MS (ESI_APCI, m/z): 448 (M + H)$^+$ | 3.45 |
| 5 | 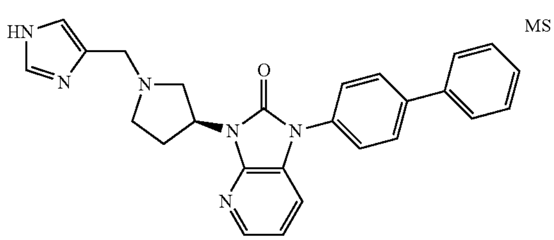 | MS (ESI_APCI, m/z): 437 (M + H)$^+$ | 2.98 |

TABLE 2-continued

| Ex. No. | Structure | Physical data | IC$_{50}$ (μM) |
|---|---|---|---|
| 6 | 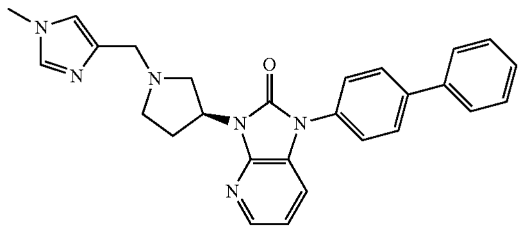 [SMILES: Cn1cnc(CN2CC[C@H](n3c(=O)n(-c4ccc(-c5ccccc5)cc4)c4cccnc43)C2)c1] | MS (ESI_APCI, m/z): 451 (M + H)$^+$ | *34% |
| 7 | 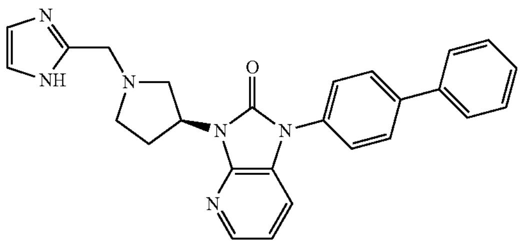 [SMILES: O=c1n(-c2ccc(-c3ccccc3)cc2)c2cccnc2n1[C@H]1CCN(Cc2ncc[nH]2)C1] | MS (ESI_APCI, m/z): 437 (M + H)$^+$ | 15.64 |

TABLE 3

| Ex. No. | Structure | Physical data | IC$_{50}$ (μM) |
|---|---|---|---|
| 8 | 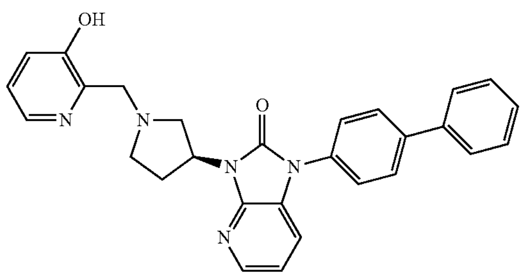 [SMILES: O=c1n(-c2ccc(-c3ccccc3)cc2)c2cccnc2n1[C@H]1CCN(Cc2ncccc2O)C1] | $^1$H-NMR (DMSO) δ ppm: 2.25-2.36 (1H, m), 2.42-2.55 (1H, m), 2.72-2.80 (1H, m), 2.99-3.10 (2H, m), 3.15-3.22 (1H, m), 3.86-4.10 (2H, m), 5.15-5.26 (1H, m), 7.09-7.18 (3H, m), 7.38-7.55 (4H, m), 7.65-7.70 (2H, m), 7.73-7.77 (2H, m), 7.84-7.90 (2H, m), 7.95 (1H, dd, J = 1.8, 4.3 Hz), 8.10 (1H, dd, J = 1.4, 5.2 Hz) | *29% |
| 9 | 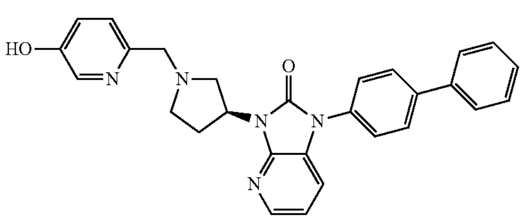 [SMILES: O=c1n(-c2ccc(-c3ccccc3)cc2)c2cccnc2n1[C@H]1CCN(Cc2ccc(O)cn2)C1] | $^1$H-NMR (DMSO-d6) δ ppm: 2.14-2.27 (1H, m), 2.39-2.53 (1H, m), 2.80-3.05 (4H, m), 3.69 (2H, s), 5.04-5.15 (1H, m), 7.07-7.16 (2H, m), 7.25-7.32 (1H, m), 7.38-7.55 (4H, m), 7.64-7.69 (2H, m), 7.71-7.78 (2H, m), 7.83-7.89 (2H, m), 8.01-8.04 (1H, m), 8.10 (1H, dd, J = 1.4, 5.2 Hz), 9.77 (1H, brs) | 8.03 |
| 10 | 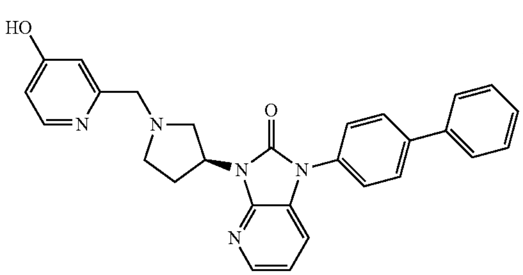 [SMILES: O=c1n(-c2ccc(-c3ccccc3)cc2)c2cccnc2n1[C@H]1CCN(Cc2cc(O)ccn2)C1] | $^1$H-NMR (DMSO-d6) δ ppm: 2.20-2.31 (1H, m), 2.43-2.54 (1H, m), 2.83-3.09 (4H, m), 3.51-3.70 (2H, m), 5.08-5.23 (1H, m), 5.90-6.14 (2H, m), 7.12 (1H, dd, J = 5.2, 7.8 Hz), 7.38-7.59 (5H, m), 7.64-7.70 (2H, m), 7.72-7.78 (2H, m), 7.84-7.90 (2H, m), 8.11 (1H, dd, J = 1.4, 5.2 Hz), 11.23 (1H, brs) | 5.49 |

TABLE 3-continued

| Ex. No. | Structure | Physical data | IC$_{50}$ (μM) |
|---|---|---|---|
| 11 | 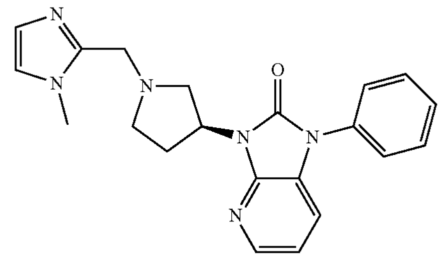 [SMILES: Cn1ccnc1CN1CC[C@H](n2c(=O)n(-c3ccccc3)c3cccnc32)C1] | MS (ESI_APCI, m/z): 375 (M + H)$^+$ | 85.38 |
| 12 | 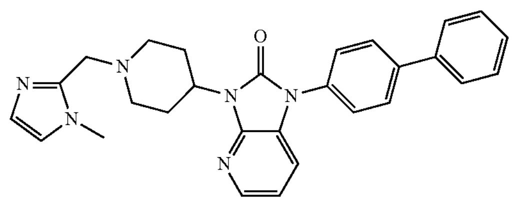 [SMILES: Cn1ccnc1CN1CCC(n2c(=O)n(-c3ccc(-c4ccccc4)cc3)c3cccnc32)CC1] | 1H-NMR (CDCl3) δ ppm: 1.80-1.88 (2H, m), 2.24-2.33 (2H, m), 2.74-2.87 (2H, m), 2.93-3.02 (2H, m), 3.67 (2H, s), 3.79 (3H, s), 4.50-4.61 (1H, m), 6.87 (1H, d, J = 1.2 Hz), 6.93 (1H, d, J = 1.2 Hz), 6.99 (1H, dd, J = 5.2, 7.8 Hz), 7.31-7.42 (2H, m), 7.45-7.51 (2H, m), 7.57-7.65 (4H, m), 7.71-7.77 (2H, m), 8.09 (1H, dd, J = 1.4, 5.2 Hz) | 4.95 |
| 13 | 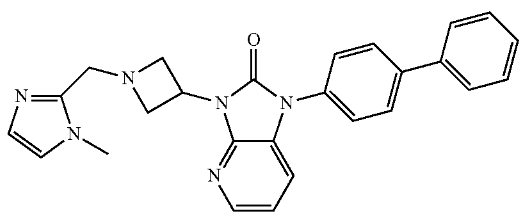 [SMILES: Cn1ccnc1CN1CC(n2c(=O)n(-c3ccc(-c4ccccc4)cc3)c3cccnc32)C1] | $^1$H-NMR (CDCl3) δ ppm: 3.98 (3H, s), 4.46-4.56 (2H, m), 4.61-4.70 (2H, m), 4.98-5.07 (2H, m), 5.57-5.70 (1H, m), 6.98 (1H, d, J = 1.2 Hz), 7.07-7.12 (2H, m), 7.38-7.43 (2H, m), 7.46-7.53 (2H, m), 7.56-7.65 (4H, m), 7.74-7.79 (2H, m), 8.19 (1H, dd, J = 1.4, 5.2 Hz) | 0.12 |
| 14 | 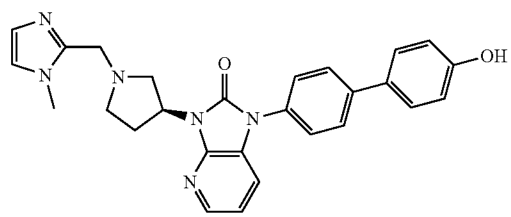 [SMILES: Cn1ccnc1CN1CC[C@H](n2c(=O)n(-c3ccc(-c4ccc(O)cc4)cc3)c3cccnc32)C1] | $^1$H-NMR (CDCl3) δ ppm: 2.24-2.39 (1H, m), 2.47-2.61 (1H, m), 2.93-3.11 (4H, m), 3.78 (3H, s), 3.80-3.97 (2H, m), 5.14-5.26 (1H, m), 6.81-6.89 (3H, m), 6.92-7.00 (2H, m), 7.19-7.24 (1H, m), 7.29-7.42 (4H, m), 7.54-7.59 (2H, m), 8.05 (1H, dd, J = 1.4, 5.2 Hz) | 0.36 |

TABLE 4

| Ex. No. | Structure | Physical data | IC$_{50}$ (μM) |
|---|---|---|---|
| 15 | 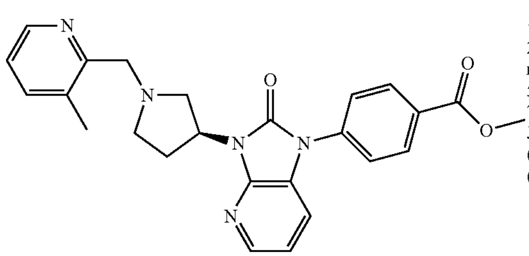 [SMILES: COC(=O)c1ccc(-n2c(=O)n([C@H]3CCN(Cc4ncccc4C)C3)c3ncccc32)cc1] | $^1$H-NMR (CDCl3) δ ppm: 2.28-2.40 (1H, m), 2.43 (3H, s), 2.47-2.57 (1H, m), 2.98-3.10 (3H, m), 3.15-3.23 (1H, m), 3.82-3.98 (5H, m), 5.24-5.35 (1H, m), 7.00 (1H, dd, J = 5.2, 7.8 Hz), 7.06-7.11 (1H, m, J = 4.8, 7.6 Hz), 7.34 (1H, dd, J = 1.4, 7.8 Hz), 7.41-7.46 (1H, m), 7.62-7.67 (2H, m), 8.11 (1H, dd, J = 1.4, 5.2 Hz), 8.17-8.23 (2H, m), 8.37-8.40 (1H, m) | 64.50 |

TABLE 4-continued

| Ex. No. | Structure | Physical data | IC$_{50}$ (μM) |
|---|---|---|---|
| 16 | 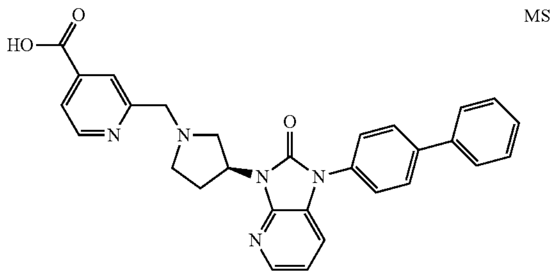 | MS (ESI_APCI, m/z): 492 (M + H)$^+$ | 0.14 |
| 17 | 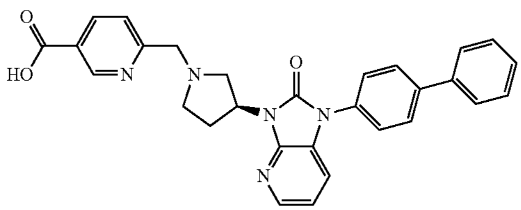 [SMILES: O=C(O)c1ccc(CN2CC[C@H](n3c(=O)n(-c4ccc(-c5ccccc5)cc4)c4cccnc43)C2)nc1] | MS (ESI_APCI, m/z): 492 (M + H)$^+$ | 0.52 |
| 18 | 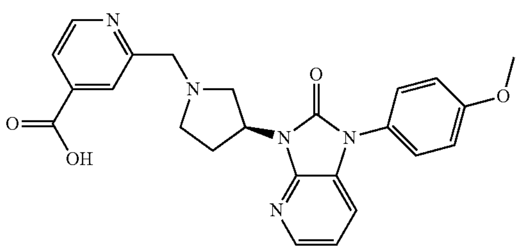 [SMILES: COc1ccc(-n2c(=O)n([C@H]3CCN(Cc4cc(C(=O)O)ccn4)C3)c3ncccc32)cc1] | MS (ESI_APCI, m/z): 446 (M + H)$^+$ | 1.95 |
| 19 | 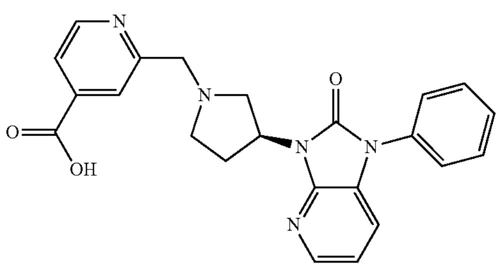 [SMILES: O=C(O)c1ccnc(CN2CC[C@H](n3c(=O)n(-c4ccccc4)c4cccnc43)C2)c1] | MS (ESI_APCI, m/z): 416 (M + H)$^+$ | 6.34 |
| 20 | 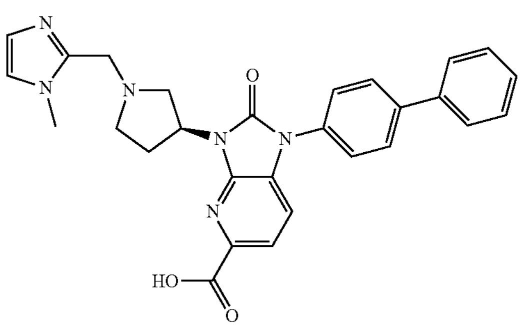 [SMILES: Cn1ccnc1CN1CC[C@H](n2c(=O)n(-c3ccc(-c4ccccc4)cc3)c3ccc(C(=O)O)nc32)C1] | MS (ESI_APCI, m/z): 495 (M + H)$^+$ | 6.71 |

TABLE 4-continued

| Ex. No. | Structure | Physical data | IC$_{50}$ (μM) |
|---|---|---|---|
| 21 | 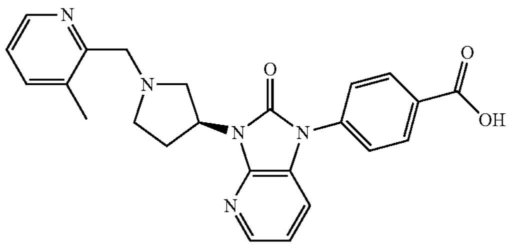 [SMILES: Cc1cccnc1CN1CC[C@H](n2c(=O)n(-c3ccc(C(=O)O)cc3)c3cccnc32)C1] | MS (ESI_APCI, m/z): 430 (M + H)$^+$ | *39% |

TABLE 5

| Ex. No. | Structure | Physical data | IC$_{50}$ (μM) |
|---|---|---|---|
| 22 | 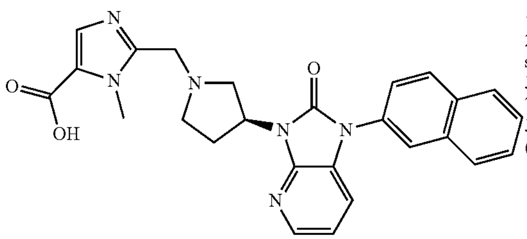 | $^1$H-NMR (DMSO-d6) δ ppm: 2.16-2.29 (1H, m), 2.41-2.54 (1H, m), 2.85-3.05 (4H, m), 3.83 (2H, s), 3.91 (3H, s), 5.06-5.19 (1H, m), 7.11 (1H, dd, J = 5.2, 7.8 Hz), 7.46 (1H, dd, J = 1.4, 7.8 Hz), 7.50 (1H, s), 7.58-7.64 (2H, m), 7.70 (1H, dd, J = 2.0, 8.8 Hz), 7.99-8.06 (2H, m), 8.08-8.16 (3H, m), 12.79 (1H, brs) | 0.30 |
| 23 | 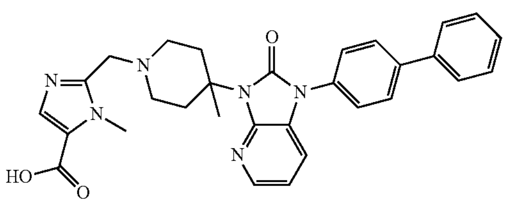 [SMILES: Cn1c(C(=O)O)cnc1CN1CCC(C)(n2c(=O)n(-c3ccc(-c4ccccc4)cc3)c3cccnc32)CC1] | $^1$H-NMR (DMSO-d6) δ ppm: 1.56 (3H, s), 1.79-1.92 (2H, m), 2.22-2.34 (2H, m), 2.57-2.65 (2H, m), 3.39-3.50 (2H, m), 3.55 (2H, s), 3.88 (3H, s), 7.09 (1H, dd, J = 5.2, 7.8 Hz), 7.37-7.55 (5H, m), 7.63-7.68 (2H, m), 7.72-7.78 (2H, m), 7.83-7.89 (2H, m), 8.05 (1H, dd, J = 1.4, 5.2 Hz), 12.72 (1H, brs) | 5.50 |
| 24 | 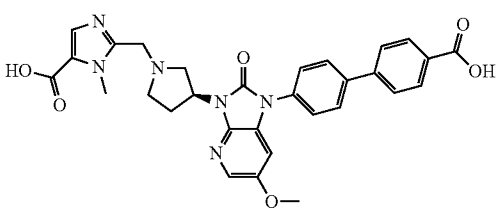 [SMILES: COc1cnc2c(c1)n(-c1ccc(-c3ccc(C(=O)O)cc3)cc1)c(=O)n2[C@H]1CCN(Cc2ncc(C(=O)O)n2C)C1] | $^1$H-NMR (DMSO-d6) δ ppm: 2.16-2.27 (1H, m), 2.37-2.48 (1H, m), 2.82-3.01 (4H, m), 3.77-3.83 (5H, m), 3.90 (3H, s), 4.99-5.09 (1H, m), 7.12 (1H, d, J = 2.5 Hz), 7.48 (1H, s), 7.69-7.74 (2H, m), 7.83 (1H, d, J = 2.5 Hz), 7.86-7.96 (4H, m), 8.03-8.08 (2H, m), 12.34-13.27 (2H, m) | 0.11 |
| 25 | 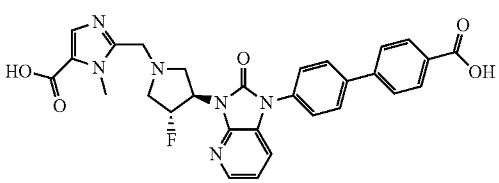 [SMILES: Cn1c(C(=O)O)cnc1CN1C[C@@H](F)[C@H](n2c(=O)n(-c3ccc(-c4ccc(C(=O)O)cc4)cc3)c3cccnc32)C1] | $^1$H-NMR (DMSO-d6) δ ppm: 2.82-2.90 (1H, m), 2.94-3.26 (3H, m), 3.85 (2H, s), 3.91 (3H, s), 4.99-5.15 (1H, m), 5.67-5.86 (1H, m), 7.14 (1H, dd, J = 5.2, 7.8 Hz), 7.47-7.53 (2H, m), 7.70-7.75 (2H, m), 7.86-7.91 (2H, m), 7.92-7.97 (2H, m), 8.04-8.11 (3H, m), 12.50-13.28 (2H, m) | 0.11 |
| 26 | 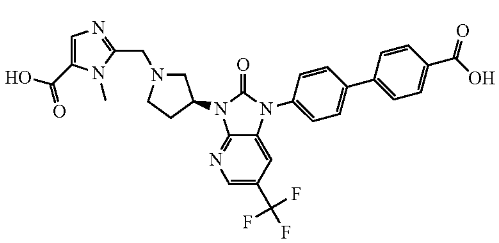 [SMILES: Cn1c(C(=O)O)cnc1CN1CC[C@H](n2c(=O)n(-c3ccc(-c4ccc(C(=O)O)cc4)cc3)c3cc(C(F)(F)F)cnc32)C1] | $^1$H-NMR (DMSO-d6) δ ppm: 2.14-2.32 (1H, m), 2.40-2.56 (1H, m), 2.81-3.04 (4H, m), 3.82 (2H, s), 3.91 (3H, s), 5.06-5.18 (1H, m), 7.42-7.49 (1H, m), 7.63 (1H, d, J = 1.8 Hz), 7.70-7.77 (2H, m), 7.86-7.91 (2H, m), 7.93-7.99 (2H, m), 8.04-8.09 (2H, m), 8.48-8.52 (1H, m), 12.41-13.27 (2H, m) | 0.13 |

TABLE 5-continued

| Ex. No. | Structure | Physical data | IC$_{50}$ (μM) |
|---|---|---|---|
| 27 | 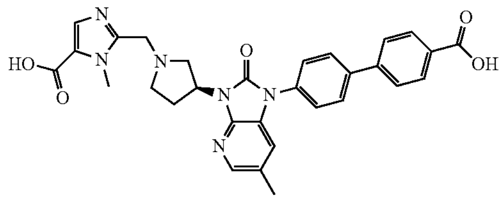 [SMILES: Cc1cnc2c(c1)n(-c1ccc(-c3ccc(C(=O)O)cc3)cc1)c(=O)n2[C@H]1CCN(Cc2ncc(C(=O)O)n2C)C1] | $^1$H-NMR (DMSO-d6) δ ppm: 2.13-2.27 (1H, m), 2.30 (3H, s), 2.38-2.50 (1H, m), 2.82-3.02 (4H, m), 3.81 (2H, s), 3.91 (3H, s), 5.01-5.11 (1H, m), 7.31-7.35 (1H, m), 7.48 (1H, s), 7.67-7.73 (2H, m), 7.85-7.97 (5H, m), 8.03-8.09 (2H, m), 12.91 (2H, brs) | 0.11 |
| 28 | 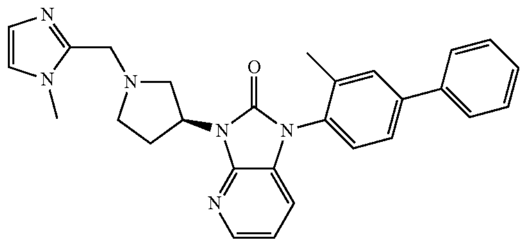 [SMILES: Cc1cc(-c2ccccc2)ccc1-n1c(=O)n([C@H]2CCN(Cc3nccn3C)C2)c2ncccc21] | $^1$H-NMR (CDCl3) δ ppm: 2.22 (3H, d, J = 5.3 Hz), 2.29-2.41 (1H, m), 2.52-2.67 (1H, m), 2.90-3.11 (4H, m), 3.76 (3H, s), 3.79-3.90 (2H, m), 5.20-5.34 (1H, m), 6.84 (1H, d, J = 1.2 Hz), 6.91 (1H, d, J = 1.2 Hz), 6.95-6.97 (2H, m), 7.31-7.42 (2H, m), 7.44-7.50 (2H, m), 7.51-7.56 (1H, m), 7.58-7.64 (3H, m), 8.06-8.09 (1H, m) | 28.2 |

TABLE 6

| Ex. No. | Structure | Physical data | IC$_{50}$ (μM) |
|---|---|---|---|
| 29 | 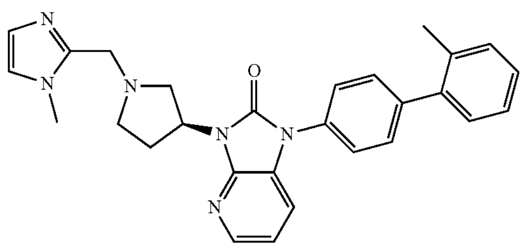 [SMILES: Cc1ccccc1-c1ccc(-n2c(=O)n([C@H]3CCN(Cc4nccn4C)C3)c3ncccc32)cc1] | $^1$H-NMR (CDCl3) δ ppm: 2.26-2.39 (4H, m), 2.53-2.64 (1H, m), 2.91-3.12 (4H, m), 3.76 (3H, s), 3.80-3.89 (2H, m), 5.21-5.34 (1H, m), 6.84 (1H, d, J = 1.2 Hz), 6.91 (1H, d, J = 1.2 Hz), 7.00 (1H, dd, J = 5.2, 7.8 Hz), 7.24-7.32 (4H, m), 7.35 (1H, dd, J = 1.4, 7.8 Hz), 7.46-7.58 (4H, m), 8.09 (1H, dd, J = 1.4, 5.2 Hz) | 2.09 |
| 30 | 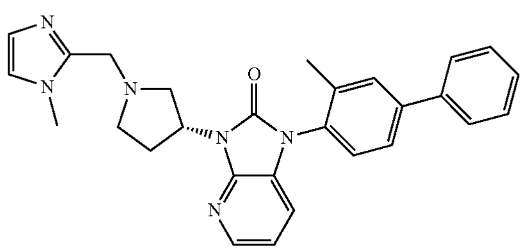 [SMILES: Cc1cc(-c2ccccc2)ccc1-n1c(=O)n([C@@H]2CCN(Cc3nccn3C)C2)c2ncccc21] | $^1$H-NMR (CDCl3) δ ppm: 2.21 (3H, d, J = 5.3 Hz), 2.27-2.40 (1H, m), 2.51-2.65 (1H, m), 2.89-2.99 (1H, m), 3.01-3.12 (3H, m), 3.76 (3H, s), 3.80-3.90 (2H, m), 5.18-5.33 (1H, m), 6.84 (1H, d, J = 1.2 Hz), 6.91 (1H, d, J = 1.2 Hz), 6.94-6.97 (2H, m), 7.29-7.64 (8H, m), 8.07-8.09 (1H, m) | 3.48 |
| 31 | 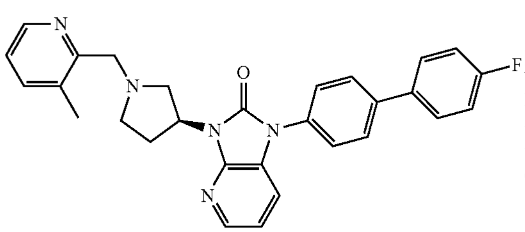 [SMILES: Cc1cccnc1CN1CC[C@H](n2c(=O)n(-c3ccc(-c4ccc(F)cc4)cc3)c3cccnc32)C1] | $^1$H-NMR (CDCl3) δ ppm: 2.28-2.41 (1H, m), 2.43 (3H, s), 2.48-2.60 (1H, m), 2.99-3.10 (3H, m), 3.16-3.24 (1H, m), 3.82-3.99 (2H, m), 5.25-5.37 (1H, m), 6.99 (1H, dd, J = 5.2, 7.8 Hz), 7.09 (1H, dd, J = 4.8, 7.6 Hz), 7.12-7.20 (2H, m), 7.32 (1H, dd, J = 1.4, 7.8 Hz), 7.41-7.46 (1H, m), 7.49-7.61 (4H, m), 7.65-7.71 (2H, m), 8.09 (1H, dd, J = 1.4, 5.2 Hz), 8.37-8.41 (1H, m) | 12.45 |
| 32 | 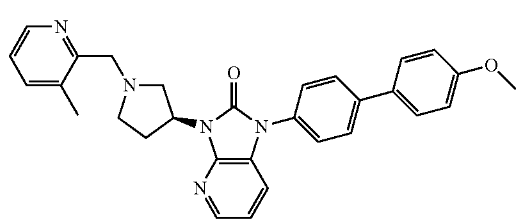 [SMILES: COc1ccc(-c2ccc(-n3c(=O)n([C@H]4CCN(Cc5ncccc5C)C4)c4ncccc43)cc2)cc1] | $^1$H-NMR (CDCl3) δ ppm: 2.28-2.41 (1H, m), 2.43 (3H, s), 2.47-2.60 (1H, m), 2.99-3.10 (3H, m), 3.16-3.24 (1H, m), 3.83-3.98 (2H, m), 5.23-5.37 (1H, m), 6.95-7.03 (3H, m), 7.09 (1H, dd, J = 4.8, 7.6 Hz), 7.29-7.33 (1H, m), 7.41-7.46 (1H, m), 7.50-7.58 (4H, m), 7.66-7.71 (2H, m), 8.09 (1H, dd, J = 1.4, 5.2 Hz), 8.37-8.41 (1H, m) | 42.10 |

TABLE 6-continued

| Ex. No. | Structure | Physical data | IC$_{50}$ (μM) |
|---|---|---|---|
| 33 | 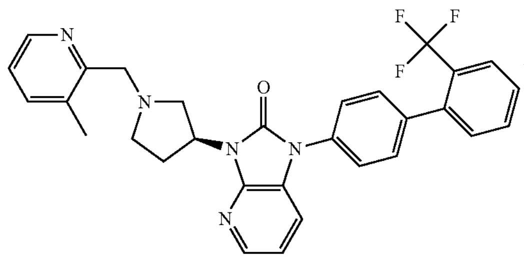 [SMILES: Cc1cccnc1CN1CC[C@H](n2c(=O)n(-c3ccc(-c4ccccc4C(F)(F)F)cc3)c3cccnc32)C1] | $^1$H-NMR (CDCl3) δ ppm: 2.28-2.41 (1H, m), 2.43 (3H, s), 2.48-2.60 (1H, m), 2.98-3.12 (3H, m), 3.14-3.25 (1H, m), 3.82-4.00 (2H, m), 5.24-5.40 (1H, m), 6.95-7.03 (1H, m), 7.05-7.13 (1H, m), 7.28-7.63 (9H, m), 7.75-7.80 (1H, m), 8.10 (1H, dd, J = 1.4, 5.2 Hz), 8.36-8.42 (1H, m) | *41% |
| 34 | 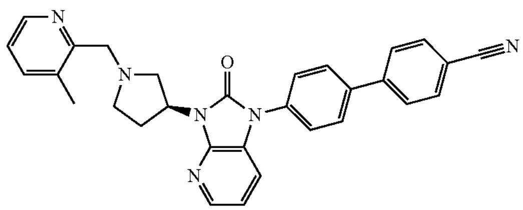 [SMILES: Cc1cccnc1CN1CC[C@H](n2c(=O)n(-c3ccc(-c4ccc(C#N)cc4)cc3)c3cccnc32)C1] | $^1$H-NMR (CDCl3) δ ppm: 2.27-2.60 (5H, m), 2.99-3.11 (3H, m), 3.17-3.23 (1H, m), 3.82-3.99 (2H, m), 5.25-5.39 (1H, m), 7.00 (1H, d, J = 5.2, 7.8 Hz), 7.09 (1H, dd, J = 4.8, 7.6 Hz), 7.34 (1H, dd, J = 1.4, 7.8 Hz), 7.41-7.47 (1H, m), 7.62-7.80 (8H, m), 8.11 (1H, dd, J = 1.4, 5.2 Hz), 8.36-8.42 (1H, m) | 5.70 |
| 35 | 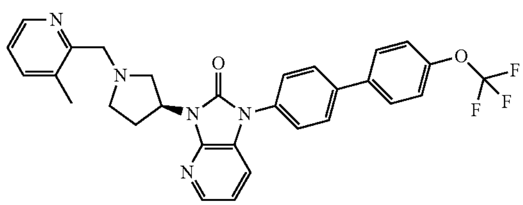 [SMILES: Cc1cccnc1CN1CC[C@H](n2c(=O)n(-c3ccc(-c4ccc(OC(F)(F)F)cc4)cc3)c3cccnc32)C1] | $^1$H-NMR (CDCl3) δ ppm: 2.28-2.40 (1H, m), 2.43 (3H, s), 2.47-2.60 (1H, m), 2.99-3.10 (3H, m), 3.16-3.24 (1H, m), 3.82-3.99 (2H, m), 5.23-5.36 (1H, m), 7.00 (1H, d, J = 5.2, 7.8 Hz), 7.06-7.11 (1H, m), 7.28-7.35 (3H, m), 7.40-7.54 (2H, m), 7.57-7.73 (5H, m), 8.10 (1H, dd, J = 1.4, 5.2 Hz), 8.36-8.42 (1H, m) | 80.5 |

TABLE 7

| Ex. No. | Structure | Physical data | IC$_{50}$ (μM) |
|---|---|---|---|
| 36 | 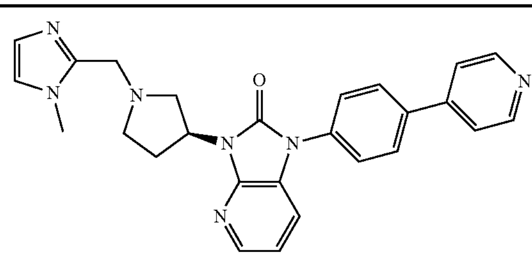 | MS (ESI_APCI, m/z): 452 (M + H)$^+$ | 1.51 |
| 37 | 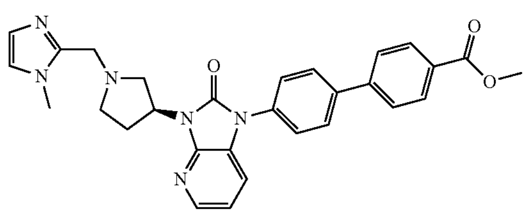 [SMILES: COC(=O)c1ccc(-c2ccc(-n3c(=O)n([C@H]4CCN(Cc5nccn5C)C4)c4ncccc43)cc2)cc1] | $^1$H-NMR (CDCl3) δ ppm: 2.26-2.39 (1H, m), 2.52-2.64 (1H, m), 2.90-2.98 (1H, m), 3.00-3.10 (3H, m), 3.76 (3H, s), 3.80-3.89 (2H, m), 3.96 (3H, s), 5.22-5.33 (1H, m), 6.83 (1H, d, J = 1.2 Hz), 6.91 (1H, d, J = 1.2 Hz), 7.01 (1H, dd, J = 5.2, 7.8 Hz), 7.33 (1H, dd, J = 1.4, 7.8 Hz), 7.60-7.65 (2H, m), 7.67-7.72 (2H, m), 7.75-7.81 (2H, m), 8.09 (1H, dd, J = 1.4, 5.2 Hz), 8.12-8.17 (2H, m) | 6.28 |
| 38 | 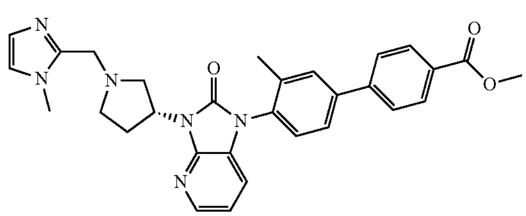 [SMILES: COC(=O)c1ccc(-c2ccc(-n3c(=O)n([C@@H]4CCN(Cc5nccn5C)C4)c4ncccc43)c(C)c2)cc1] | $^1$H-NMR (CDCl3) δ ppm: 2.23 (3H, d, J = 5.3 Hz), 2.28-2.40 (1H, m), 2.54-2.64 (1H, m), 2.90-2.99 (1H, m), 3.00-3.11 (3H, m), 3.76 (3H, s), 3.79-3.90 (2H, m), 3.96 (3H, s), 5.20-5.34 (1H, m), 6.84 (1H, d, J = 1.2 Hz), 6.91 (1H, d, J = 1.2 Hz), 6.94-6.97 (2H, m), 7.35-7.40 (1H, m), 7.55-7.60 (1H, m), 7.62-7.65 (1H, m), 7.66-7.71 (2H, m), 8.07-8.10 (1H, m), 8.11-8.17 (2H, m) | 4.63 |

TABLE 7-continued

| Ex. No. | Structure | Physical data | IC$_{50}$ (μM) |
|---|---|---|---|
| 39 | 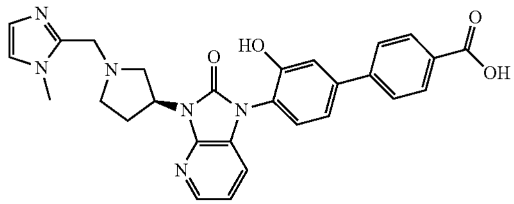 [SMILES: Cn1ccnc1CN1CC[C@H](n2c(=O)n(-c3ccc(-c4ccc(C(=O)O)cc4)cc3O)c3cccnc32)C1] | MS (ESI_APCI, m/z): 511 (M + H)$^+$ | 0.34 |
| 40 | 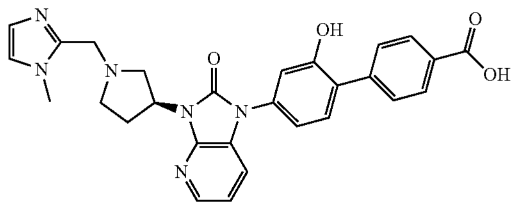 [SMILES: Cn1ccnc1CN1CC[C@H](n2c(=O)n(-c3ccc(-c4ccc(C(=O)O)cc4)c(O)c3)c3cccnc32)C1] | MS (ESI_APCI, m/z): 511 (M + H)$^+$ | 0.76 |
| 41 | 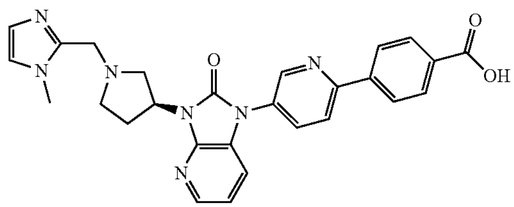 [SMILES: Cn1ccnc1CN1CC[C@H](n2c(=O)n(-c3ccc(-c4ccc(C(=O)O)cc4)nc3)c3cccnc32)C1] | $^1$H-NMR (DMSO-d6) δ ppm: 2.15-2.27 (1H, m), 2.41-2.49 (1H, m), 2.82-3.00 (4H, m), 3.69 (3H, s), 3.74 (2H, s), 5.03-5.16 (1H, m), 6.74 (1H, d, J = 1.2 Hz), 7.07 (1H, d, J = 1.2 Hz), 7.13 (1H, dd, J = 5.2, 7.8 Hz), 7.54 (1H, dd, J = 1.4, 7.8 Hz), 8.06-8.14 (3H, m), 8.17 (1H, dd, J = 2.6, 8.5 Hz), 8.25-8.30 (3H, m), 8.93-8.96 (1H, m), 13.11 (1H, brs) | 1.46 |

TABLE 8

| Ex. No. | Structure | Physical data | IC$_{50}$ (μM) |
|---|---|---|---|
| 42 | 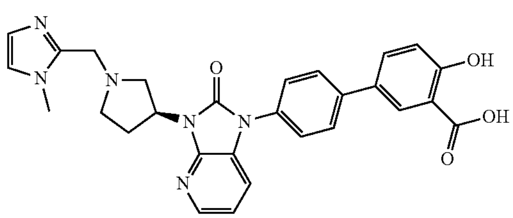 [SMILES: Cn1ccnc1CN1CC[C@H](n2c(=O)n(-c3ccc(-c4ccc(O)c(C(=O)O)c4)cc3)c3cccnc32)C1] | MS (ESI_APCI, m/z): 511 (M + H)$^+$ | 0.32 |
| 43 | 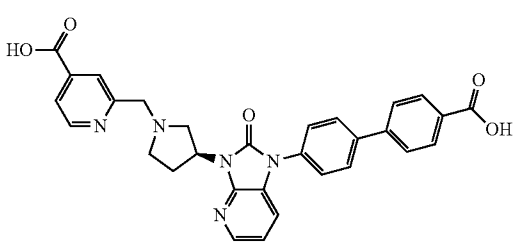 [SMILES: O=C(O)c1ccc(-c2ccc(-n3c(=O)n([C@H]4CCN(Cc5cc(C(=O)O)ccn5)C4)c4ncccc43)cc2)cc1] | MS (ESI_APCI, m/z): 536 (M + H)$^+$ | 0.20 |
| 44 | 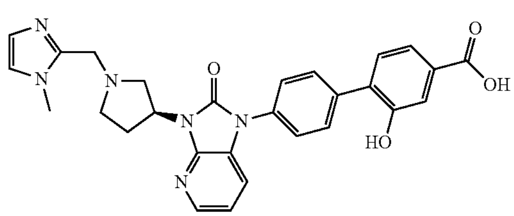 [SMILES: Cn1ccnc1CN1CC[C@H](n2c(=O)n(-c3ccc(-c4ccc(C(=O)O)cc4O)cc3)c3cccnc32)C1] | MS (ESI_APCI, m/z): 511 (M + H)$^+$ | 0.97 |

TABLE 8-continued

| Ex. No. | Structure | Physical data | IC$_{50}$ (μM) |
|---|---|---|---|
| 45 | 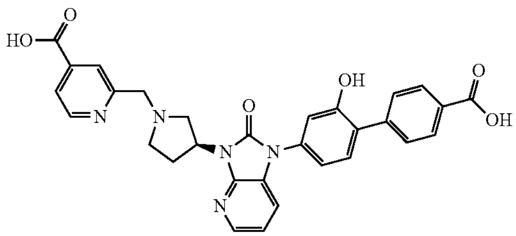 [SMILES: O=C(O)c1ccc(-c2ccc(-n3c(=O)n([C@H]4CCN(Cc5cc(C(=O)O)ccn5)C4)c4ncccc43)cc2O)cc1] | MS (ESI_APCI, m/z): 552 (M + H)$^+$ | 0.27 |
| 46 | 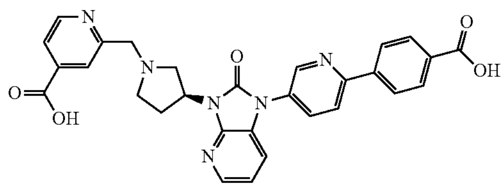 [SMILES: O=C(O)c1ccc(-c2ccc(-n3c(=O)n([C@H]4CCN(Cc5cc(C(=O)O)ccn5)C4)c4ncccc43)cn2)cc1] | MS (ESI_APCI, m/z): 537 (M + H)$^+$ | 0.15 |
| 47 | 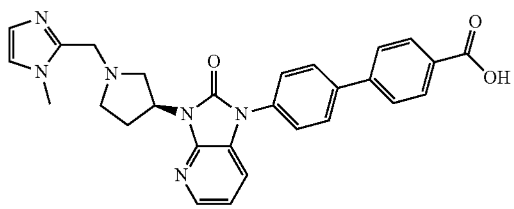 [SMILES: Cn1ccnc1CN1CC[C@H](n2c(=O)n(-c3ccc(-c4ccc(C(=O)O)cc4)cc3)c3cccnc32)C1] | $^1$H-NMR (DMSO-d6) δ ppm: 2.14-2.26 (1H, m), 2.39-2.56 (1H, m), 2.81-3.00 (4H, m), 3.69 (3H, s), 3.73 (2H, s), 5.03-5.16 (1H, m), 6.74 (1H, d, J = 1.1 Hz), 7.07 (1H, d, J = 1.1 Hz), 7.11 (1H, dd, J = 5.2, 7.8 Hz), 7.46 (1H, dd, J = 1.3, 7.8 Hz), 7.68-7.74 (2H, m), 7.85-7.91 (2H, m), 7.91-7.97 (2H, m), 8.03-8.08 (2H, m), 8.09 (1H, dd, J = 1.3, 5.2 Hz), 13.06 (1H, brs) | 0.41 |
| 48 | 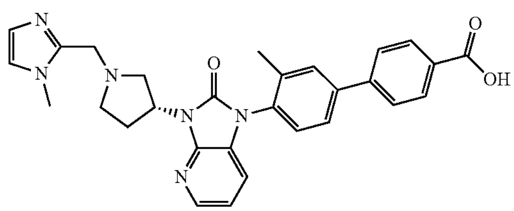 [SMILES: Cc1cc(-c2ccc(C(=O)O)cc2)ccc1-n1c(=O)n([C@@H]2CCN(Cc3nccn3C)C2)c2ncccc21] | MS (ESI_APCI, m/z): 509 (M + H)$^+$ | 0.35 |

TABLE 9

| Ex. No. | Structure | Physical data | IC$_{50}$ (μM) |
|---|---|---|---|
| 49 | 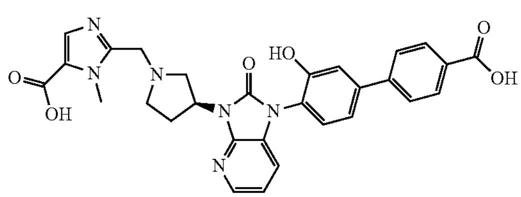 [SMILES: Cn1c(C(=O)O)cnc1CN1CC[C@H](n2c(=O)n(-c3ccc(-c4ccc(C(=O)O)cc4)cc3O)c3cccnc32)C1] | MS (ESI APCI. m/z): 555 (M + H)$^+$ $^1$H-NMR (DMSO-d6) δ ppm: 2.14-2.30 (1H, m), 2.38-2.56 (1H, m), 2.82-3.03 (4H, m), 3.81 (2H, s), 3.91 (3H, s), 5.00-5.14 (1H, m), 7.01-7.09 (2H, m), 7.31 (1H, dd, J = 2.0, 8.2 Hz), 7.36 (1H, d, J = 2.0 Hz), 7.44-7.52 (2H, m), 7.77-7.83 (2H, m), 8.02-8.08 (3H, m), 10.21 (1H, brs), 12.90 (2H, brs) | 0.12 |
| 50 | 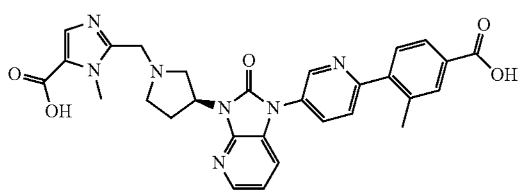 [SMILES: Cc1cc(C(=O)O)ccc1-c1ccc(-n2c(=O)n([C@H]3CCN(Cc4ncc(C(=O)O)n4C)C3)c3ncccc32)cn1] | $^1$H-NMR (DMSO-d6) δ ppm: 2.17-2.29 (1H, m), 2.38-2.55 (4H, m), 2.84-3.03 (4H, m), 3.82 (2H, s), 3.91 (3H, s), 5.04-5.18 (1H, m), 7.13 (1H, dd, J = 5.2, 7.8 Hz), 7.49 (1H, s), 7.55 (1H, dd, J = 1.3, 7.8 Hz), 7.59 (1H, d, J = 8.0 Hz), 7.81 (1H, dd, J = 0.7, 8.4 Hz), 7.86-7.95 (2H, m), 8.12 (1H, dd, J = 1.3, 5.2 Hz), 8.16 (1H, dd, J = 2.6, 8.4 Hz), 8.93 (1H, dd, J = 0.7, 2.6 Hz), 12.90 (2H, brs) | 0.14 |

TABLE 9-continued

| Ex. No. | Structure | Physical data | IC$_{50}$ (μM) |
|---|---|---|---|
| 51 | 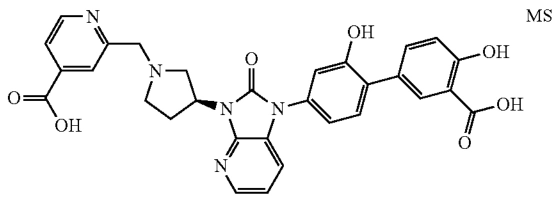 | MS (ESI_APCI, m/z): 568 (M + H)$^+$ | 0.14 |
| 52 | 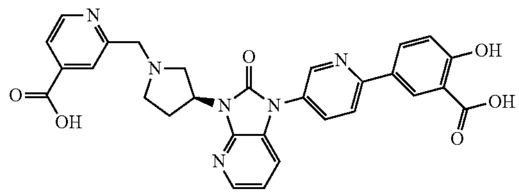 [SMILES: O=C(O)c1ccnc(CN2CC[C@H](n3c(=O)n(-c4ccc(-c5ccc(O)c(C(=O)O)c5)nc4)c4cccnc43)C2)c1] | MS (ESI_APCI, m/z): 553 (M + H)$^+$ | 0.28 |
| 53 | 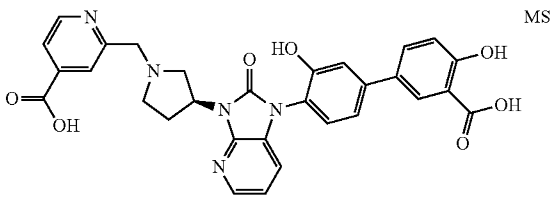 | MS (ESI_APCI, m/z): 568 (M + H)$^+$ | 0.14 |
| 54 | 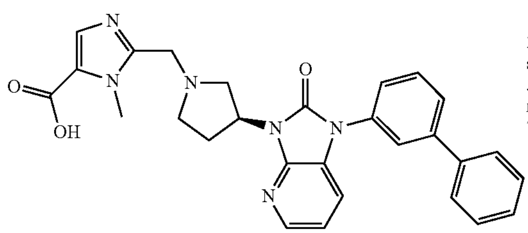 [SMILES: Cn1c(C(=O)O)cnc1CN1CC[C@H](n2c(=O)n(-c3cccc(-c4ccccc4)c3)c3cccnc32)C1] | $^1$H-NMR (DMSO-d6) δ ppm: 2.15-2.28 (1H, m), 2.40-2.55 (1H, m), 2.80-3.03 (4H, m), 3.82 (2H, s), 3.91 (3H, s), 5.03-5.17 (1H, m), 7.10 (1H, dd, J = 5.2, 7.8 Hz), 7.37-7.53 (5H, m), 7.54-7.59 (1H, m), 7.63-7.70 (1H, m), 7.71-7.79 (3H, m), 7.84-7.87 (1H, m), 8.08 (1H, dd, J = 1.4, 5.2 Hz), 12.80 (1H, brs) | 0.77 |
| 55 | 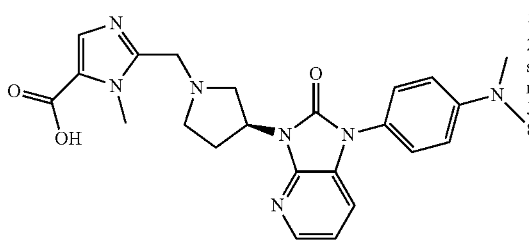 | $^1$H-NMR (DMSO-d6) δ ppm: 2.11-2.26 (1H, m), 2.38-2.57 (1H, m), 2.81-3.02 (10H, m), 3.80 (2H, s), 3.90 (3H, s), 4.98-5.12 (1H, m), 6.79-6.88 (2H, m), 7.05 (1H, dd, J = 5.2, 7.8 Hz), 7.19 (1H, dd, J = 1.4, 7.8 Hz), 7.27-7.33 (2H, m), 7.48 (1H, s), 8.03 (1H, dd, J = 1.4, 5.2 Hz), 12.82 (1H, brs) | 0.49 |

TABLE 10

| Ex. No. | Structure | Physical data | IC$_{50}$ (μM) |
|---|---|---|---|
| 56 | 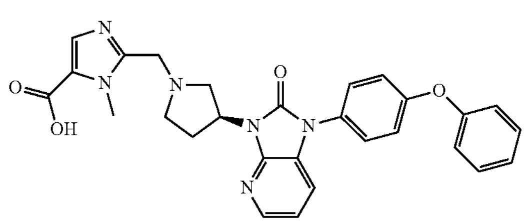 [SMILES: Cn1c(C(=O)O)cnc1CN1CC[C@H](n2c(=O)n(-c3ccc(Oc4ccccc4)cc3)c3cccnc32)C1] | $^1$H-NMR (DMSO-d6) δ ppm: 2.10-2.27 (1H, m), 2.38-2.54 (1H, m), 2.81-3.01 (4H, m), 3.80 (2H, s), 3.90 (3H, s), 5.01-5.14 (1H, m), 7.05-7.24 (6H, m), 7.35 (1H, dd, J = 1.4, 7.8 Hz), 7.41-7.49 (3H, m), 7.53-7.60 (2H, m), 8.07 (1H, dd, J = 1.4, 5.2 Hz), 12.79 (1H, brs) | 0.41 |

TABLE 10-continued

| Ex. No. | Structure | Physical data | IC$_{50}$ (μM) |
|---|---|---|---|
| 57 | 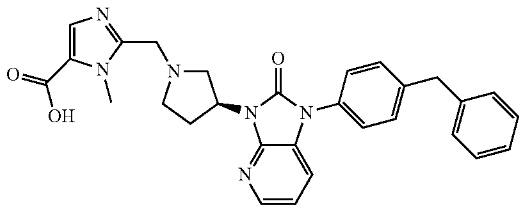 [SMILES: Cn1c(C(=O)O)cnc1CN1CC[C@H](n2c(=O)n(-c3ccc(Cc4ccccc4)cc3)c3cccnc32)C1] | $^1$H-NMR (DMSO-d6) δ ppm: 2.13-2.27 (1H, m), 2.37-2.54 (1H, m), 2.81-3.00 (4H, m), 3.80 (2H, s), 3.89 (3H, s), 4.03 (2H, s), 5.00-5.12 (1H, m), 7.06 (1H, dd, J = 5.2, 7.8 Hz), 7.18-7.24 (1H, m), 7.27-7.36 (5H, m), 7.39-7.50 (5H, m), 8.06 (1H, dd, J = 1.4, 5.2 Hz), 12.80 (1H, brs) | 0.71 |
| 58 | 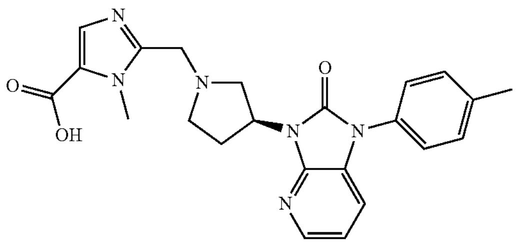 [SMILES: Cc1ccc(-n2c(=O)n([C@H]3CCN(Cc4ncc(C(=O)O)n4C)C3)c3ncccc32)cc1] | $^1$H-NMR (DMSO-d6) δ ppm: 2.14-2.26 (1H, m), 2.36-2.46 (4H, m), 2.82-3.01 (4H, m), 3.81 (2H, s), 3.90 (3H, s), 5.02-5.13 (1H, m), 7.07 (1H, dd, J = 5.2, 7.8 Hz), 7.32 (1H, dd, J = 1.3, 7.8 Hz), 7.35-7.46 (4H, m), 7.49 (1H, s), 8.06 (1H, dd, J = 1.3, 5.2 Hz), 12.73 (1H, brs) | 1.02 |
| 59 | 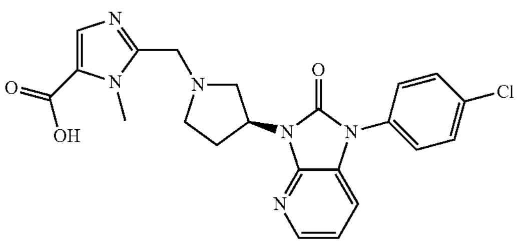 [SMILES: Cn1c(C(=O)O)cnc1CN1CC[C@H](n2c(=O)n(-c3ccc(Cl)cc3)c3cccnc32)C1] | $^1$H-NMR (DMSO-d6) δ ppm: 2.13-2.27 (1H, m), 2.37-2.48 (1H, m), 2.81-3.02 (4H, m), 3.81 (2H, s), 3.90 (3H, s), 5.01-5.13 (1H, m), 7.09 (1H, dd, J = 5.2, 7.8 Hz), 7.40 (1H, dd, J = 1.3, 7.8 Hz), 7.49 (1H, s), 7.58-7.67 (4H, m), 8.08 (1H, dd, J = 1.3, 5.2 Hz), 12.75 (1H, brs) | 0.18 |
| 60 | 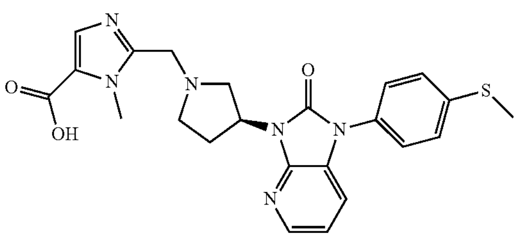 [SMILES: CSc1ccc(-n2c(=O)n([C@H]3CCN(Cc4ncc(C(=O)O)n4C)C3)c3ncccc32)cc1] | $^1$H-NMR (DMSO-d6) δ ppm: 2.14-2.27 (1H, m), 2.38-2.49 (1H, m), 2.54 (3H, s), 2.83-3.00 (4H, m), 3.81 (2H, s), 3.90 (3H, s), 5.01-5.13 (1H, m), 7.08 (1H, dd, J = 5.2, 7.8 Hz), 7.34 (1H, dd, J = 1.3, 7.8 Hz), 7.41-7.54 (5H, m), 8.07 (1H, dd, J = 1.3, 5.2 Hz), 12.76 (1H, brs) | 0.59 |
| 61 | 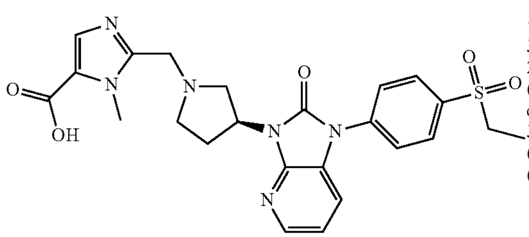 [SMILES: CCS(=O)(=O)c1ccc(-n2c(=O)n([C@H]3CCN(Cc4ncc(C(=O)O)n4C)C3)c3ncccc32)cc1] | $^1$H-NMR (DMSO-d6) δ ppm: 1.15 (3H, t, J = 7.4 Hz), 2.15-2.28 (1H, m), 2.38-2.50 (1H, m), 2.82-3.01 (4H, m), 3.38 (2H, q, J = 7.4 Hz), 3.81 (2H, s), 3.90 (3H, s), 5.04-5.16 (1H, m), 7.13 (1H, dd, J = 5.2, 7.8 Hz), 7.48 (1H, s), 7.58 (1H, dd, J = 1.3, 7.8 Hz), 7.88-7.93 (2H, m), 8.04-8.09 (2H, m), 8.12 (1H, dd, J = 1.3, 5.2 Hz), 12.82 (1H, brs) | 7.07 |
| 62 | 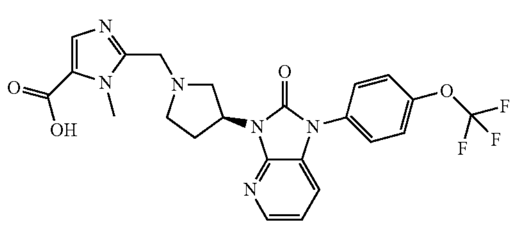 [SMILES: Cn1c(C(=O)O)cnc1CN1CC[C@H](n2c(=O)n(-c3ccc(OC(F)(F)F)cc3)c3cccnc32)C1] | $^1$H-NMR (DMSO-d6) δ ppm: 2.14-2.28 (1H, m), 2.38-2.49 (1H, m), 2.82-3.02 (4H, m), 3.81 (2H, s), 3.90 (3H, s), 5.03-5.14 (1H, m), 7.09 (1H, dd, J = 5.2, 7.8 Hz), 7.44 (1H, dd, J = 1.3, 7.8 Hz), 7.49 (1H, s), 7.54-7.61 (2H, m), 7.69-7.77 (2H, m), 8.09 (1H, dd, J = 1.3, 5.2 Hz), 12.77 (1H, brs) | 1.85 |

TABLE 11

| Ex. No. | Structure | Physical data | IC$_{50}$ (μM) |
|---|---|---|---|
| 63 | 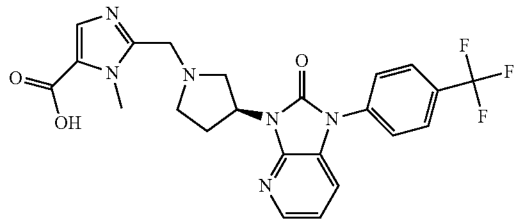 [SMILES: Cn1c(C(=O)O)cnc1CN1CC[C@H](n2c(=O)n(-c3ccc(C(F)(F)F)cc3)c3cccnc32)C1] | $^{1}$H-NMR (DMSO-d6) δ ppm: 2.15-2.28 (1H, m), 2.38-2.49 (1H, m), 2.81-3.02 (4H, m), 3.82 (2H, s), 3.90 (3H, s), 5.03-5.16 (1H, m), 7.12 (1H, dd, J = 5.2, 7.8 Hz), 7.49 (1H, s), 7.53 (1H, dd, J = 1.3, 7.8 Hz), 7.82-7.88 (2H, m), 7.92-7.98 (2H, m), 8.11 (1H, dd, J = 1.3, 5.2 Hz), 12.80 (1H, brs) | 1.92 |
| 64 | 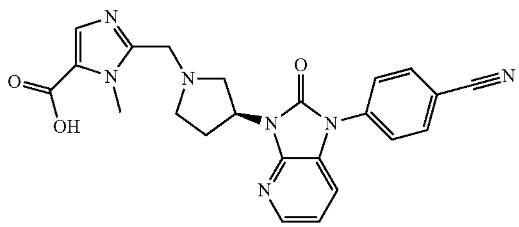 [SMILES: Cn1c(C(=O)O)cnc1CN1CC[C@H](n2c(=O)n(-c3ccc(C#N)cc3)c3cccnc32)C1] | $^{1}$H-NMR (DMSO-d6) δ ppm: 2.13-2.27 (1H, m), 2.37-2.49 (1H, m), 2.82-3.01 (4H, m), 3.81 (2H, s), 3.90 (3H, s), 5.03-5.14 (1H, m), 7.12 (1H, dd, J = 5.2, 7.8 Hz), 7.48 (1H, s), 7.54 (1H, dd, J = 1.3, 7.8 Hz), 7.80-7.86 (2H, m), 8.02-8.08 (2H, m), 8.11 (1H, dd, J = 1.3, 5.2 Hz), 12.79 (1H, brs) | 7.89 |
| 65 | 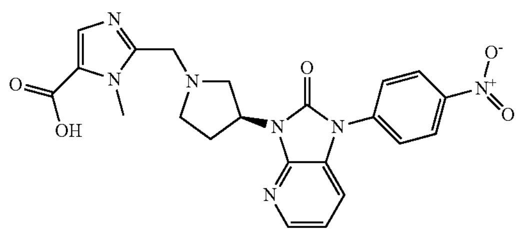 [SMILES: Cn1c(C(=O)O)cnc1CN1CC[C@H](n2c(=O)n(-c3ccc([N+](=O)[O-])cc3)c3cccnc32)C1] | $^{1}$H-NMR (DMSO-d6) δ ppm: 2.14-2.28 (1H, m), 2.37-2.49 (1H, m), 2.82-3.01 (4H, m), 3.81 (2H, s), 3.90 (3H, s), 5.04-5.16 (1H, m), 7.14 (1H, dd, J = 5.2, 7.8 Hz), 7.47 (1H, s), 7.60 (1H, dd, J = 1.3, 7.9 Hz), 7.88-7.95 (2H, m), 8.13 (1H, dd, J = 1.3, 5.2 Hz), 8.39-8.45 (2H, m), 12.82 (1H, brs) | 2.40 |
| 66 | 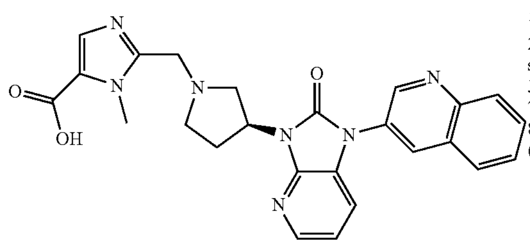 [SMILES: Cn1c(C(=O)O)cnc1CN1CC[C@H](n2c(=O)n(-c3cnc4ccccc4c3)c3cccnc32)C1] | $^{1}$H-NMR (DMSO-d6) δ ppm: 2.17-2.30 (1H, m), 2.42-2.54 (1H, m), 2.83-3.04 (4H, m), 3.82 (2H, s), 3.91 (3H, s), 5.06-5.19 (1H, m), 7.13 (1H, dd, J = 5.2, 7.8 Hz), 7.48 (1H, s), 7.58 (1H, dd, J = 1.3, 7.8 Hz), 7.69-7.75 (1H, m), 7.83-7.89 (1H, m), 8.08-8.15 (3H, m), 8.65 (1H, d, J = 2.5 Hz), 9.12 (1H, d, J = 2.5 Hz), 12.82 (1H, brs) | 1.17 |
| 67 | 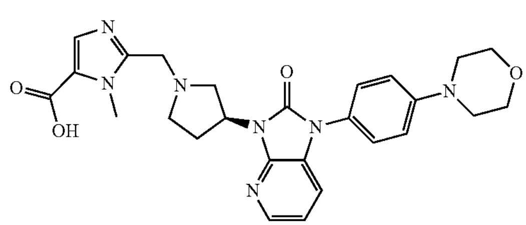 [SMILES: Cn1c(C(=O)O)cnc1CN1CC[C@H](n2c(=O)n(-c3ccc(N4CCOCC4)cc3)c3cccnc32)C1] | $^{1}$H-NMR (DMSO-d6) δ ppm: 2.12-2.27 (1H, m), 2.37-2.49 (1H, m), 2.81-3.01 (4H, m), 3.14-3.22 (4H, m), 3.72-3.79 (4H, m), 3.80 (2H, s), 3.90 (3H, s), 5.00-5.13 (1H, m), 7.02-7.13 (3H, m), 7.25 (1H, dd, J = 1.4, 7.8 Hz), 7.34-7.40 (2H, m), 7.48 (1H, s), 8.04 (1H, dd, J = 1.4, 5.2 Hz), 12.77 (1H, brs) | 0.52 |
| 68 | 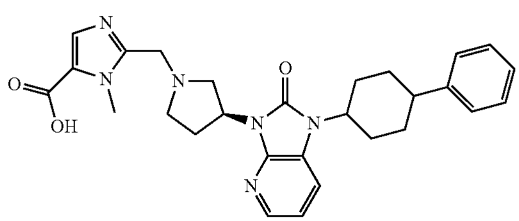 [SMILES: Cn1c(C(=O)O)cnc1CN1CC[C@H](n2c(=O)n(C3CCC(c4ccccc4)CC3)c3cccnc32)C1] | $^{1}$H-NMR (DMSO-d6) δ ppm: 1.58-1.69 (2H, m), 1.88-2.57 (9H, m), 2.74-3.12 (4H, m), 3.74 (2H, s), 3.87 (3H, s), 4.27-4.39 (1H, m), 4.89-5.01 (1H, m), 6.93-7.00 (1H, m), 7.12 (1H, dd, J = 1.2, 8.0 Hz), 7.21-7.27 (1H, m), 7.33-7.49 (5H, m), 7.94 (1H, dd, J = 1.2, 5.3 Hz), 12.79 (1H, brs) | 8.15 |

TABLE 11-continued

| Ex. No. | Structure | Physical data | IC$_{50}$ (μM) |
|---|---|---|---|
| 69 | 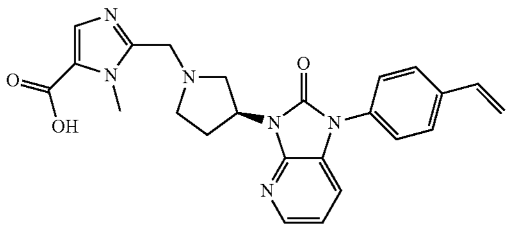 [SMILES: C=Cc1ccc(-n2c(=O)n([C@H]3CCN(Cc4ncc(C(=O)O)n4C)C3)c3ncccc32)cc1] | $^1$H-NMR (DMSO-d6) δ ppm: 2.14-2.27 (1H, m), 2.36-2.56 (1H, m), 2.83-3.02 (4H, m), 3.82 (2H, s), 3.90 (3H, s), 5.02-5.13 (1H, m), 5.35 (1H, d, J = 11.0 Hz), 5.93 (1H, d, J = 17.7 Hz), 6.82 (1H, dd, J = 11.0, 17.7 Hz), 7.09 (1H, dd, J = 5.2, 7.8 Hz), 7.40 (1H, dd, J = 1.3, 7.8 Hz), 7.49 (1H, s), 7.53-7.58 (2H, m), 7.64-7.71 (2H, m), 8.08 (1H, dd, J = 1.3, 5.2 Hz), 12.77 (1H, brs) | 0.50 |

TABLE 12

| Ex. No. | Structure | Physical data | IC$_{50}$ (μM) |
|---|---|---|---|
| 70 | 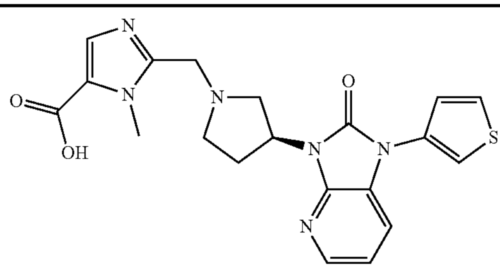 | $^1$H-NMR (DMSO-d6) δ ppm: 2.14-2.26 (1H, m), 2.37-2.48 (1H, m), 2.82-3.01 (4H, m), 3.81 (2H, s), 3.90 (3H, s), 5.01-5.13 (1H, m), 7.12 (1H, dd, J = 5.2, 7.8 Hz), 7.43 (1H, dd, J = 1.4, 5.2 Hz), 7.48 (1H, s), 7.50 (1H, dd, J = 1.4, 7.8 Hz), 7.75 (1H, dd, J = 3.2, 5.2 Hz), 7.81 (1H, dd, J = 1.4, 3.2 Hz), 8.08 (1H, dd, J = 1.4, 5.2 Hz), 12.76 (1H, brs) | 1.45 |
| 71 | 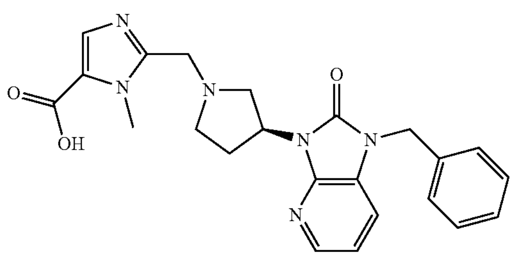 [SMILES: Cn1c(C(=O)O)cnc1CN1CC[C@H](n2c(=O)n(Cc3ccccc3)c3cccnc32)C1] | $^1$H-NMR (DMSO-d6) δ ppm: 2.12-2.25 (1H, m), 2.31-2.44 (1H, m), 2.80-3.00 (4H, m), 3.81 (2H, s), 3.89 (3H, s), 4.98-5.10 (3H, m), 7.03 (1H, dd, J = 5.2, 7.8 Hz), 7.23-7.37 (5H, m), 7.44 (1H, dd, J = 1.4, 7.8 Hz), 7.49 (1H, s), 7.99 (1H, dd, J = 1.4, 5.2 Hz), 12.77 (1H, brs) | 13.9 |
| 72 | 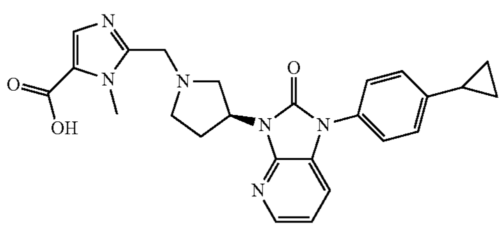 [SMILES: Cn1c(C(=O)O)cnc1CN1CC[C@H](n2c(=O)n(-c3ccc(C4CC4)cc3)c3cccnc32)C1] | $^1$H-NMR (DMSO-d6) δ ppm: 0.69-0.78 (2H, m), 0.96-1.06 (2H, m), 1.96-2.06 (1H, m), 2.14-2.27 (1H, m), 2.36-2.49 (1H, m), 2.81-3.01 (4H, m), 3.81 (2H, s), 3.90 (3H, s), 5.01-5.14 (1H, m), 7.06 (1H, dd, J = 5.2, 7.8 Hz), 7.23-7.28 (2H, m), 7.31 (1H, dd, J = 1.3, 7.8 Hz), 7.39-7.43 (2H, m), 7.49 (1H, s), 8.06 (1H, dd, J = 1.3, 5.2 Hz), 12.77 (1H, brs) | 0.10 |
| 73 | 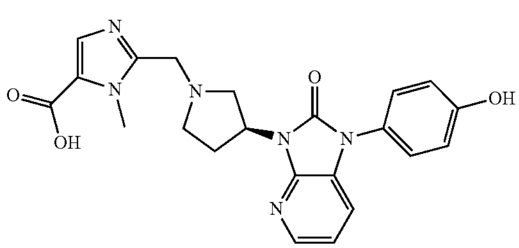 [SMILES: Cn1c(C(=O)O)cnc1CN1CC[C@H](n2c(=O)n(-c3ccc(O)cc3)c3cccnc32)C1] | $^1$H-NMR (DMSO-d6) δ ppm: 2.13-2.26 (1H, m), 2.37-2.48 (1H, m), 2.81-2.99 (4H, m), 3.80 (2H, s), 3.90 (3H, s), 5.00-5.11 (1H, m), 6.87-6.93 (2H, m), 7.05 (1H, dd, J = 5.2, 7.8 Hz), 7.23 (1H, dd, J = 1.4, 7.8 Hz), 7.28-7.35 (2H, m), 7.47 (1H, s), 8.04 (1H, dd, J = 1.4, 5.2 Hz), 9.82 (1H, brs), 12.77 (1H, brs) | 3.00 |
| 74 | 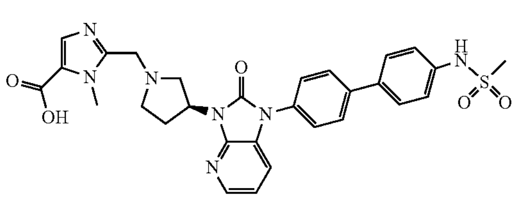 [SMILES: Cn1c(C(=O)O)cnc1CN1CC[C@H](n2c(=O)n(-c3ccc(-c4ccc(NS(C)(=O)=O)cc4)cc3)c3cccnc32)C1] | $^1$H-NMR (DMSO-d6) δ ppm: 2.15-2.29 (1H, m), 2.39-2.48 (1H, m), 2.83-3.02 (4H, m), 3.05 (3H, s), 3.82 (2H, s), 3.91 (3H, s), 5.03-5.15 (1H, m), 7.10 (1H, dd, J = 5.2, 7.8 Hz), 7.30-7.36 (2H, m), 7.44 (1H, dd, J = 1.3, 7.8 Hz), 7.49 (1H, s), 7.61-7.67 (2H, m), 7.70-7.76 (2H, m), 7.80-7.86 (2H, m), 8.09 (1H, dd, J = 1.3, 5.2 Hz), 9.93 (1H, s), 12.78 (1H, brs) | 1.85 |

TABLE 12-continued

| Ex. No. | Structure | Physical data | IC$_{50}$ (μM) |
|---|---|---|---|
| 75 | 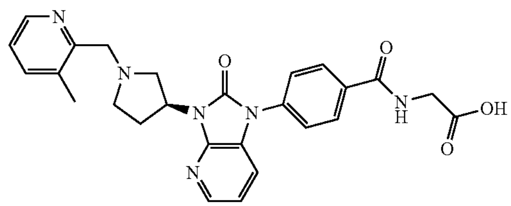 [SMILES: Cc1cccnc1CN1CC[C@H](n2c(=O)n(-c3ccc(C(=O)NCC(=O)O)cc3)c3cccnc32)C1] | MS (ESI_APCI, m/z): 487 (M + H)$^+$ | 99.90 |
| 76 | 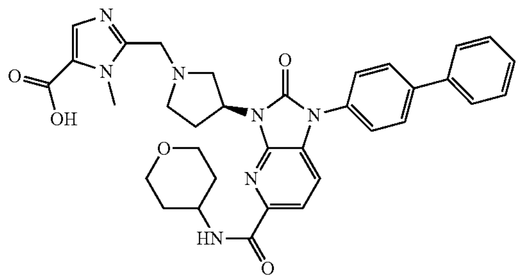 [SMILES: Cn1c(C(=O)O)cnc1CN1CC[C@H](n2c(=O)n(-c3ccc(-c4ccccc4)cc3)c3ccc(C(=O)NC4CCOCC4)nc32)C1] | $^1$H-NMR (DMSO-d6) δ ppm: 1.61-1.85 (4H, m), 2.22-2.52 (2H, m), 2.84-2.99 (3H, m), 3.04-3.12 (1H, m), 3.38-3.48 (2H, m), 3.77-3.95 (7H, m), 3.98-4.12 (1H, m), 5.30-5.43 (1H, m), 7.38-7.45 (1H, m), 7.47-7.57 (4H, m), 7.65-7.71 (2H, m), 7.72-7.82 (3H, m), 7.85-7.92 (2H, m), 8.28 (1H, d, J = 8.3 Hz), 12.79 (1H, brs) | 9.74 |

TABLE 13

| Ex. No. | Structure | Physical data | IC$_{50}$ (μM) |
|---|---|---|---|
| 77 | 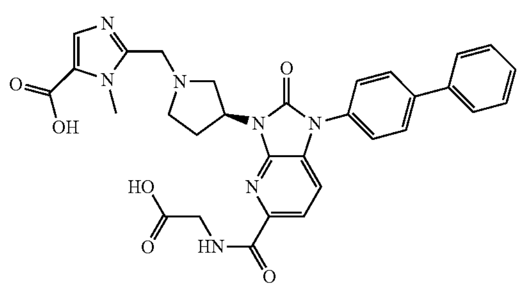 [SMILES: Cn1c(C(=O)O)cnc1CN1CC[C@H](n2c(=O)n(-c3ccc(-c4ccccc4)cc3)c3ccc(C(=O)NCC(=O)O)nc32)C1] | $^1$H-NMR (DMSO-d6) δ ppm: 2.19-2.34 (1H, m), 2.38-2.51 (1H, m), 2.85-3.08 (4H, m), 3.80-3.91 (5H, m), 4.01 (2H, d, J = 5.9 Hz), 5.26-5.39 (1H, m), 7.38-7.45 (1H, m), 7.47-7.58 (4H, m), 7.66-7.72 (2H, m), 7.73-7.82 (3H, m), 7.85-7.92 (2H, m), 8.84 (1H, t, J = 5.9 Hz) | 0.61 |
| 78 | 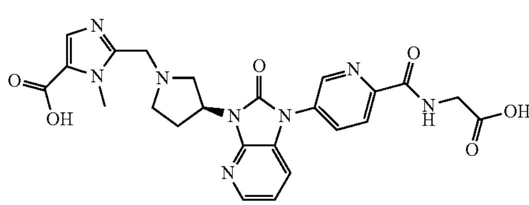 [SMILES: Cn1c(C(=O)O)cnc1CN1CC[C@H](n2c(=O)n(-c3ccc(C(=O)NCC(=O)O)nc3)c3cccnc32)C1] | $^1$H-NMR (DMSO-d6) δ ppm: 2.15-2.29 (1H, m), 2.39-2.50 (1H, m), 2.83-3.02 (4H, m), 3.82 (2H, s), 3.91 (3H, s), 3.98 (2H, d, J = 6.0 Hz), 5.03-5.16 (1H, m), 7.13 (1H, dd, J = 5.2, 7.8 Hz), 7.48 (1H, s), 7.59 (1H, dd, J = 1.3, 7.8 Hz), 8.12 (1H, dd, J = 1.3, 5.2 Hz), 8.20-8.29 (2H, m), 8.93 (1H, dd, J = 0.8, 2.3 Hz), 9.06 (1H, t, J = 6.0 Hz), 12.80 (2H, brs) | 11.0 |
| 79 | 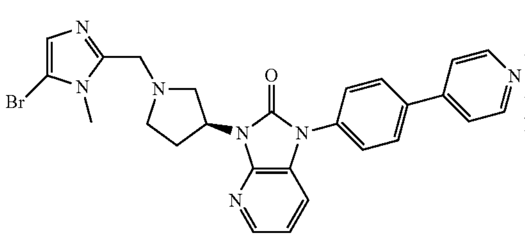 [SMILES: Cn1c(Br)cnc1CN1CC[C@H](n2c(=O)n(-c3ccc(-c4ccncc4)cc3)c3cccnc32)C1] | $^1$H-NMR (CDCl3) δ ppm: 2.25-2.40 (1H, m), 2.52-2.65 (1H, m), 2.89-2.98 (1H, m), 3.00-3.10 (3H, m), 3.71 (3H, s), 3.80-3.91 (2H, m), 5.22-5.34 (1H, m), 6.90 (1H, s), 7.01 (1H, dd, J = 5.2, 7.8 Hz), 7.34 (1H, dd, J = 1.4, 7.8 Hz), 7.51-7.56 (2H, m), 7.64-7.68 (2H, m), 7.78-7.82 (2H, m), 8.10 (1H, dd, J = 1.4, 5.2 Hz), 8.69-8.72 (2H, m) | 32.85 |

TABLE 13-continued

| Ex. No. | Structure | Physical data | IC$_{50}$ (μM) |
|---|---|---|---|
| 80 | 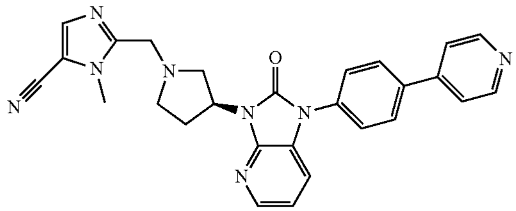 [SMILES: Cn1c(C#N)cnc1CN1CC[C@H](n2c(=O)n(-c3ccc(-c4ccncc4)cc3)c3cccnc32)C1] | $^1$H-NMR (CDCl3) δ ppm: 2.29-2.41 (1H, m), 2.54-2.64 (1H, m), 2.86-2.95 (1H, m), 3.02-3.15 (3H, m), 3.89-3.91 (5H, m), 5.23-5.37 (1H, m), 7.03 (1H, dd, J = 5.2, 7.8 Hz), 7.35 (1H, dd, J = 1.4, 7.8 Hz), 7.51-7.56 (3H, m), 7.63-7.69 (2H, m), 7.78-7.83 (2H, m), 8.10 (1H, dd, J = 1.4, 5.2 Hz), 8.68-8.74 (2H, m) | 65.88 |
| 81 | 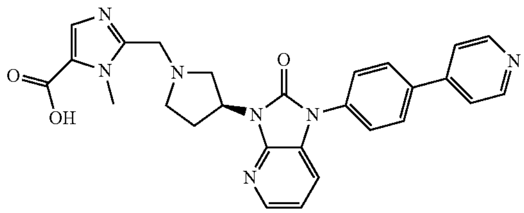 [SMILES: Cn1c(C(=O)O)cnc1CN1CC[C@H](n2c(=O)n(-c3ccc(-c4ccncc4)cc3)c3cccnc32)C1] | $^1$H-NMR (DMSO-d6) δ ppm: 2.16-2.28 (1H, m), 2.39-2.48 (1H, m), 2.84-3.03 (4H, m), 3.82 (2H, s), 3.91 (3H, s), 5.04-5.15 (1H, m), 7.11 (1H, dd, J = 5.2, 7.8 Hz), 7.44-7.51 (2H, m), 7.71-7.77 (2H, m), 7.77-7.82 (2H, m), 7.98-8.04 (2H, m), 8.10 (1H, dd, J = 1.3, 5.2 Hz), 8.65-8.72 (2H, m), 12.74 (1H, brs) | 0.50 |
| 82 | 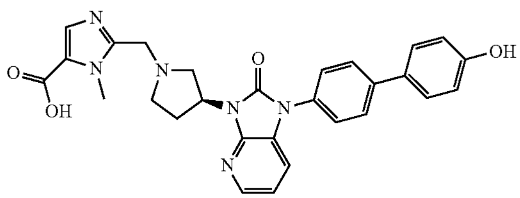 [SMILES: Cn1c(C(=O)O)cnc1CN1CC[C@H](n2c(=O)n(-c3ccc(-c4ccc(O)cc4)cc3)c3cccnc32)C1] | $^1$H-NMR (DMSO-d6) δ ppm: 2.14-2.28 (1H, m), 2.39-2.49 (1H, m), 2.81-3.00 (4H, m), 3.73 (2H, s), 3.93 (3H, s), 5.03-5.15 (1H, m), 6.86-6.94 (2H, m), 7.09 (1H, dd, J = 5.2, 7.8 Hz), 7.13 (1H, s), 7.41 (1H, dd, J = 1.2, 7.8 Hz), 7.53-7.63 (4H, m), 7.72-7.79 (2H, m), 8.08 (1H, dd, J = 1.2, 5.2 Hz) | 0.13 |
| 83 | 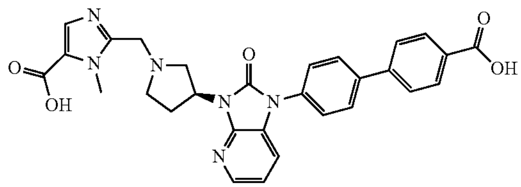 [SMILES: Cn1c(C(=O)O)cnc1CN1CC[C@H](n2c(=O)n(-c3ccc(-c4ccc(C(=O)O)cc4)cc3)c3cccnc32)C1] | MS (ESI_APCI, m/z): 539 (M + H)$^+$ | 0.14 |

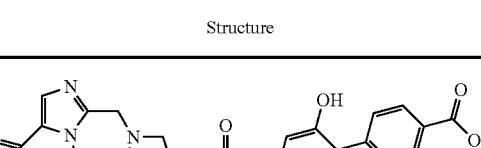

TABLE 14

| Ex. No. | Structure | Physical data | IC$_{50}$ (μM) |
|---|---|---|---|
| 84 | 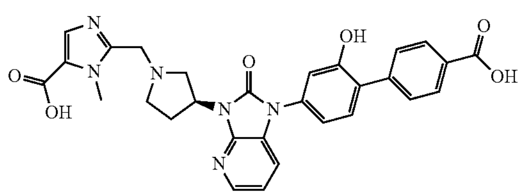 [SMILES: Cn1c(C(=O)O)cnc1CN1CC[C@H](n2c(=O)n(-c3ccc(-c4ccc(C(=O)O)cc4)c(O)c3)c3cccnc32)C1] | MS (ESI_APCI, m/z): 555 (M + H)$^+$<br>$^1$H-NMR (DMSO-d6) δ ppm: 2.14-2.28 (1H, m), 2.38-2.53 (1H, m), 2.83-3.03 (4H, m), 3.81 (2H, s), 3.91 (3H, s), 5.04-5.16 (1H, m), 7.08-7.14 (2H, m), 7.21 (1H, d, J = 2.1 Hz), 7.46 (1H, s), 7.47-7.52 (2H, m), 7.72-7.76 (2H, m), 7.97-8.02 (2H, m), 8.09 (1H, dd, J = 1.3, 5.2 Hz), 10.30 (1H, brs), 12.90 (2H, brs) | 0.15 |
| 85 | 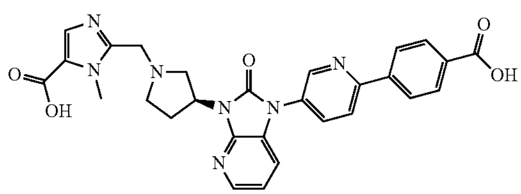 [SMILES: Cn1c(C(=O)O)cnc1CN1CC[C@H](n2c(=O)n(-c3ccc(-c4ccc(C(=O)O)cc4)nc3)c3cccnc32)C1] | $^1$H-NMR (DMSO-d6) δ ppm: 2.15-2.30 (1H, m), 2.40-2.56 (1H, m), 2.82-3.04 (4H, m), 3.82 (2H, s), 3.91 (3H, s), 5.05-5.17 (1H, m), 7.13 (1H, dd, J = 5.2, 7.8 Hz), 7.49 (1H, s), 7.56 (1H, dd, J = 1.3, 7.8 Hz), 8.06-8.11 (2H, m), 8.12 (1H, dd, J = 1.3, 5.2 Hz), 8.18 (1H, dd, J = 2.6, 8.6 Hz), 8.25-8.32 (3H, m), 8.95 (1H, dd, J = 0.5, 2.6 Hz), 12.95 (2H, brs) | 0.18 |

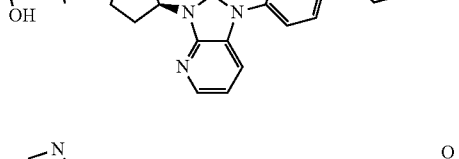

TABLE 14-continued

| Ex. No. | Structure | Physical data | IC$_{50}$ (μM) |
| --- | --- | --- | --- |
| 86 | 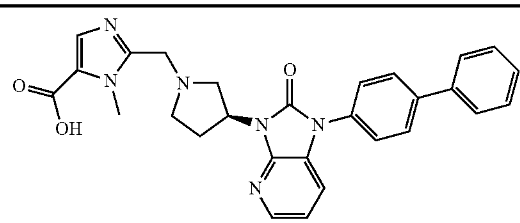 | MS (ESI_APCI, m/z): 495 (M + H)$^+$ | 0.27 |
| 87 | 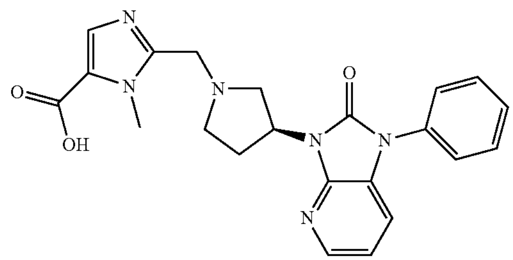 [SMILES: Cn1c(C(=O)O)cnc1CN1CC[C@H](n2c(=O)n(-c3ccccc3)c3cccnc32)C1] | MS (ESI_APCI, m/z): 419 (M + H)$^+$ | 3.99 |
| 88 | 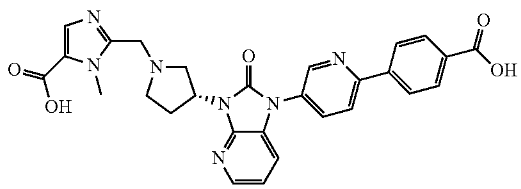 [SMILES: Cn1c(C(=O)O)cnc1CN1CC[C@@H](n2c(=O)n(-c3ccc(-c4ccc(C(=O)O)cc4)nc3)c3cccnc32)C1] | MS (ESI_APCI, m/z): 540 (M + H)$^+$ | 0.27 |
| 89 | 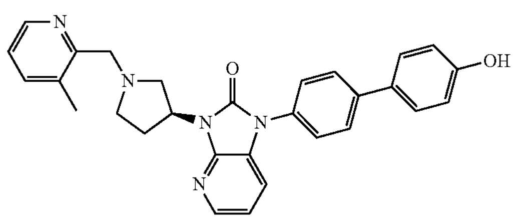 [SMILES: Cc1cccnc1CN1CC[C@H](n2c(=O)n(-c3ccc(-c4ccc(O)cc4)cc3)c3cccnc32)C1] | MS (ESI_APCI, m/z): 478 (M + H)$^+$ | 3.17 |

TABLE 15

| 90 | | MS (ESI_APCI, m/z): 463 (M + H)$^+$ | 7.46 |
| --- | --- | --- | --- |
| 91 | | MS (ESI_APCI, m/z): 506 (M + H)$^+$ | 0.96 |

Test Example 1 PHD2 Inhibitory Test (1) Expression and Preparation of Human PHD2$_{184-418}$ Human PHD2$_{184-418}$ containing amino acid residues 184 to 418 of the protein represented by CAC42509 (GenBank accession ID) was expressed and prepared by the following method.

An expression construct of human PHD2$_{184-418}$ containing N-terminal histidine tag was introduced into pET-30a (+) vector, and the sequence was confirmed. This vector was introduced into BL21 (DE3) strain and cultured at 37° C. in LB medium containing antibiotics. After culturing, a cell lysis solution was added to the cells, and then the cells were disrupted by sonication. The disrupted suspension was centrifuged and the supernatant was purified by Ni column to give human PHD2$_{184-418}$.

(2) Methods

Human HIF-1α$_{556-574}$ (FITC-labeled HIF-1α$_{556-574}$), containing N-terminal FITC-Ahx, containing amino acid residues 556 to 574 (partial peptide) of HIF-1α was used as a substrate. Using FITC-labeled HIF-1α$_{556-574}$, the competitive inhibition between 2-oxoglutarate and test compounds (PHD inhibitor) was evaluated based on the change in fluorescence polarization by the following method.

An enzyme (human PHD2$_{184-418}$) and the substrate were diluted with an assay buffer (pH 7.4) containing 10 mM HEPES, 150 mM NaCl, 10 μM MnCl$_2$-4H$_2$O, 2 μM 2-oxoglutarate and 0.05% Tween-20. Test compounds were diluted with DMSO. Test compounds and human PHD2$_{184-418}$ was added to the 384-well plate (Corning, black, opaque bottom) in advance. The reaction was started by the addition of FITC-labeled HIF-1α$_{556-574}$. After incubating at 37° C. for 60 minutes, fluorescence polarization (excitation wavelength: 470 nm, fluorescence wavelength: 530 nm) was measured by PHERAstar FSX (BMG Labtech). Fluorescence polarization of each well was measured, and human PHD2 binding inhibitory activity of test compounds was calculated based on the value of test compound-free group.

(3) Results

As shown in above tables, the compounds of the present invention inhibited binding between PHD2 and HIF-1α, and thus it is demonstrated that the compounds of the present invention are useful as PHD2 inhibitor.

Test Example 2 Therapeutic Effect in Colitis Model (1) TNBS Induced Colitis Model Rat It is known that inflammation is locally occurred in large intestine when TNBS is administered into large intestine, and then the intestinal permeability is increased due to breakdown of barrier function in intestine, and hence suppressive effect on the intestinal permeability based on oral administration of test compounds was evaluated as an indicator of medicinal efficacy.

(2) Methods

SD rats: 8-weeks-old male SLC (Japan SLC) were used. Under pentobarbital anesthesia, 300 μL of TNBS (28 mg/mL) prepared by 50% ethanol was administered at a point 8 cm from anus in large intestine to cause inflammation. To the solvent-treated group was administrated 300 μL of 50% ethanol. Animals were fasted for 48 hours prior to administration of TNBS. Test compounds (3 mg/kg) prepared by 0.05% methylcellulose solution were orally administered once a day from next day, and it was administered for a total of 3 days. After administering for 3 days, 50 mg/kg FITC was orally administered at 4 hours after administration. Blood samples were collected from jugular vein under isoflurane anesthesia after 4 hours. The serum was centrifuged and fluorescence intensity was detected by PHERAstar FSX (BMG Labtech) to measure the concentration of FITC permeating into circulating blood through the mesentery. The suppressive rate on the intestinal permeability of test compounds was calculated based on the value of test compounds-free group as 0 and the value of TNBS-untreated group as 100.

(3) Results

The suppressive rate (%, mean) on the intestinal permeability of each test compound (Inhibition) is shown below.

TABLE 16

| Ex. No. | Inhibition (%) | Ex. No. | Inhibition (%) |
|---|---|---|---|
| 39 | 95 | 47 | 85 |
| 40 | 84 | 49 | 82 |
| 41 | 74 | 82 | 96 |
| 43 | 59 | 83 | 85 |
| 45 | 51 | 84 | 117 |
| 46 | 63 | 85 | 101 |

The intestinal permeability of FITC, which was increased due to administration of TNBS, was suppressed by administration of the compounds of the present invention, and thus it is demonstrated that the compounds of the present invention are useful as agents for the treatment of inflammatory bowel diseases.

Test Example 3 Concentration of Compounds in Large Intestine Tissue (1) Rat PK Study Test compounds (3 mg/kg/5 mL) prepared by 0.05% methylcellulose were orally administered to non-fasted rats (SD, 8-weeks-old, male, Japan SLC). Blood samples were collected from jugular vein at 0.25, 0.5, 1, 2, 4, 6 and 8 hours after the administration. Laparotomy was performed under isoflurane anesthesia and large intestine was isolated. Collected distal large intestine (about 5 cm) was cut open, and then the large intestine was washed with saline on a dish. After washing, the large intestine was minced by a small scissors. About 150 mg thereof was moved to tube. To the tube was added 100 μL of saline, the mixture was homogenized using shake master (1000 rpm×30 minutes). Samples were prepared by the addition with quadruple volume of saline as final volume. The concentrations of the test compound in large intestine tissue and plasma were measured through a quantitative analysis using liquid chromatography-mass spectrometry (LC/MS).

(2) Concentration of Compounds in Large Intestine Tissue and Plasma

As shown in the following table, it was demonstrated that the compounds of the present invention have higher concentration in large intestine tissue than concentration in plasma. Accordingly, preferable compounds of the present invention are PHD2 inhibitor that act specifically on large intestine tissue.

TABLE 17

| Ex. No. | Cmax | AUC | Plasma | Colon | C/P |
|---|---|---|---|---|---|
| 39 | 7 | 2090 | 3 | 214 | 71 |
| 40 | <1 | NC | <1 | 209 | >209 |
| 43 | 8 | 2111 | 2 | 84 | 42 |
| 45 | 2 | 401 | <1 | 87 | >87 |
| 46 | 3 | 314 | <1 | 174 | >174 |

TABLE 17-continued

| Ex. No. | Cmax | AUC | Plasma | Colon | C/P |
|---|---|---|---|---|---|
| 47 | 60 | 20011 | 18 | 317 | 18 |
| 49 | 4 | 898 | <1 | 201 | >201 |
| 83 | 5 | 1292 | <1 | 54 | >54 |
| 84 | 1 | 76 | <1 | 99 | >99 |
| 85 | 1 | 117 | <1 | 164 | >164 |

Symbols in the table have the following meaning.
Cmax: maximum plasma concentration of test compounds in the case of oral administration (ng/mL)
AUC: area under the plasma test compound concentration-time curve (ng * min/mL)
Plasma: plasma test compound concentration after 8 hours (ng/mL)
Colon: concentrations of the test compound in large intestine tissue after 8 hours (ng/g)
C/P: ratio of the above Colon and Plasma
NC: Not Calculated (below the lower limit of calculation)

INDUSTRIAL APPLICABILITY

The compounds of the present invention or pharmaceutically acceptable salts thereof are useful as agents for the treatment of inflammatory bowel diseases.

The invention claimed is:
1. A compound represented by the formula (I):

[Chem. 1]

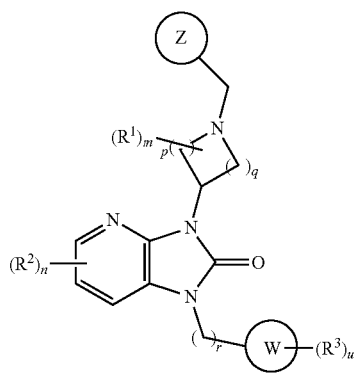

(I)

wherein
ring W is $C_{6-10}$ aryl, 5- or 6-membered heteroaryl, 9- or 10-membered heteroaryl, $C_{3-8}$ cycloalkyl or 3- to 8-membered heterocycloalkyl;
ring Z is a group selected from the group consisting of following (a) to (c):

[Chem. 2]

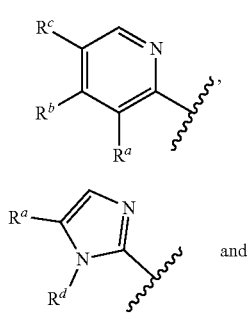

[Chem. 3]

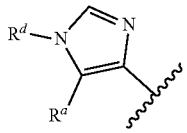

(c)

wherein
$R^a$, $R^b$ and $R^c$ are each independently a hydrogen atom, a halogen atom, $C_{1-6}$ alkyl, cyano, hydroxy or carboxy; and
$R^d$ is a hydrogen atom or $C_{1-6}$ alkyl;
$R^1$ is a hydrogen atom, a halogen atom, $C_{1-6}$ alkyl, cyano, hydroxy or carboxy, wherein when m is 2 or 3, two or more $R^1$s may be different from each other;
$R^2$ is a hydrogen atom, a halogen atom, $C_{1-6}$ alkyl, halo $C_{1-6}$ alkyl, $C_{1-6}$ alkoxy, hydroxy, —$CO_2R^4$ or —$CONR^5R^{5'}$, wherein when n is 2 or 3, two or more $R^2$s may be different from each other;
$R^4$ is a hydrogen atom or $C_{1-6}$ alkyl; and
$R^5$ and $R^{5'}$ are each independently a hydrogen atom, $C_{1-6}$ alkyl, carboxy $C_{1-6}$ alkyl, hydroxy $C_{1-6}$ alkyl, halo $C_{1-6}$ alkyl, $C_{3-8}$ cycloalkyl or 3- to 8-membered heterocycloalkyl;
$R^3$ is a hydrogen atom, a halogen atom, $C_{1-6}$ alkyl, halo $C_{1-6}$ alkyl, $C_{1-6}$ alkoxy, halo $C_{1-6}$ alkoxy, $C_{2-6}$ alkenyl, $C_{2-6}$ alkynyl, $C_{1-6}$ alkylsulfanyl, $C_{1-6}$ alkylsulfinyl, $C_{1-6}$ alkylsulfonyl, hydroxy, cyano, nitro, —$NR^6R^{6'}$, —$CO_2R^7$, —$CONR^8R^{8'}$ or the following group A, wherein when u is 2 or 3, two or more $R^3$s may be different from each other;
$R^6$ and $R^{6'}$ are each independently a hydrogen atom or $C_{1-6}$ alkyl;
$R^7$ is a hydrogen atom or $C_{1-6}$ alkyl;
$R^8$ and $R^{8'}$ are each independently a hydrogen atom, $C_{1-6}$ alkyl, carboxy $C_{1-6}$ alkyl, hydroxy $C_{1-6}$ alkyl, halo $C_{1-6}$ alkyl, $C_{3-8}$ cycloalkyl or 3- to 8-membered heterocycloalkyl;
group A is a group selected from the group consisting of following (a) to (h):
(a) $C_{6-10}$ aryl which is unsubstituted or substituted with 1 to 3 groups selected from substituent group B,
(b) 5- or 6-membered heteroaryl which is unsubstituted or substituted with 1 to 3 groups selected from substituent group B,
(c) $C_{6-10}$ aryl $C_{1-6}$ alkyl which is unsubstituted or substituted with 1 to 3 groups selected from substituent group B,
(d) $C_{6-10}$ aryloxy which is unsubstituted or substituted with 1 to 3 groups selected from substituent group B,
(e) 5- or 6-membered heteroaryl $C_{1-6}$ alkyl which is unsubstituted or substituted with 1 to 3 groups selected from substituent group B,
(f) 5- or 6-membered heteroaryloxy which is unsubstituted or substituted with 1 to 3 groups selected from substituent group B,
(g) $C_{3-8}$ cycloalkyl which is unsubstituted or substituted with 1 to 3 groups selected from substituent group B, and
(h) 3- to 8-membered heterocycloalkyl which is unsubstituted or substituted with 1 to 3 groups selected from substituent group B,
wherein substituent group B is a group consisting of a halogen atom, $C_{1-6}$ alkyl, halo $C_{1-6}$ alkyl, $C_{1-6}$ alkoxy, halo C$_{1-6}$ alkoxy, hydroxy, cyano, —NR$^9$R$^{9'}$, —NR$^9$SO$_2$R$^{10}$, —CO$_2$R$^{10}$ and —CONR$^{11}$R$^{11'}$;

wherein R$^9$ and R$^{9'}$ are each independently a hydrogen atom or C$_{1-6}$ alkyl;

R$^{10}$ is a hydrogen atom or C$_{1-6}$ alkyl; and

R$^{11}$ and R$^{11'}$ are each independently a hydrogen atom, C$_{1-6}$ alkyl, carboxy C$_{1-6}$ alkyl, hydroxy C$_{1-6}$ alkyl, halo C$_{1-6}$ alkyl, C$_{3-8}$ cycloalkyl or 3- to 8-membered heterocycloalkyl;

m, n and u are each independently an integer number 1 to 3;

p and q are each independently 1 or 2; and r is an integer number 0 to 6;

or a pharmaceutically acceptable salt thereof.

2. The compound according to claim 1, wherein ring Z is a group selected from the group consisting of following (a) to (J):

[Chem. 4]

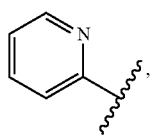
(a)

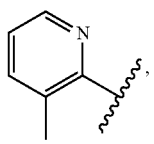
(b)

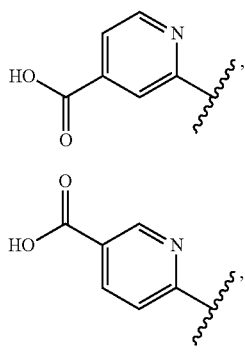
(c)

(d)

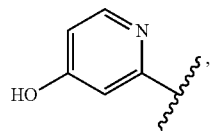
(e)

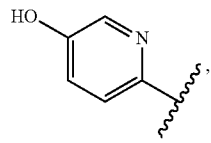
(f)

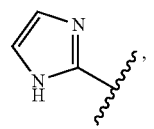
(g)

-continued

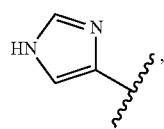
(h)

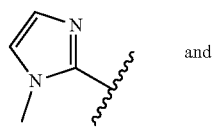
and
(i)

[Chem. 5]

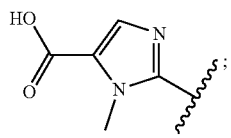
(j)

or a pharmaceutically acceptable salt thereof.

3. The compound according to claim 2 or a pharmaceutically acceptable salt thereof, wherein ring W is phenyl or 5- or 6-membered heteroaryl.

4. The compound according to claim 3 or a pharmaceutically acceptable salt thereof, wherein r is 0.

5. The compound according to claim 4 or a pharmaceutically acceptable salt thereof, wherein p is 2 and q is 1.

6. The compound according claim 5 or a pharmaceutically acceptable salt thereof, wherein R$^1$ is a hydrogen atom or a halogen atom.

7. The compound according to claim 6:
wherein R$^2$ is a hydrogen atom, C$_{1-6}$ alkyl, halo C$_{1-6}$ alkyl, C$_{1-6}$ alkoxy, carboxy or —CONR$^5$R$^{5'}$;
wherein R$^5$ and R$^{5'}$ are each independently a hydrogen atom, carboxy C$_{1-6}$ alkyl or 3- to 8-membered heterocycloalkyl;
or a pharmaceutically acceptable salt thereof.

8. The compound according to claim 7:
wherein R$^3$ is a hydrogen atom, a halogen atom, C$_{1-6}$ alkyl, halo C$_{1-6}$ alkyl, C$_{1-6}$ alkoxy, halo C$_{1-6}$ alkoxy, C$_{2-6}$ alkenyl, C$_{1-6}$ alkylsulfanyl, C$_{1-6}$ alkylsulfonyl, hydroxy, cyano, —CO$_2$R$^7$, —CONR$^8$R$^{8'}$ or group A;
wherein R$^7$ and u have the same meanings as those described in claim 1;
R$^8$ and R$^{8'}$ are each independently a hydrogen atom or carboxy C$_{1-6}$ alkyl; and
group A is phenyl which is unsubstituted or substituted with 1 to 3 groups selected from substituent group B or unsubstituted 5- or 6-membered heteroaryl;
wherein substituent group B is a halogen atom, C$_{1-6}$ alkyl, halo C$_{1-6}$ alkyl, C$_{1-6}$ alkoxy, halo C$_{1-6}$ alkoxy, hydroxy, cyano or carboxy;
or a pharmaceutically acceptable salt thereof.

9. The compound according to claim 8, wherein ring Z is a group selected from the group consisting of following (a) to (e):

[Chem. 6]

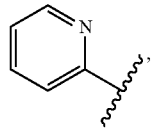
(a)

-continued

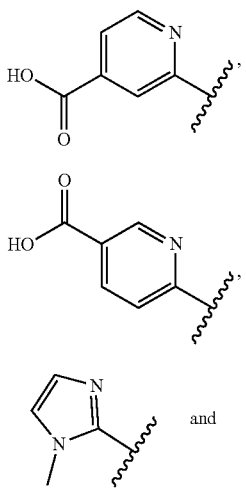

(b)

(c)

(d)

and

[Chem. 7]

(e)

or a pharmaceutically acceptable salt thereof.

10. The compound according to claim 9 which is represented by the following formula:

[Chem. 8]

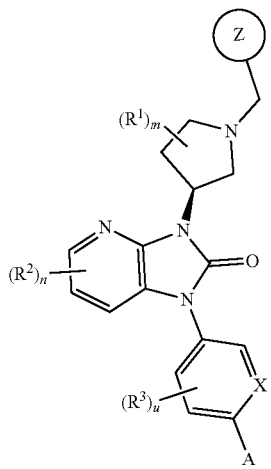

wherein
X is CR$^3$ or N;
u is 1 or 2;
R$^1$ has the same meanings as those described in claim 6;
R$^2$ has the same meanings as those described in claim 7;
R$^3$ is a hydrogen atom, C$_{1-6}$ alkyl or hydroxy;
group A has the same meanings as those described in claim 8;
ring Z has the same meanings as those described in claim 9; and
m and n have the same meanings as those described in claim 1;
or a pharmaceutically acceptable salt thereof.

11. The compound according to claim 1:
wherein u is 2 or 3;
one R$^3$ is group A; and
the other R$^3$s are each independently a hydrogen atom, a halogen atom, C$_{1-6}$ alkyl, halo C$_{1-6}$ alkyl, C$_{1-6}$ alkoxy, halo C$_{1-6}$ alkoxy, C$_{2-6}$ alkenyl, C$_{1-6}$ alkylsulfanyl, C$_{1-6}$ alkylsulfonyl, hydroxy, cyano, nitro, —NR$^6$R$^{6'}$, —CO$_2$R$^7$ or —CONR$^8$R$^{8'}$;
wherein group A, R$^6$, R$^{6'}$, R$^7$, R$^8$ and R$^{8'}$ have the same meanings as those described in claim 1;
or a pharmaceutically acceptable salt thereof.

12. A compound selected from the group consisting of the following compounds:

[Chem. 9]

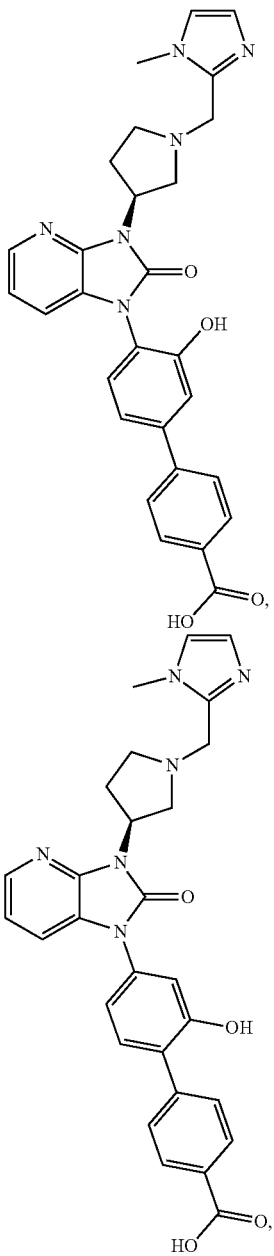

129
-continued
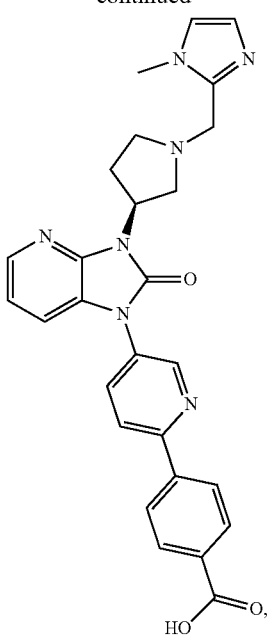
130
-continued
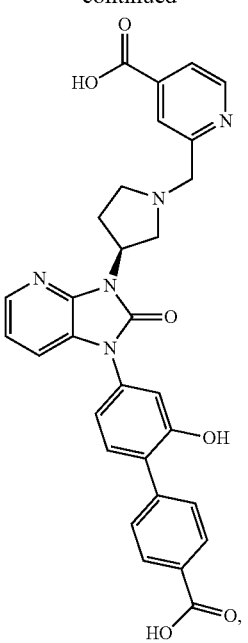
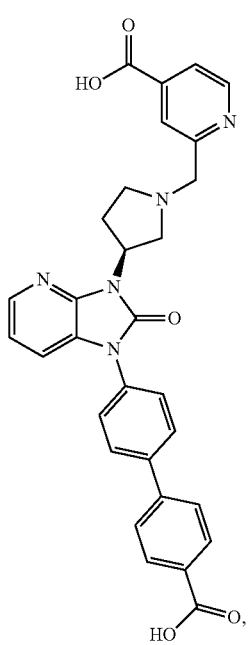
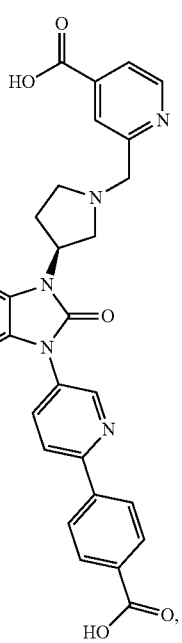

131
-continued
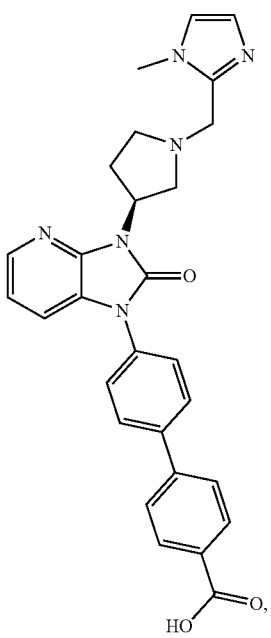
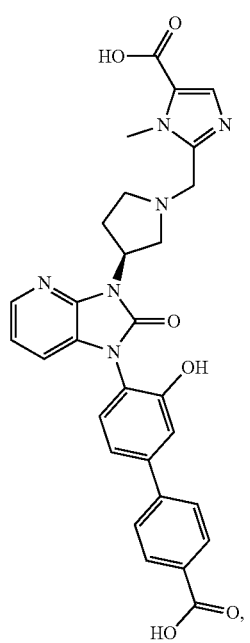
132
-continued
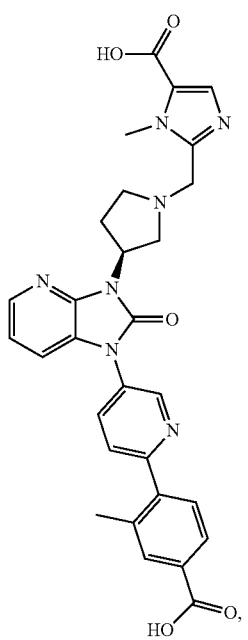
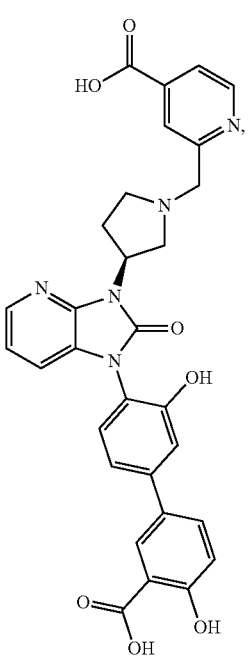

133
-continued

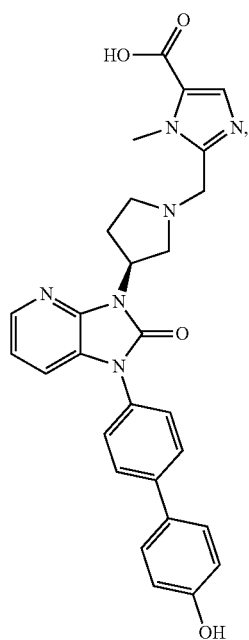

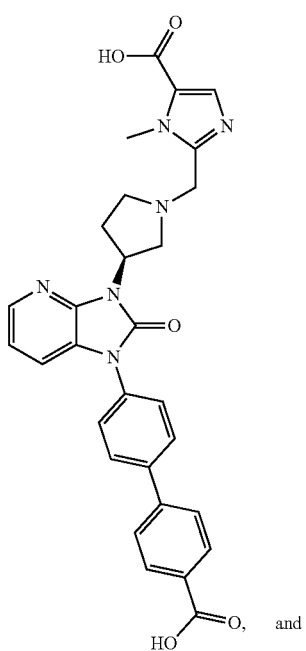
and

[Chem. 10]

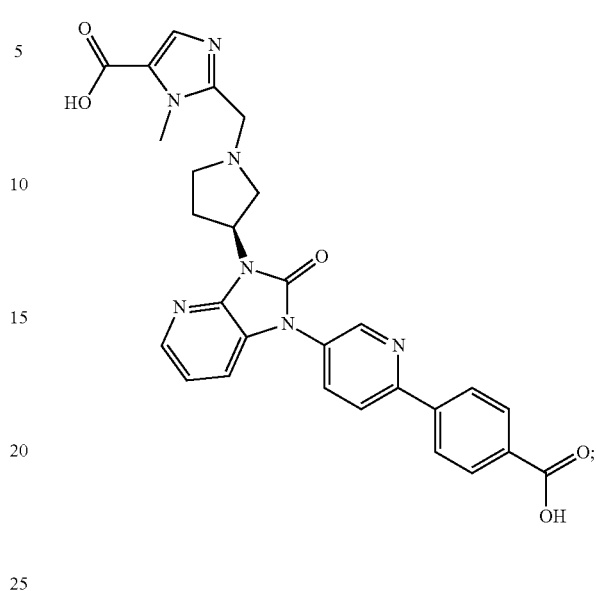

or a pharmaceutically acceptable salt thereof.

13. A compound represented by the following formula:

[Chem. 11]

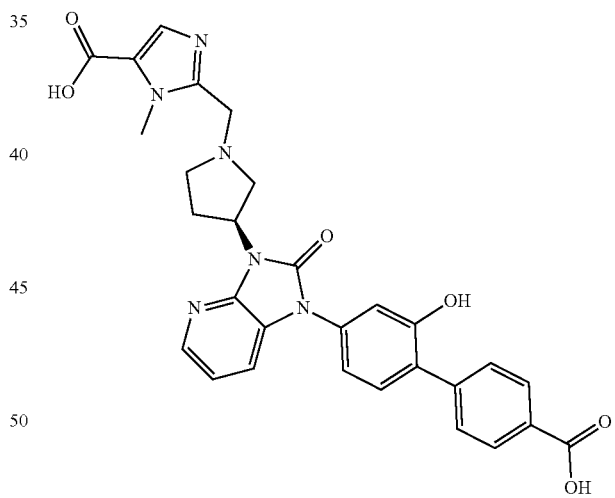

or a pharmaceutically acceptable salt thereof.

14. A pharmaceutical composition comprising the compound according to claim 1 or a pharmaceutically acceptable salt thereof, and pharmaceutical additive.

15. A method of treating an inflammatory bowel disease, the method comprising:

administering the pharmaceutical composition according to claim 14 to a subject in need thereof.

16. The method according to claim 15, wherein the inflammatory bowel disease is ulcerative colitis or Crohn's disease.

17. A compound represented by the following formula:
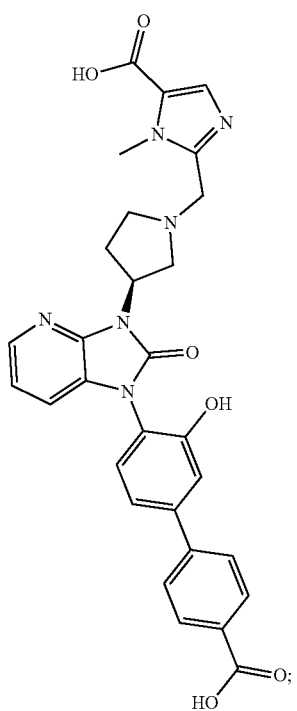 [SMILES: Cn1c(C(=O)O)cnc1CN1CC[C@H](n2c(=O)n(-c3ccc(-c4ccc(C(=O)O)cc4)cc3O)c3cccnc32)C1]
or a pharmaceutically acceptable salt thereof.
18. A compound represented by the following formula:
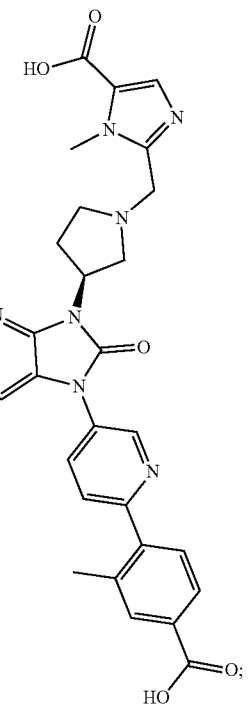
or a pharmaceutically acceptable salt thereof.
19. A compound represented by the following formula:
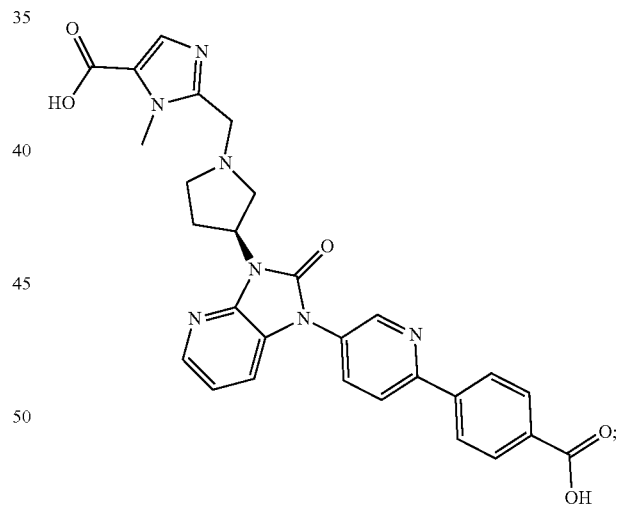
or a pharmaceutically acceptable salt thereof.
* * * * *